United States Patent [19]

Kimura et al.

[11] Patent Number: 5,591,752

[45] Date of Patent: Jan. 7, 1997

[54] QUINOLINE DERIVATIVE

[75] Inventors: Tomio Kimura, Niiza; Yoshio Kaku, Ube; Takashi Ikuta, Ube; Hiroshi Fujiwara, Ube; Hitoshi Ueno, Ube; Eiji Okanari, Ube, all of Japan

[73] Assignee: Ube Industries, Ltd., Yamaguchi, Japan

[21] Appl. No.: 505,172

[22] PCT Filed: Feb. 16, 1994

[86] PCT No.: PCT/JP94/00234

§ 371 Date: Aug. 16, 1995

§ 102(e) Date: Aug. 16, 1995

[87] PCT Pub. No.: WO94/19345

PCT Pub. Date: Sep. 1, 1994

[30] Foreign Application Priority Data

Feb. 16, 1993 [JP] Japan ..................... 5-026935

[51] Int. Cl.$^6$ ............. C07D 403/10; C07D 407/10; A61K 31/47

[52] U.S. Cl. ............. 514/314; 546/174; 546/176; 546/180

[58] Field of Search ................. 546/174, 176, 546/180; 514/314

[56] References Cited

U.S. PATENT DOCUMENTS

| 4,396,550 | 8/1983 | Takizawa et al. | 549/354 |
| 4,999,363 | 3/1991 | Oshima et al. | 514/332 |
| 5,010,087 | 4/1991 | Oshima et al. | 514/307 |

FOREIGN PATENT DOCUMENTS

| 0404440 | 12/1990 | European Pat. Off. |
| 56-150082 | 11/1981 | Japan. |
| 2-250 | 1/1990 | Japan. |
| 2-91040 | 3/1990 | Japan. |
| 3-38569 | 2/1991 | Japan. |

Primary Examiner—David B. Springer
Attorney, Agent, or Firm—Jordan and Hamburg

[57] ABSTRACT

This invention relates to a compound (a quinoline derivative) represented by the formula (I):

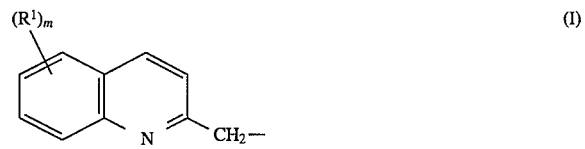

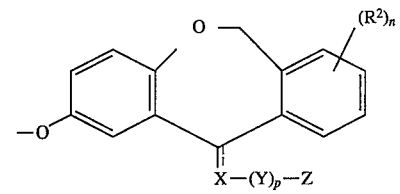

The quinoline derivative of this invention has a strong leukotriene antagonistic action and is extremely useful as an antiallergic medicine and an anti-inflammatory medicine.

10 Claims, No Drawings

QUINOLINE DERIVATIVE

This application is a 371 of PCT/JP94/00234 filed Feb. 16, 1994, and published as WO94/19345 Sep. 1, 1994.

TECHNICAL FIELD

This invention relates to a quinoline derivative and a salt thereof which have a thromboxane $A_2$ antagonistic action, a thromboxane A2-synthesizing enzyme inhibitory action and so on as well as a leukotriene $D_4$ antagonistic action and are useful as an antiallergic medicine and an anti-inflammatory medicine.

BACKGROUND ART

As a compound having a leukotriene $D_4$ antagonistic action as in the present invention and having a structure partially Similar to that of the compound of the present invention, there have been known, for example, 5-[3-[3-(2-quinolinylmethoxy)phenoxy]propyl]-1H-tetrazole (RG7152; J. Med. Chem. 1990, 33, 1186), 5-[[2-[[4-(2-quinolinylmethoxy)phenoxy]methyl]phenyl]methyl]-1H-tetrazole (RG12525; J. Med. Chem. 1990, 33, 1194), etc.

DISCLOSURE OF THE INVENTION

The present inventors have studied for many years in order to develop a compound having a strong leukotriene $D_4$ antagonistic action, and having a thromboxane $A_2$ antagonistic action, a thromboxane $A_2$-synthesizing enzyme inhibitory action, etc. as well as a leukotriene $D_4$ antagonistic action so that it can be an antiallergic medicine and an anti-inflammatory medicine which are clinically useful, and consequently found that a novel quinoline derivative having a dihydrodibenzoxepine skeleton in a molecule satisfies this object, to accomplish the present invention.

The present invention is a quinoline derivative represented by the formula (I):

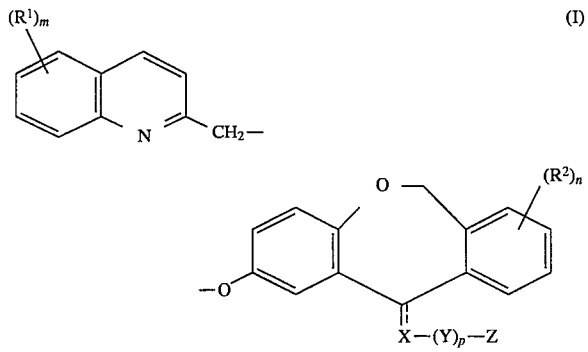

[wherein $R^1$ represents a group selected from a halogen atom, a lower alkyl group, a halogeno-lower alkyl group, a lower alkoxy group, a halogeno-lower alkoxy group, a lower alkylthio group and a halogeno-lower alkylthio group, m represents 0 or an integer of 1 to 4 and when m is 2 to 4, $R^1$s may be different from each other. $R^2$ represents a group selected from a halogen atom, a hydroxyl group, a nitro group, a cyano group, a carbamoyl group, a carboxy group, a tetrazol-5-yl group, a lower alkyl group or a lower alkoxy group or a lower alkylthio group which may be substituted by carboxy or tetrazol-5-yl, and an alkanoyl-lower alkyl group, n represents 0 or an integer of 1 to 4 and when n is 2 to 4, $R^2$s may be different from each other. X represents an oxygen atom, a sulfur atom, a methylene group, a formula of =CH— or a formula of =N—O—. Y represents a straight or branched alkylene group. Z represents a carboxy group, a tetrazol-5-yl group, a (tetrazol-5-yl)aminocarbonyl group, a (tetrazol-5-yl)carbonylamino group, a formula of —NH—CO—$R^3$, a formula of —NH—SO$_2$—$R^3$ or a formula of —CO—NH—SO$_2$—$R^3$ (wherein $R^3$ represents a lower alkyl group which may be substituted by a halogen, or a phenyl group which may be substituted by a halogen, a lower alkyl, a halogeno-lower alkyl, a lower alkoxy, a halogeno-lower alkoxy, nitro, cyano, carboxy or tetrazol-5-yl). p represents 0 or 1. ......... represents a single bond or a double bond] and a salt thereof.

In the compound represented by the above formula (I), the substituent $R^1$ in the formula is a group selected from a) a halogen atom, b) a lower alkyl group, c) a halogeno-lower alkyl group, d) a lower alkoxy group, e) a halogeno-lower alkoxy group, f) a lower alkylthio group and g) a halogeno-lower alkylthio group.

In $R^1$, as the halogen atom, there may be mentioned fluorine, chlorine, bromine and iodine; as the lower alkyl group, a $C_1$ to $C_4$ alkyl group such as methyl, ethyl, propyl, isopropyl, butyl, isobutyl, sec-butyl and t-butyl; as the halogeno-lower alkyl group, a halogeno-$C_1$ to $C_4$ alkyl group such as fluoromethyl, difluoromethyl, trifluoromethyl, trichloromethyl, 2-fluoroethyl, 2-chloroethyl, 2-bromoethyl, 2,2,2-trifluoroethyl, 2-fluoropropyl, 3-fluoropropyl, 3-chloropropyl, 3-bromopropyl, 3-iodopropyl, 4-fluorobutyl, 4-chlorobutyl, 4-bromobutyl and 4-iodobutyl; as the lower alkoxy group, a $C_1$ to $C_4$ alkoxy group such as methoxy, ethoxy, propoxy, isopropoxy, butoxy, isobutoxy, sec-butoxy and t-butoxy; as the halogeno-lower alkoxy group, a halogeno-$C_1$ to $C_4$ alkoxy group such as fluoromethoxy, difluoromethoxy, trifluoromethoxy, 2-fluoroethoxy, 2-chloroethoxy, 2-bromoethoxy, 2,2,2-trifluoroethoxy, 2-fluoropropoxy, 3-fluoropropoxy, 3-chloropropoxy, 3-bromopropoxy, 3-iodopropoxy, 4-fluorobutoxy, 4-chlorobutoxy, 4-bromobutoxy and 4-iodobutoxy; as the lower alkylthio group, a $C_1$ to $C_4$ alkylthio group such as methylthio, ethylthio, propylthio, isopropylthio, butylthio, isobutylthio, sec-butylthio and t-butylthio; and as the halogeno-lower alkylthio group, a halogeno-$C_1$ to $C_4$ alkylthio group such as fluoromethylthio, difluoromethylthio, trifluoromethylthio, 2-fluoroethylthio, 2-chloroethylthio, 2-bromoethylthio, 2,2,2-trifluoroethylthio, 2-fluoropropylthio, 3-fluoropropylthio, 3-chloropropylthio, 3-bromopropylthio, 3-iodopropylthio, 4-fluorobutylthio, 4-chlorobutylthio, 4-bromobutylthio and 4-iodobutylthio.

As $R^1$ in the formula (I), particularly preferred are fluorine, chlorine, bromine, iodine, methyl, ethyl, propyl, isopropyl, butyl, fluoromethyl, difluoromethyl, trifluoromethyl, methoxy, ethoxy, propoxy, isopropoxy, fluoromethoxy, difluoromethoxy, trifluoromethoxy, 2-fluoroethoxy, 2,2,2-trifluoroethoxy, methylthio, ethylthio, propylthio, fluoromethylthio, difluoromethylthio and trifluoromethylthio. Further, in the present invention, most preferred are fluorine, chlorine, methyl, ethyl, difluoromethyl, trifluoromethyl, methoxy, ethoxy, difluoromethoxy, trifluoromethoxy and 2,2,2-trifluoroethoxy. m is preferably 0, 1 or 2, particularly preferably 1 or 2.

In the above formula (I), the substituent $R^2$ is a group selected from a) a halogen atom, b) a hydroxyl group, c) a nitro group, d) a cyano group, e) a carbamoyl group, f) a carboxy group, g) a tetrazol-5-yl group, h) a lower alkyl group or a lower alkoxy group or a lower alkylthio group which may be substituted by carboxy or tetrazol-5-yl and i) an alkanoyl-lower alkyl group.

In $R^2$, as the halogen atom, there may be mentioned fluorine, chlorine, bromine and iodine; as the lower alkyl group, a $C_1$ to $C_4$ alkyl group such as methyl, ethyl, propyl, isopropyl, butyl, isobutyl, sec-butyl and t-butyl; as the lower alkoxy group, a $C_1$ to $C_4$ alkoxy group such as methoxy, ethoxy, propoxy, isopropoxy, butoxy, isobutoxy, sec-butoxy and t-butoxy; and as the lower alkylthio group, a $C_1$ to $C_4$ alkylthio group such as methylthio, ethylthio, propylthio, isopropylthio, butylthio, isobutylthio, sec-butylthio and t-butylthio.

In $R^2$, as the lower alkyl group substituted by carboxy, there may be mentioned a carboxy $C_1$ to $C_4$ alkyl group such as carboxymethyl, 1-carboxyethyl, 2-carboxyethyl, 3-carboxypropyl, 2-carboxypropyl, 2-carboxyisopropyl, 4-carboxybutyl and 3-carboxybutyl; as the lower alkoxy group substituted by carboxy, a carboxy $C_1$ to $C_4$ alkoxy group such as carboxymethoxy, 1-carboxyethoxy, 2-carboxyethoxy, 3-carboxypropoxy, 2-carboxylpropoxy, 2-carboxyisopropoxy, 4-carboxybutoxy and 3-carboxybutoxy; and as the lower alkylthio group substituted by carboxy, a carboxy $C_1$ to $C_4$ alkylthio group such as carboxymethylthio, 1-carboxyethylthio, 2-carboxyethylthio, 3-carboxypropylthio, 2-carboxypropylthio, 2-carboxyisopropylthio, 4-carboxybutylthio and 3-carboxybutylthio.

In $R^2$, as the lower alkyl group substituted by tetrazol-5-yl, there may be mentioned a tetrazol-5-yl $C_1$ to $C_4$ alkyl group such as (tetrazol-5-yl)methyl, 1-(tetrazol-5-yl)ethyl, 2-(tetrazol-5-yl)ethyl, 3-(tetrazol-5-yl)propyl, 2-(tetrazol-5-yl)propyl, 2-(tetrazol-5-yl)isopropyl, 4-(tetrazol-5-yl)butyl and 3-(tetrazol-5-yl)butyl; as the lower alkoxy group substituted by tetrazol-5-yl, a tetrazol-5-yl $C_1$ to $C_4$ alkoxy group such as (tetrazol-5-yl)methoxy, 1-(tetrazol-5-yl)ethoxy, 2-(tetrazol-5-yl)ethoxy, 3-(tetrazol-5-yl)propoxy, 2-(tetrazol-5-yl)propoxy, 2-(tetrazol-5-yl)isopropoxy, 4-(tetrazol-5-yl)butoxy and 3-(tetrazol-5-yl)butoxy; and as the lower alkylthio group substituted by tetrazol-5-yl, a tetrazol-5-yl $C_1$ to $C_4$ alkylthio group such as (tetrazol-5-yl)methylthio, 1-(tetrazol-5-yl)ethylthio, 2-(tetrazol-5-yl)ethylthio, 3-(tetrazol-5-yl)propylthio, 2-(tetrazol-5-yl)propylthio, 2-(tetrazol-5-yl)isopropylthio, 4-(tetrazol-5-yl)butylthio and 3-(tetrazol-5-yl)butylthio.

Further, in $R^2$, for example, as the alkanoyl-lower alkyl group, there may be mentioned a $C_1$ to $C_{10}$ alkanoyl $C_1$ to $C_4$ alkyl group such as formylmethyl, acetylmethyl, propanoylmethyl, butanoylmethyl, pentanoylmethyl, hexanoylmethyl, heptanoylmethyl, octanoylmethyl, nonanoylmethyl, decanoylmethyl, 2-formylethyl, 2-acetylethyl, 2-propanoylethyl, 2-butanoylethyl, 2-pentanoylethyl, 2-hexanoylethyl, 2-heptanoylethyl, 2-octanoylethyl, 2-nonanoylethyl, 2-decanoylethyl, 3-acetylpropyl and 4-acetylbutyl.

As $R^2$ in the formula (I), particularly preferred are nitro, cyano, carbamoyl, fluorine, chlorine, bromine, iodine, methyl, ethyl, propyl, methoxy, ethoxy, propoxy, methylthio, ethylthio, propylthio, carboxy, tetrazol-5-yl, carboxymethyl, 2-carboxyethyl, 3-carboxypropyl, 4-carboxybutyl, carboxymethoxy, 2-carboxyethoxy, 3-carboxypropoxy, 4-carboxybutoxy, carboxymethylthio, 2-carboxyethylthio, 3-carboxypropylthio, 4-carboxybutylthio, (tetrazol-5-yl)methyl, 2-(tetrazol-5-yl)ethyl, 3-(tetrazol-5-yl)propyl, 4-(tetrazol-5-yl)butyl, (tetrazol-5-yl)methoxy, 2-(tetrazol-5-yl)ethoxy, 3-(tetrazol-5-yl)propoxy, 4-(tetrazol-5-yl)butoxy, (tetrazol-5-yl)methylthio, 2-(tetrazol-5-yl)ethylthio, 3-(tetrazol-5-yl)propylthio, 4-(tetrazol-5-yl)butylthio, acetylmethyl, propanoylmethyl, 2-acetylethyl, 2-propanoylethyl and 3-acetylpropyl.

Further, in the present invention, as $R^2$ in the formula (I), most preferred are cyano, carbamoyl, fluorine, chlorine, bromine, methyl, ethyl, methoxy, ethoxy, methylthio, ethylthio, carboxy, tetrazol-5-yl, carboxymethyl, 2-carboxyethyl, carboxymethoxy, 2-carboxyethoxy, carboxymethylthio, 2-carboxyethylthio, (tetrazol-5-yl)methyl, 2-(tetrazol-5-yl)ethyl, (tetrazol-5-yl)methoxy, 2-(tetrazol-5-yl)ethoxy, (tetrazol-5-yl)methylthio, 2-(tetrazol-5-yl)ethylthio, 2-acetylethyl and 2-propanoylethyl. n is preferably 0, 1 or 2, particularly preferably 0 or 1.

Further, most preferred is a combination that $R^1$ is chlorine or fluorine, m is 1 or 2 and n is 0 or 1.

In the above formula (I), X is an oxygen atom, a sulfur atom, a methylene group, a formula of =CH— or a formula of =N-O—. In the present invention, as X, preferred is an oxygen atom, a sulfur atom, a methylene group or a formula of =CH— and further, most preferred is an oxygen atom or a sulfur atom.

In the formula (I), a bond between the dihydrodibenzoxepine skeleton (11-position) which is a main skeleton and X may be either a single bond or a double bond, preferably a single bond.

As the straight alkylene group of Y in the above formula (i), there may be mentioned a $C_1$ to $C_{10}$ straight alkylene group such as methylene, ethylene, trimethylene, tetramethylene, pentamethylene, hexamethylene, heptamethylene, octamethylene, nonamethylene and decamethylene; and as the branched alkylene group, a $C_1$ to $C_{10}$ branched alkylene group such as 1-methylethylene, 2-methylethylene, 1-methyltrimethylene, 2-methyltrimethylene, 3-methyltrimethylene, 1-methyltetramethylene, 2-methyltetramethylene, 3-methyltetramethylene and 4-methyltetramethylene.

As Y in the formula (I), particularly preferred are a $C_1$ to $C_4$ straight alkylene group such as methylene, ethylene, trimethylene, tetramethylene, etc. and a $C_1$ to $C_4$ branched alkylene group such as 1-methylethylene, 2-methylethylene, 1-methyltrimethylene, 2-methyltrimethylene, 3-methyltrimethylene, etc. Further, in the present invention, most preferred is a $C_1$ to $C_3$ straight or branched alkylene group such as methylene, ethylene, trimethylene, 1-methylethylene, 2-methylethylene, etc.

In the above formula (I), Z is a group represented by a carboxy group, a tetrazol-5-yl group, a (tetrazol-5-yl)aminocarbonyl group, a (tetrazol-5-yl)carbonylamino group, a formula of —NH—CO—$R^3$, a formula of —NH—SO$_2$—$R^3$ or a formula of —CO—NH—SO$_2$—$R^3$.

In the above formula (I), $R^3$ represents a lower alkyl group which may be substituted by a halogen as a substituent, or a phenyl group which may be substituted by a halogen, a lower alkyl, a halogeno-lower alkyl, a lower alkoxy, a halogeno-lower alkoxy, nitro, cyano, carboxy or tetrazol-5-yl.

As the lower alkyl group of the above $R^3$, there may be particularly mentioned a $C_1$ to $C_4$ alkyl group such as methyl, ethyl, propyl and butyl; and as the halogeno-lower alkyl group, a halogeno $C_1$ to $C_4$ alkyl group such as fluoromethyl, difluoromethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl, 3-iodopropyl, 4-fluorobutyl, 4-chlorobutyl, 4-bromobutyl and 4-iodobutyl, and there may be mentioned a phenyl group and a phenyl group substituted by the same halogen as described in $R^1$, a $C_1$ to $C_4$ alkyl, a halogeno $C_1$ to $C_4$ alkyl, a $C_1$ to $C_4$ alkoxy, a halogeno $C_1$ to $C_4$ alkoxy, nitro, cyano, carboxy or tetrazol-5-yl.

In the formula (I), Z is preferably a) a carboxy group, b) a tetrazol-5-yl group, c) a (tetrazol-5-yl)aminocarbonyl group or d) a (tetrazol-5-yl)carbonylamino group, and as the group represented by e) a formula of —NH—CO—$R^3$, there may be preferred a $C_1$ to $C_4$ alkylcarbonylamino group which may be substituted by a halogen, such as acetylamino, propionylamino, trifluoroacetylamino, trichloroacetylamino, etc., as the group represented by f) a formula of —NH—SO$_2$—R$^3$, a C$_1$ to C$_4$ alkylsulfonylamino group which may be substituted by a halogen such as methanesulfonylamino, ethanesulfonylamino, trifluoromethanesulfonylamino, trichloromethanesulfonylamino, etc.; and a phenylsulfonylamino group which may be substituted by a C$_1$ to C$_4$ alkyl, a halogen, carboxy or (tetrazol-5-yl) as a substituent, such as phenylsulfonylamino, 2, 3 or 4-methylphenylsulfonylamino, 2, 3 or 4-chlorophenylsulfonylamino, 4-carboxyphenylsulfonylamino, 4-(tetrazol-5-yl)phenylsulfonylamino, etc., and as the group represented by g) a formula of —CO—NH—SO$_2$—R$^3$, a C$_1$ to C$_4$ alkylsulfonylaminocarbonyl group which may be substituted by a halogen such as methanesulfonylaminocarbonyl, trifluoromethanesulfonylaminocarbonyl, trichloromethanesulfonylaminocarbonyl, etc.; and a phenylsulfonylaminocarbonyl group which may be substituted by a C$_1$ to C$_4$ alkyl, a halogen, carboxy or (tetrazol-5-yl) as a substituent, such as phenylsulfonylaminocarbonyl, 2, 3 or 4-methylphenylsulfonylaminocarbonyl, 2, 3 or 4-chlorophenylsulfonylaminocarbonyl, 4-carboxyphenylsulfonylaminocarbonyl, 4-(tetrazol-5-yl)phenylsulfonylaminocarbonyl, etc.

As Z in the formula (I), particularly preferred are carboxy, tetrazol-5-yl, trifluoroacetylamino, trifluoromethanesulfonylamino, phenylsulfonylamino, 2-methylphenylsulfonylamino, 4-carboxyphenylsulfonylamino, 4-(tetrazol-5-yl)phenylsulfonylamino, trifluoromethanesulfonylaminocarbonyl, phenylsulfonylaminocarbonyl, 2-methylphenylsulfonylaminocarbonyl, 4-carboxyphenylsulfonylaminocarbonyl and a 4-(tetrazol-5-yl)phenylsulfonylaminocarbonyl group.

In the above formula (I), p is preferably 0 or 1, particularly 1.

Further, most preferred is a combination that X is an oxygen atom or a sulfur atom, Y is a C$_1$ to C$_3$ alkylene, p is 1 and Z is carboxy or tetrazol-5-yl.

In the compound having the above formula (I), when at least either one of R$^2$ and Z is a group containing a carboxy group, hydrogen of the carboxy group (—COOH) may be protected by a protective group (e.g. a substituted or unsubstituted C$_1$ to C$_4$ alkyl group). As such a protective group, there may be mentioned a group which can be easily converted into a carboxy group in vivo such as a C$_1$ to C$_4$ alkyl group such as methyl, ethyl, propyl, isopropyl, butyl and isobutyl; an aryl C$_1$ to C$_4$ alkyl group such as benzyl and phenylethyl; a C$_1$ to C$_4$ alkanoyloxy C$_1$ to C$_4$ alkyl group such as acetoxymethyl and pivaloyloxymethyl; a C$_1$ to C$_4$ alkoxycarbonyloxy C$_1$ to C$_4$ alkyl group such as 1-(ethoxycarbonyloxy)ethyl and 1-(isorpopoxycarbonyloxy)ethyl; a N,N-di-substituted aminocarbonyl C$_1$ to C$_4$ alkyl group such as a N,N-dimethylaminocarbonylmethyl group; a N,N-di-substituted amino C$_1$ to C$_4$ alkyl group such as a N,N-dimethylaminoethyl group or a (5-methyl-2-oxo-1,3-dioxolen-4-yl)methyl group, etc.

The compound (I) of the present invention can be converted into a pharmaceutically acceptable salt, if necessary. As such a salt, there may be mentioned an acid addition salt of a mineral acid such as hydrochloride, hydrobromide, hydroiodide, sulfate and phosphate; an acid addition salt of an organic acid such as methanesulfonate, ethanesulfonate, benzenesulfonate, p-toluenesulfonate, oxalate, maleate, fumarate, tartrate and citrate; or a metal salt of a carboxylic acid such as a sodium salt, a potassium salt, a calcium salt, a magnesium salt, a manganese salt, an iron salt and an aluminum salt.

The compound (I) of the present invention can exist as a hydrate such as H$_2$O adduct (Example 9), ¾ H$_2$O adduct (Example 7), ½ H$_2$O adduct (Example 22) and ¼ H$_2$O adduct (Example 11).

In the following, examples of the compound of the present invention are shown in Table 1 to Table 18. In the chemical formulae described in the above tables, R$^1$, R$^2$, X, Y, Z, m, n and p have the same meanings as described above. In said tables, in the column of (R$^1$)$_m$ or (R$^2$)$_n$, for example, when H is described, it means that m or n is 0, and when 7 —Cl is described, it means that m or n is 1 and 7-position is substituted by a chlorine atom. "Tet" described in said tables is an abbreviation of a tetrazol-5-yl group. In the present specification, "a tetrazol-5-yl group" represents both tautomers shown below.

TABLE 1

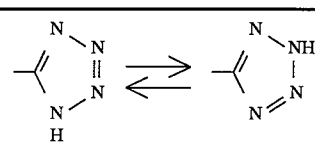

| No. | (R$^1$)$_m$ | (R$^2$)$_n$ | —X—(Y)$_p$—Z |
|---|---|---|---|
| 1 | H | H | —O—CH$_2$—COOH |
| 2 | H | H | —O—(CH$_2$)$_2$—COOH |
| 3 | H | H | —O—(CH$_2$)$_3$—COOH |
| 4 | H | H | —O—(CH$_2$)$_4$—COOH |
| 5 | H | H | —O—(CH$_2$)$_5$—COOH |
| 6 | H | H | —O—(CH$_2$)$_7$—COOH |
| 7 | H | H | —O—(CH$_2$)$_9$—COOH |
| 8 | H | H | —O—CH(CH$_3$)—COOH |
| 9 | H | H | —O—CH(CH$_3$)—CH$_2$—COOH |
| 10 | H | H | —O—CH$_2$—CH(CH$_3$)—COOH |
| 11 | H | H | —O—CH$_2$—Tet |
| 12 | H | H | —O—(CH$_2$)$_2$—Tet |
| 13 | H | H | —O—(CH$_2$)$_3$—Tet |
| 14 | H | H | —O—(CH$_2$)$_4$—Tet |
| 15 | H | H | —O—(CH$_2$)$_6$—Tet |
| 16 | H | H | —O—(CH$_2$)$_8$—Tet |
| 17 | H | H | —O—(CH$_2$)$_{10}$—Tet |
| 18 | H | H | —O—CH(CH$_3$)—Tet |
| 19 | H | H | —O—CH(CH$_3$)—CH$_2$—Tet |

TABLE 1-continued

[Structure: tetrazole tautomerism equilibrium shown]

[Structure diagram with numbered atoms and substituents $(R^1)_m$, $(R^2)_n$, and $-X-(Y)_p-Z$ group]

| No. | $(R^1)_m$ | $(R^2)_n$ | $-X-(Y)_p-Z$ |
|---|---|---|---|
| 20 | H | H | $-O-CH_2-\underset{\underset{CH_3}{|}}{CH}-Tet$ |

TABLE 2

[Structure diagram with numbered atoms and substituents $(R^1)_m$, $(R^2)_n$, and $-X-(Y)_p-Z$ group]

| No. | $(R^1)_m$ | $(R^2)_n$ | $-X-(Y)_p-Z$ |
|---|---|---|---|
| 21 | H | H | $-O-(CH_2)_2-NH-\overset{O}{\underset{\|}{C}}-CH_3$ |
| 22 | H | H | $-O-(CH_2)_2-NH-\overset{O}{\underset{\|}{C}}-CF_3$ |
| 23 | H | H | $-O-(CH_2)_3-NH-\overset{O}{\underset{\|}{C}}-CF_3$ |
| 24 | H | H | $-O-(CH_2)_2-NH-SO_2-CH_3$ |
| 25 | H | H | $-O-(CH_2)_2-NH-SO_2-C_2H_5$ |
| 26 | H | H | $-O-(CH_2)_2-NH-SO_2-CF_3$ |
| 27 | H | H | $-O-(CH_2)_3-NH-SO_2-CF_3$ |
| 28 | H | H | $-O-(CH_2)_2-NHSO_2-\text{Ph}$ |
| 29 | H | H | $-O-(CH_2)_2-NHSO_2-\text{Ph}-CH_3$ (para) |
| 30 | H | H | $-O-(CH_2)_2-NHSO_2-\text{Ph}-CH_3$ (meta) |
| 31 | H | H | $-O-(CH_2)_2-NHSO_2-\text{Ph}-Cl$ (para) |

TABLE 2-continued

[Structure diagram with numbered atoms and substituents $(R^1)_m$, $(R^2)_n$, and $-X-(Y)_p-Z$ group]

| No. | $(R^1)_m$ | $(R^2)_n$ | $-X-(Y)_p-Z$ |
|---|---|---|---|
| 32 | H | H | $-O-(CH_2)_2-NHSO_2-\text{Ph}-Cl$ (meta) |
| 33 | H | H | $-O-(CH_2)_2-NHSO_2-\text{Ph}-Cl$ (ortho) |
| 34 | H | H | $-O-(CH_2)_2-NHSO_2-\text{Ph}-Tet$ (para) |
| 35 | H | H | $-O-(CH_2)_2-NHSO_2-\text{Ph}-Tet$ (meta) |
| 36 | H | H | $-O-(CH_2)_2-NH-Tet$ |
| 37 | H | H | $-O-(CH_2)_3-NHSO_2-\text{Ph}$ |
| 38 | H | H | $-O-CH_2-\overset{O}{\underset{\|}{C}}-NH-SO_2-CH_3$ |
| 39 | H | H | $-O-(CH_2)_2-\overset{O}{\underset{\|}{C}}-NH-SO_2-CF_3$ |
| 40 | H | H | $-O-CH_2-\overset{O}{\underset{\|}{C}}-NHSO_2-\text{Ph}$ |

TABLE 3

[Structure diagram with numbered atoms and substituents $(R^1)_m$, $(R^2)_n$, and $-X-(Y)_p-Z$ group]

| No. | $(R^1)_m$ | $(R^2)_n$ | $-X-(Y)_p-Z$ |
|---|---|---|---|
| 41 | H | H | $-O-(CH_2)_2-\overset{O}{\underset{\|}{C}}-NHSO_2-\text{Ph}$ |

TABLE 3-continued

![structure with (R¹)ₘ on quinoline-like ring connected via CH=CH-C(=N)-CH₂-O to diphenylmethane with X-(Y)ₚ-Z at position 11]

| No. | (R¹)ₘ | (R²)ₙ | —X—(Y)ₚ—Z |
|---|---|---|---|
| 42 | H | H | —O—(CH₂)₂C(=O)NHSO₂—C₆H₄—CH₃ |
| 43 | H | H | —O—(CH₂)₂—C(=O)—NHSO₂—C₆H₄—CH₃ |
| 44 | H | H | —O—(CH₂)₂C(=O)NHSO₂—C₆H₄—Cl |
| 45 | H | H | —O—(CH₂)₂C(=O)NHSO₂—C₆H₄—COOH |
| 46 | H | H | —O—(CH₂)₂C(=O)NHSO₂—C₆H₄—Tet |
| 47 | H | H | =CH—COOH |
| 48 | H | H | =CH—CH₂—COOH |
| 49 | H | H | =CH—(CH₂)₂—COOH |
| 50 | H | H | —CH₂—COOH |
| 51 | H | H | —CH₂—CH₂—COOH |
| 52 | H | H | —CH₂—(CH₂)₂—COOH |
| 53 | H | H | =N—O—CH₂—COOH |
| 54 | 7-Cl | H | —O—(CH₂)₆—COOH |
| 55 | 7-Cl | H | —O—(CH₂)₈—COOH |
| 56 | 7-Cl | H | —O—(CH₂)₁₀—COOH |
| 57 | 7-Cl | H | —S—(CH₂)₆—COOH |
| 58 | 7-Cl | H | —S—(CH₂)₈—COOH |
| 59 | 7-Cl | H | —S—(CH₂)₁₀—COOH |
| 60 | 7-Cl | H | —S—CH₂—C(CH₃)₂—COOH |

TABLE 4

![same structure as Table 3]

| No. | (R¹)ₘ | (R²)ₙ | —X—(Y)—Z |
|---|---|---|---|
| 61 | 7-Cl | H | —O—CH₂—COOH |
| 62 | 7-Cl | H | —O—(CH₂)₂—COOH |
| 63 | 7-Cl | H | —O—(CH₂)₃—COOH |
| 64 | 7-Cl | H | —O—(CH₂)₄—COOH |

TABLE 4-continued

| No. | (R¹)ₘ | (R²)ₙ | —X—(Y)—Z |
|---|---|---|---|
| 65 | 7-Cl | H | —O—(CH₂)₅—COOH |
| 66 | 7-Cl | H | —O—(CH₂)₇—COOH |
| 67 | 7-Cl | H | —O—(CH₂)₉—COOH |
| 68 | 7-Cl | H | —O—CH(CH₃)—COOH |
| 69 | 7-Cl | H | —O—CH(CH₃)—CH₂—COOH |
| 70 | 7-Cl | H | —O—CH₂—CH(CH₃)—COOH |
| 71 | 7-Cl | H | —O—CH₂—Tet |
| 72 | 7-Cl | H | —O—(CH₂)₂—Tet |
| 73 | 7-Cl | H | —O—(CH₂)₃—Tet |
| 74 | 7-Cl | H | —O—(CH₂)₄—Tet |
| 75 | 7-Cl | H | —O—(CH₂)₆—Tet |
| 76 | 7-Cl | H | —O—(CH₂)₈—Tet |
| 77 | 7-Cl | H | —O—(CH₂)₁₀—Tet |
| 78 | 7-Cl | H | —O—CH(CH₃)—Tet |
| 79 | 7-Cl | H | —O—CH(CH₃)—CH₂—Tet |
| 80 | 7-Cl | H | —O—CH₂—CH(CH₃)—Tet |

TABLE 5

![structure with quinoline ring having (R¹)ₘ, connected via CH=CH-C(2)=N-CH₂-O to diphenylmethane system]

| No. | (R¹)ₘ | (R²)ₙ | —X—(Y)ₚ—Z |
|---|---|---|---|
| 81 | 7-Cl | H | —O—(CH₂)₂—NH—C(=O)—CH₃ |
| 82 | 7-Cl | H | —O—(CH₂)₂—NH—C(=O)—CF₃ |
| 83 | 7-Cl | H | —O—(CH₂)₃—NH—C(=O)—CF₃ |
| 84 | 7-Cl | H | —O—(CH₂)₂—NH—SO₂—CH₃ |
| 85 | 7-Cl | H | —O—(CH₂)₂—NH—SO₂—C₂H₅ |
| 86 | 7-Cl | H | —O—(CH₂)₂—NH—SO₂—CF₃ |
| 87 | 7-Cl | H | —O—(CH₂)₃—NH—SO₂—CF₃ |

TABLE 5-continued

| No. | $(R^1)_m$ | $(R^2)_n$ | $-X-(Y)_p-Z$ |
|---|---|---|---|
| 88 | 7-Cl | H | $-O-(CH_2)_2-NHSO_2-C_6H_5$ |
| 89 | 7-Cl | H | $-O-(CH_2)_2-NHSO_2-C_6H_4-CH_3$ (para) |
| 90 | 7-Cl | H | $-O-(CH_2)_2-NHSO_2-C_6H_4-CH_3$ (meta) |
| 91 | 7-Cl | H | $-O-(CH_2)_2-NHSO_2-C_6H_4-Cl$ (para) |
| 92 | 7-Cl | H | $-O-(CH_2)_2-NHSO_2-C_6H_4-Cl$ (ortho) |
| 93 | 7-Cl | H | $-O-(CH_2)_2-NHSO_2-C_6H_4-Cl$ (meta, Cl at top) |
| 94 | 7-Cl | H | $-O-(CH_2)_2-NHSO_2-C_6H_4-COOH$ |
| 95 | 7-Cl | H | $-O-(CH_2)_2-NHSO_2-C_6H_4-Tet$ |
| 96 | 7-Cl | H | $-O-(CH_2)_2-NH-Tet$ |
| 97 | 7-Cl | H | $-O-(CH_2)_3-NHSO_2-C_6H_5$ |
| 98 | 7-Cl | H | $-O-CH_2-C(O)-NH-SO_2-CH_3$ |
| 99 | 7-Cl | H | $-O-(CH_2)_2-C(O)-NH-SO_2-CF_3$ |
| 100 | 7-Cl | H | $-O-CH_2-C(O)-NHSO_2-C_6H_5$ |

TABLE 6

| No. | $(R^1)_m$ | $(R^2)_n$ | $-X-(Y)_p-Z$ |
|---|---|---|---|
| 101 | 7-Cl | H | $-O-(CH_2)_2-C(O)-NHSO_2-C_6H_5$ |
| 102 | 7-Cl | H | $-O-(CH_2)_2C(O)NHSO_2-C_6H_4-CH_3$ (para) |
| 103 | 7-Cl | H | $-O-(CH_2)_2-C(O)-NHSO_2-C_6H_4-CH_3$ (meta) |
| 104 | 7-Cl | H | $-O-(CH_2)_2C(O)NHSO_2-C_6H_4-Cl$ |
| 105 | 7-Cl | H | $-O-(CH_2)_2C(O)NHSO_2-C_6H_4-COOH$ |
| 106 | 7-Cl | H | $-O-(CH_2)_2C(O)NHSO_2-C_6H_4-Tet$ |
| 107 | 7-Cl | H | $=CH-COOH$ |
| 108 | 7-Cl | H | $=CH-CH_2-COOH$ |
| 109 | 7-Cl | H | $=CH-(CH_2)_2-COOH$ |
| 110 | 7-Cl | H | $-CH_2-COOH$ |
| 111 | 7-Cl | H | $-CH_2-CH_2-COOH$ |
| 112 | 7-Cl | H | $-CH_2-(CH_2)_2-COOH$ |
| 113 | 7-Cl | H | $=N-O-CH_2-COOH$ |
| 114 | 6-$C_2H_5$ | H | $-O-CH_2-COOH$ |
| 115 | 6-Cl | | $-O-CH_2-COOH$ |
| 116 | 6-F 7-Cl | H | $-O-CH_2-COOH$ |
| 117 | 6-F 7-Cl | H | $-O-(CH_2)_2-COOH$ |
| 118 | 6-F 7-Cl | H | $-O-(CH_2)_3-COOH$ |
| 119 | 6-F 7-Cl | H | $-O-CH(CH_3)-COOH$ |
| 120 | 6-F 7-Cl | H | $-O-CH_2-CH(CH_3)-COOH$ |

TABLE 7

| No. | $(R^1)_m$ | $(R^2)_n$ | $-X-(Y)_p-Z$ |
|---|---|---|---|
| 121 | H | H | $-S-CH_2-COOH$ |
| 122 | H | H | $-S-(CH_2)_2-COOH$ |
| 123 | H | H | $-S-(CH_2)_3-COOH$ |
| 124 | H | H | $-S-(CH_2)_4-COOH$ |
| 125 | H | H | $-S-(CH_2)_5-COOH$ |
| 126 | H | H | $-S-(CH_2)_7-COOH$ |
| 127 | H | H | $-S-(CH_2)_9-COOH$ |
| 128 | H | H | $-S-CH(CH_3)-COOH$ |
| 129 | H | H | $-S-CH(CH_3)-CH_2-COOH$ |
| 130 | H | H | $-S-CH_2-CH(CH_3)-COOH$ |
| 131 | H | H | $-S-CH_2-Tet$ |
| 132 | H | H | $-S-(CH_2)_2-Tet$ |
| 133 | H | H | $-S-(CH_2)_3-Tet$ |
| 134 | H | H | $-S-(CH_2)_4-Tet$ |
| 135 | H | H | $-S-(CH_2)_6-Tet$ |
| 136 | H | H | $-S-(CH_2)_8-Tet$ |
| 137 | H | H | $-S-(CH_2)_{10}-Tet$ |
| 138 | H | H | $-S-CH(CH_3)-Tet$ |
| 139 | H | H | $-S-CH(CH_3)-CH_2-Tet$ |
| 140 | H | H | $-S-CH_2-CH(CH_3)-Tet$ |

TABLE 8

| No. | $(R^1)_m$ | $(R^2)_n$ | $-X-(Y)_p-Z$ |
|---|---|---|---|
| 141 | H | H | $-S-(CH_2)_2-NH-C(=O)-CH_3$ |
| 142 | H | H | $-S-(CH_2)_2-NH-C(=O)-CF_3$ |
| 143 | H | H | $-S-(CH_2)_3-NH-C(=O)-CF_3$ |
| 144 | H | H | $-S-(CH_2)_2-NH-SO_2-CH_3$ |
| 145 | H | H | $-S-(CH_2)_2-NH-SO_2-C_2H_5$ |
| 146 | H | H | $-S-(CH_2)_2-NH-SO_2-CF_3$ |

TABLE 8-continued

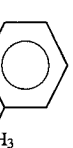

| No. | $(R^1)_m$ | $(R^2)_n$ | $-X-(Y)_p-Z$ |
|---|---|---|---|
| 147 | H | H | $-S-(CH_2)_3-NH-SO_2-CF_3$ |
| 148 | H | H | 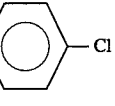 $-S-(CH_2)_2-NHSO_2-C_6H_5$ |
| 149 | H | H | $-S-(CH_2)_2-NHSO_2-C_6H_4-CH_3$ |
| 150 | H | H | $-S-(CH_2)_2-NHSO_2-C_6H_4-CH_3$ |
| 151 | H | H | $-S-(CH_2)_2-NHSO_2-C_6H_4-Cl$ |
| 152 | H | H | $-S-(CH_2)_2-NHSO_2-C_6H_4-Cl$ |
| 153 | H | H | $-S-(CH_2)_2-NHSO_2-C_6H_4-Cl$ |
| 154 | H | H | $-S-(CH_2)_2-NHSO_2-C_6H_4-COOH$ |
| 155 | H | H | $-S-(CH_2)_2-NHSO_2-C_6H_4-Tet$ |
| 156 | H | H | $-S-(CH_2)_2-NH-C(=O)-Tet$ |
| 157 | H | H | $-S-(CH_2)_3-NHSO_2-C_6H_5$ |
| 158 | H | H | $-S-CH_2-C(=O)-NH-SO_2-CH_3$ |
| 159 | H | H | $-S-(CH_2)_2-C(=O)-NH-SO_2-CF_3$ |

TABLE 8-continued

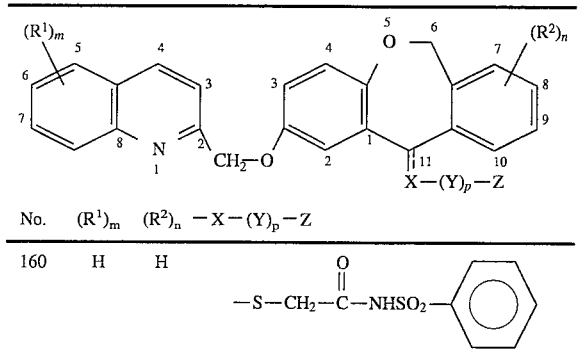

| No. | (R¹)ₘ | (R²)ₙ | —X—(Y)ₚ—Z |
|---|---|---|---|
| 160 | H | H | —S—CH₂—C(=O)—NHSO₂—C₆H₅ |

TABLE 9

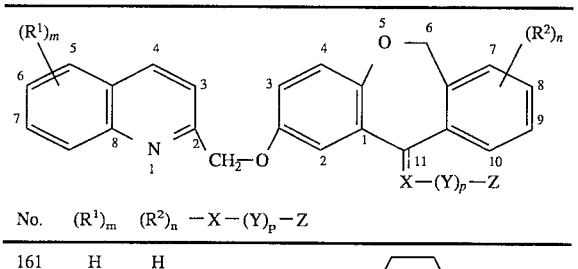

| No. | (R¹)ₘ | (R²)ₙ | —X—(Y)ₚ—Z |
|---|---|---|---|
| 161 | H | H | —S—(CH₂)₂—NHSO₂—C₆H₄—CN |
| 162 | H | H | —S—(CH₂)₂—C(=O)—NHSO₂—C₆H₅ |
| 163 | H | H | —S—(CH₂)₂CNHSO₂—C₆H₄—CH₃ |
| 164 | H | H | —S—(CH₂)₂—C(=O)—NHSO₂—C₆H₄—CH₃ |
| 165 | H | H | —S—(CH₂)₂CNHSO₂—C₆H₄—Cl |
| 166 | H | H | —S—(CH₂)₂CNHSO₂—C₆H₄—COOH |
| 167 | H | H | —S—(CH₂)₂CNHSO₂—C₆H₄—Tet |
| 168 | H | H | —S—CH₂—C(=O)—NH—Tet |
| 169 | H | H | —S—(CH₂)₂—C(=O)—NH—Tet |

TABLE 9-continued

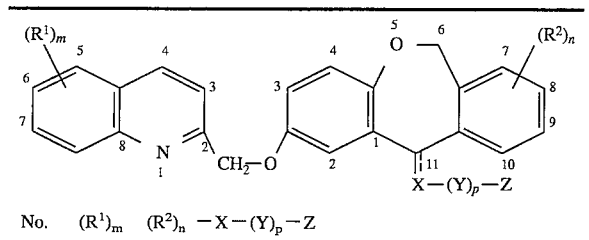

| No. | (R¹)ₘ | (R²)ₙ | —X—(Y)ₚ—Z |
|---|---|---|---|
| 170 | 6-F, 7-Cl | H | —O—CH₂—Tet |
| 171 | 6-F, 7-Cl | H | —O—(CH₂)₂—Tet |
| 172 | 6-F, 7-Cl | H | —O—(CH₂)₃—Tet |
| 173 | 6-F, 7-Cl | H | —S—(CH₂)₆—COOH |
| 174 | 6-F, 7-Cl | H | —S—(CH₂)₈—COOH |
| 175 | 6-F, 7-Cl | H | —S—(CH₂)₁₀—COOH |
| 176 | 6-F, 7-Cl | H | —S—CH₂—CH(CH₃)₂—COOH |
| 177 | 6-F, 7-Cl | H | =CH—COOH |
| 178 | 6-F, 7-Cl | H | —CH₂—COOH |
| 179 | 6-F, 7-Cl | H | =N—O—CH₂—COOH |
| 180 | H | 8-Tet | —S—(CH₂)₂—COOH |

TABLE 10

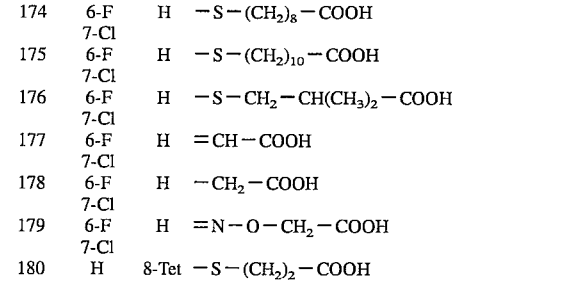

| No. | (R¹)ₘ | (R²)ₙ | —X—(Y)ₚ—Z |
|---|---|---|---|
| 181 | 7-Cl | H | —S—CH₂—COOH |
| 182 | 7-Cl | H | —S—(CH₂)₂—COOH |
| 183 | 7-Cl | H | —S—(CH₂)₃—COOH |
| 184 | 7-Cl | H | —S—(CH₂)₄—COOH |
| 185 | 7-Cl | H | —S—(CH₂)₅—COOH |
| 186 | 7-Cl | H | —S—(CH₂)₇—COOH |
| 187 | 7-Cl | H | —S—(CH₂)₉—COOH |
| 188 | 7-Cl | H | —S—CH(CH₃)—COOH |
| 189 | 7-Cl | H | —S—CH(CH₃)—CH₂—COOH |
| 190 | 7-Cl | H | —S—CH₂—CH(CH₃)—COOH |
| 191 | 7-Cl | H | —S—CH₂-Tet |
| 192 | 7-Cl | H | —S—(CH₂)₂-Tet |
| 193 | 7-Cl | H | —S—(CH₂)₃-Tet |
| 194 | 7-Cl | H | —S—(CH₂)₄-Tet |
| 195 | 7-Cl | H | —S—(CH₂)₆-Tet |
| 196 | 7-Cl | H | —S—(CH₂)₈-Tet |
| 197 | 7-Cl | H | —S—(CH₂)₁₀-Tet |
| 198 | 7-Cl | H | —S—CH(CH₃)-Tet |

TABLE 10-continued

[Structure: quinoline-CH=CH-C(=N)-CH₂-O-phenyl-CH₂-O-CH₂-phenyl with (R¹)ₘ on left ring and (R²)ₙ on right ring, with X—(Y)ₚ—Z substituent at position 11]

| No. | (R¹)ₘ | (R²)ₙ | —X—(Y)p—Z |
|---|---|---|---|
| 199 | 7-Cl | H | —S—CH(CH₃)—CH₂-Tet |
| 200 | 7-Cl | H | —S—CH₂—CH(CH₃)-Tet |

TABLE 11

[Same core structure as above]

| No. | (R¹)ₘ | (R²)ₙ | —X—(Y)p—Z |
|---|---|---|---|
| 201 | 7-Cl | H | —S—(CH₂)₂—NH—C(=O)—CH₃ |
| 202 | 7-Cl | H | —S—(CH₂)₂—NH—C(=O)—CF₃ |
| 203 | 7-Cl | H | —S—(CH₂)₃—NH—C(=O)—CF₃ |
| 204 | 7-Cl | H | —S—(CH₂)₂—NH—SO₂—CH₃ |
| 205 | 7-Cl | H | —S—(CH₂)₂—NH—SO₂—C₂H₅ |
| 206 | 7-Cl | H | —S—(CH₂)₂—NH—SO₂—CF₃ |
| 207 | 7-Cl | H | —S—(CH₂)₃—NH—SO₂—CF₃ |
| 208 | 7-Cl | H | —S—(CH₂)₂—NHSO₂—C₆H₅ |
| 209 | 7-Cl | H | —S—(CH₂)₂—NHSO₂—C₆H₄—CH₃ |
| 210 | 7-Cl | H | —S—(CH₂)₂—NHSO₂—C₆H₄—CH₃ (meta) |

TABLE 11-continued

| No. | (R¹)ₘ | (R²)ₙ | —X—(Y)p—Z |
|---|---|---|---|
| 211 | 7-Cl | H | —S—(CH₂)₂—NHSO₂—C₆H₄—Cl (para) |
| 212 | 7-Cl | H | —S—(CH₂)₂—NHSO₂—C₆H₄—Cl (meta) |
| 213 | 7-Cl | H | —S—(CH₂)₂—NHSO₂—C₆H₄—Cl (ortho) |
| 214 | 7-Cl | H | —S—(CH₂)₂—NHSO₂—C₆H₄—COOH |
| 215 | 7-Cl | H | —S—(CH₂)₂—NHSO₂—C₆H₄—Tet |
| 216 | 7-Cl | H | —S—(CH₂)₂—NH—C(=O)-Tet |
| 217 | 7-Cl | H | —S—(CH₂)₃—NHSO₂—C₆H₅ |
| 218 | 7-Cl | H | —S—CH₂—C(=O)—NH—SO₂—CH₃ |
| 219 | 7-Cl | H | —S—CH₂—C(=O)—NH—SO₂—CF₃ |
| 220 | 7-Cl | H | —S—CH₂—C(=O)—NHSO₂—C₆H₅ |

TABLE 12

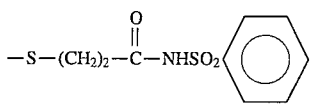

| No. | (R¹)ₘ | (R²)ₙ | −X−(Y)p−Z |
|---|---|---|---|
| 221 | 7-Cl | H | −S−(CH₂)₂−C(=O)−NHSO₂−Ph |
| 222 | 7-Cl | H | −S−(CH₂)₂CNHSO₂−Ph-CH₃ |
| 223 | 7-Cl | H | −S−(CH₂)₂−C(=O)−NHSO₂−Ph(o-CH₃) |
| 224 | 7-Cl | H | −S−(CH₂)₂CNHSO₂−Ph-Cl |
| 225 | 7-Cl | H | −S−(CH₂)₂CNHSO₂−Ph-COOH |
| 226 | 7-Cl | H | −S−(CH₂)₂CNHSO₂−Ph-Tet |
| 227 | 7-Cl | H | −S−(CH₂)₂−C(=O)−NH-Tet |
| 228 | 7-Cl | H | −S−CH₂−C(=O)−NH-Tet |
| 229 | 6-OCH₃ | H | −S−(CH₂)₂−COOH |
| 230 | 6-F | H | −S−(CH₂)₂−COOH |
| 231 | 6-C₂H₅ | H | −S−(CH₂)₂−COOH |
| 232 | 6-Cl | H | −S−(CH₂)₂−COOH |
| 233 | 7-F | H | −S−(CH₂)₂−COOH |
| 234 | 8-F | H | −S−(CH₂)₂−COOH |
| 235 | 5-Cl, 7-Cl | H | −S−(CH₂)₂−COOH |
| 236 | 7-OCHF₂ | H | −S−(CH₂)₂−COOH |
| 237 | 7-Cl | 8-OCH₃ | −S−(CH₂)₂−COOH |
| 238 | 7-Cl | 8-Br | −S−(CH₂)₂−COOH |
| 239 | 7-Cl | 10-CH₃ | −S−(CH₂)₂−COOH |
| 240 | 7-Cl | 7-CN | −S−(CH₂)₂−COOH |

TABLE 13

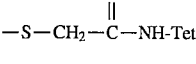

| No. | (R¹)ₘ | (R²)ₙ | −X−(Y)p−Z |
|---|---|---|---|
| 241 | 7-Cl | 7-CO−NH₂ | −S−(CH₂)₂−COOH |
| 242 | 7-Cl | 7-Tet | −S−(CH₂)₂−COOH |
| 243 | 7-Cl | 8-Tet | −S−(CH₂)₂−COOH |
| 244 | 7-Cl | 9-Tet | −S−(CH₂)₂−COOH |
| 245 | 7-Cl | 10-Tet | −S−(CH₂)₂−COOH |
| 246 | 7-Cl | 7-CH₂-Tet | −S−(CH₂)₂−COOH |
| 247 | 7-Cl | 8-CH₂-Tet | −S−(CH₂)₂−COOH |
| 248 | 7-Cl | 9-CH₂-Tet | −S−(CH₂)₂−COOH |
| 249 | 7-Cl | 7-COOH | −S−(CH₂)₂−COOH |
| 250 | 7-Cl | 8-COOH | −S−(CH₂)₂−COOH |
| 251 | 7-Cl | 9-COOH | −S−(CH₂)₂−COOH |
| 252 | 7-Cl | 10-COOH | −S−(CH₂)₂−COOH |

TABLE 13-continued

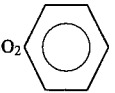

| No. | (R¹)$_m$ | (R²)$_n$ | —X—(Y)p—Z |
|---|---|---|---|
| 253 | 7-Cl | 7-CH$_2$—COOH | —S—(CH$_2$)$_2$—COOH |
| 254 | 7-Cl | 8-CH$_2$—COOH | —S—(CH$_2$)$_2$—COOH |
| 255 | 7-Cl | 9-CH$_2$—COOH | —S—(CH$_2$)$_2$—COOH |
| 256 | 7-Cl | 10-CH$_2$—COOH | —S—(CH$_2$)$_2$—COOH |
| 257 | 7-Cl | 7-O—CH$_2$COOH | —S—(CH$_2$)$_2$—COOH |
| 258 | 7-Cl | 8-O—CH$_2$COOH | —S—(CH$_2$)$_2$—COOH |
| 259 | 7-Cl | 9-O—CH$_2$COOH | —S—(CH$_2$)$_2$—COOH |
| 260 | 7-Cl | 8-S—CH$_2$COOH | —S—(CH$_2$)$_2$—COOH |

TABLE 14

| No. | (R¹)$_m$ | (R²)$_n$ | —X—(Y)p—Z |
|---|---|---|---|
| 261 | 6-F, 7-Cl | H | —S—CH$_2$—COOH |
| 262 | 6-F, 7-Cl | H | —S—(CH$_2$)$_2$—COOH |
| 263 | 6-F, 7-Cl | H | —S—(CH$_2$)$_3$—COOH |
| 264 | 6-F, 7-Cl | H | —S—(CH$_2$)$_4$—COOH |
| 265 | 6-F, 7-Cl | H | —S—(CH$_2$)$_5$—COOH |
| 266 | 6-F, 7-Cl | H | —S—(CH$_2$)$_7$—COOH |
| 267 | 6-F, 7-Cl | H | —S—(CH$_2$)$_9$—COOH |
| 268 | 6-F, 7-Cl | H | —S—CH(CH$_3$)—COOH |
| 269 | 6-F, 7-Cl | H | —S—CH(CH$_3$)—CH$_2$—COOH |
| 270 | 6-F, 7-Cl | H | —S—CH$_2$—CH(CH$_3$)—COOH |
| 271 | 6-F, 7-Cl | H | —S—CH$_2$-Tet |
| 272 | 6-F, 7-Cl | H | —S—(CH$_2$)$_2$-Tet |
| 273 | 6-F, 7-Cl | H | —S—(CH$_2$)$_3$-Tet |
| 274 | 6-F, 7-Cl | H | —S—(CH$_2$)$_4$-Tet |
| 275 | 6-F, 7-Cl | H | —S—(CH$_2$)$_6$-Tet |
| 276 | 6-F, 7-Cl | H | —S—(CH$_2$)$_8$-Tet |
| 277 | 6-F, 7-Cl | H | —S—(CH$_2$)$_{10}$-Tet |
| 278 | 6-F, 7-Cl | H | —S—CH(CH$_3$)-Tet |

TABLE 14-continued

| No. | (R¹)$_m$ | (R²)$_n$ | —X—(Y)p—Z |
|---|---|---|---|
| 279 | 6-F, 7-Cl | H | —S—CH(CH$_3$)—CH$_2$-Tet |
| 280 | 6-F, 7-Cl | H | —S—CH$_2$—CH(CH$_3$)-Tet |

TABLE 15

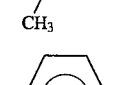

| No. | (R¹)$_m$ | (R²)$_n$ | —X—(Y)p—Z |
|---|---|---|---|
| 281 | 6-F, 7-Cl | H | —S—(CH$_2$)$_2$—NH—C(=O)—CH$_3$ |
| 282 | 6-F, 7-Cl | H | —S—(CH$_2$)$_2$—NH—C(=O)—CF$_3$ |
| 283 | 6-F, 7-Cl | H | —S—(CH$_2$)$_3$—NH—C(=O)—CF$_3$ |
| 284 | 6-F, 7-Cl | H | —S—(CH$_2$)$_2$—NH—SO$_2$—CH$_3$ |
| 285 | 6-F, 7-Cl | H | —S—(CH$_2$)$_2$—NH—SO$_2$—C$_2$H$_5$ |
| 286 | 6-F, 7-Cl | H | —S—(CH$_2$)$_2$—NH—SO$_2$—CF$_3$ |
| 287 | 6-F, 7-Cl | H | —S—(CH$_2$)$_3$—NH—SO$_2$—CF$_3$ |
| 288 | 6-F, 7-Cl | H | —S—(CH$_2$)$_2$—NHSO$_2$—C$_6$H$_5$ |
| 289 | 6-F, 7-Cl | H | —S—(CH$_2$)$_2$—NHSO$_2$—C$_6$H$_4$—CH$_3$ |
| 290 | 6-F, 7-Cl | H | —S—(CH$_2$)$_2$—NHSO$_2$—C$_6$H$_4$—CH$_3$ |
| 291 | 6-F, 7-Cl | H | —S—(CH$_2$)$_2$—NHSO$_2$—C$_6$H$_4$—Cl |

TABLE 15-continued

| No. | $(R^1)_m$ | $(R^2)_n$ | $-X-(Y)_p-Z$ |
|---|---|---|---|
| 292 | 6-F, 7-Cl | H | $-S-(CH_2)_2-NHSO_2-$(3-Cl-phenyl) |
| 293 | 6-F, 7-Cl | H | $-S-(CH_2)_2-NHSO_2-$(2-Cl-phenyl) |
| 294 | 6-F, 7-Cl | H | $-S-(CH_2)_2-NHSO_2-$(phenyl-COOH) |
| 295 | 6-F, 7-Cl | H | $-S-(CH_2)_2-NHSO_2-$(phenyl-Tet) |
| 296 | 6-F, 7-Cl | H | $-S-(CH_2)_2-NH-C(=O)-Tet$ |
| 297 | 6-F, 7-Cl | H | $-S-(CH_2)_3-NHSO_2-$phenyl |
| 298 | 6-F, 7-Cl | H | $-S-CH_2-C(=O)-NH-SO_2-CH_3$ |
| 299 | 6-F, 7-Cl | H | $-S-(CH_2)_2-C(=O)-NH-SO_2-CF_3$ |
| 300 | 6-F, 7-Cl | H | $-S-CH_2-C(=O)-NHSO_2-$phenyl |

TABLE 16

| No. | $(R^1)_m$ | $(R^2)_n$ | $-X-(Y)_p-Z$ |
|---|---|---|---|
| 301 | 6-F, 7-Cl | H | $-S-(CH_2)_2-C(=O)-NHSO_2-$phenyl |

TABLE 16-continued

| No. | $(R^1)_m$ | $(R^2)_n$ | $-X-(Y)_p-Z$ |
|---|---|---|---|
| 302 | 6-F, 7-Cl | H | $-S-(CH_2)_2CNHSO_2-$(4-CH$_3$-phenyl) with C=O |
| 303 | 6-F, 7-Cl | H | $-S-(CH_2)_2-C(=O)-NHSO_2-$(2-CH$_3$-phenyl) |
| 304 | 6-F, 7-Cl | H | $-S-(CH_2)_2CNHSO_2-$(Cl-phenyl) with C=O |
| 305 | 6-F, 7-Cl | H | $-S-(CH_2)_2CNHSO_2-$(COOH-phenyl) with C=O |
| 306 | 6-F, 7-Cl | H | $-S-(CH_2)_2CNHSO_2-$(Tet-phenyl) with C=O |
| 307 | 6-F, 7-Cl | H | $-S-CH_2-C(=O)-NH-Tet$ |
| 308 | 6-F, 7-Cl | H | $-S-(CH_2)_2-C(=O)-NH-Tet$ |

TABLE 17

| No. | $(R^1)_m$ | $(R^2)_n$ | $-X-(Y)_p-Z$ |
|---|---|---|---|
| 309 | 6-F, 7-Cl | 7-Tet | $-S-(CH_2)_2-COOH$ |
| 310 | 6-F, 7-Cl | 8-Tet | $-S-(CH_2)_2-COOH$ |
| 311 | 6-F, 7-Cl | 9-Tet | $-S-(CH_2)_2-COOH$ |
| 312 | 6-F, 7-Cl | 10-Tet | $-S-(CH_2)_2-COOH$ |
| 313 | 6-F, 7-Cl | 7-CH$_2$-Tet | $-S-(CH_2)_2-COOH$ |
| 314 | 6-F, 7-Cl | 8-CH$_2$-Tet | $-S-(CH_2)_2-COOH$ |
| 315 | 6-F, 7-Cl | 9-CH$_2$-Tet | $-S-(CH_2)_2-COOH$ |
| 316 | 6-F, 7-Cl | 10-CH$_2$-Tet | $-S-(CH_2)_2-COOH$ |
| 317 | 6-F | 7-COOH | $-S-(CH_2)_2-COOH$ |

TABLE 17-continued

| No. | (R¹)ₘ | (R²)ₙ | —X—(Y)p—Z |
|---|---|---|---|
| 318 | 6-F 7-Cl | 8-COOH | —S—(CH$_2$)$_2$—COOH |
| 319 | 6-F 7-Cl | 9-COOH | —S—(CH$_2$)$_2$—COOH |
| 320 | 6-F 7-Cl | 10-COOH | —S—(CH$_2$)$_2$—COOH |
| 321 | 6-F 7-Cl | 7-CH$_2$—COOH | —S—(CH$_2$)$_2$—COOH |
| 322 | 6-F 7-Cl | 8-CH$_2$—COOH | —S—(CH$_2$)$_2$—COOH |
| 323 | 6-F 7-Cl | 9-CH$_2$—COOH | —S—(CH$_2$)$_2$—COOH |
| 324 | 6-F 7-Cl | 10-CH$_2$—COOH | —S—(CH$_2$)$_2$—COOH |
| 325 | 6-F 7-Cl | 7-O—CH$_2$COOH | —S—(CH$_2$)$_2$—COOH |
| 326 | 6-F 7-Cl | 8-O—CH$_2$COOH | —S—(CH$_2$)$_2$—COOH |
| 327 | 6-F 7-Cl | 8-S—CH$_2$COOH | —S—(CH$_2$)$_2$—COOH |
| 328 | 6-F 7-Cl | 10-O—CH$_2$COOH | —S—(CH$_2$)$_2$—COOH |

TABLE 18

| No. | (R¹)ₘ | (R²)ₙ | —X—(Y)p—Z |
|---|---|---|---|
| 329 | 5-Cl 6-F | H | —S—(CH$_2$)$_2$—COOH |

TABLE 18-continued

| No. | (R¹)ₘ | (R²)ₙ | —X—(Y)p—Z |
|---|---|---|---|
| 330 | 6-F 7-Cl | 7-CN | —S—(CH$_2$)$_2$—COOH |
| 331 | 6-F 7-Cl | 8-(CH$_2$)$_2$—COCH$_3$ | —S—(CH$_2$)$_2$—COOH |
| 332 | 6-F 7-Cl | 8-CH$_2$COCH$_3$ | —S—(CH$_2$)$_2$—COOH |
| 333 | 6-F 7-Cl | 8-CH$_2$COC$_2$H$_5$ | —S—(CH$_2$)$_2$—COOH |
| 334 | 6-F 7-Cl | 8-(CH$_2$)$_2$—COC$_2$H$_5$ | —S—(CH$_2$)$_2$—COOH |
| 335 | 6-F 7-Cl | 8-(CH$_2$)$_3$—COCH$_3$ | —S—(CH$_2$)$_2$—COOH |
| 336 | 6-SCH$_3$ 7-Cl | H | —S—(CH$_2$)$_2$—COOH |
| 337 | 6-SC$_2$H$_5$ 7-Cl | H | —S—(CH$_2$)$_2$—COOH |
| 338 | 6-F 7-Cl | 8-OH | —S—(CH$_2$)$_2$—COOH |

The compound represented by the formula (I) of the present invention can be synthesized by, for example, Reaction route A, B, C, D, E, F, or G shown below.

[Reaction route A]
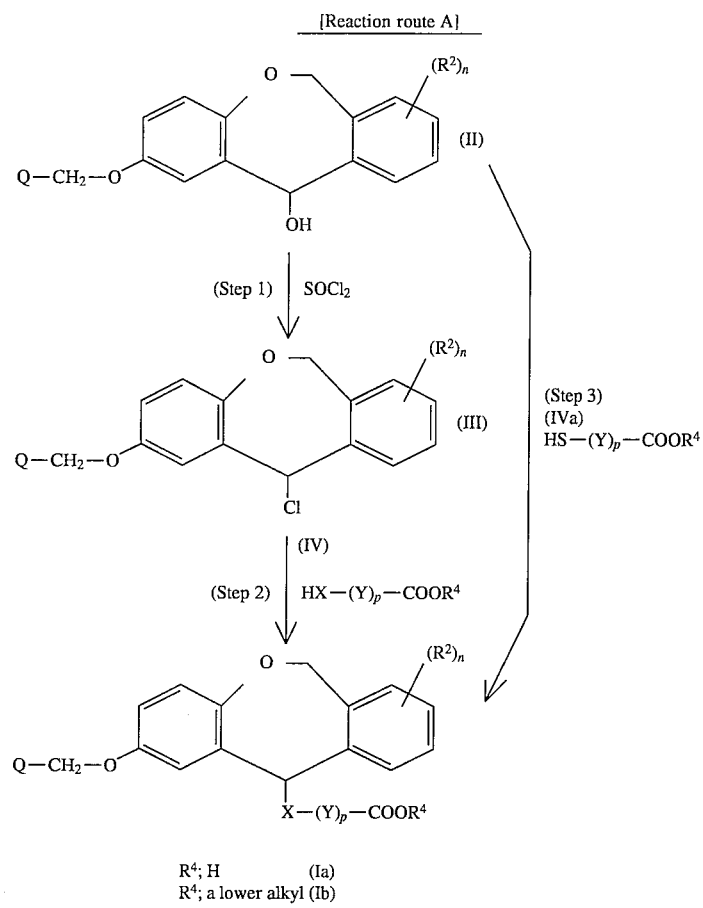
[Reaction route B]
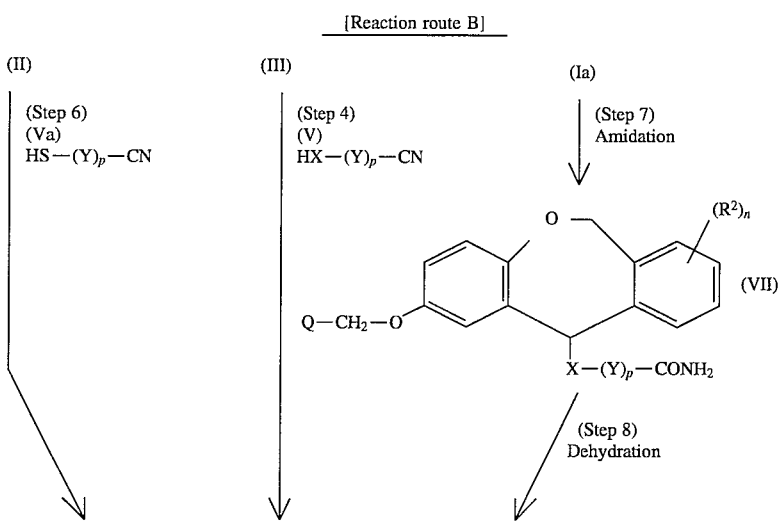

-continued
[Reaction route B]
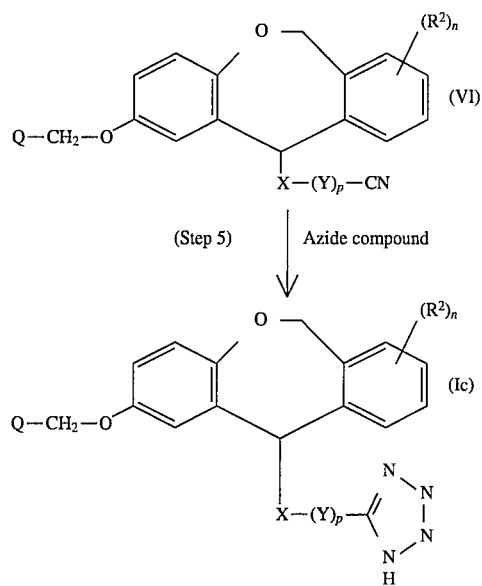
(Step 5) | Azide compound
[Reaction route C]
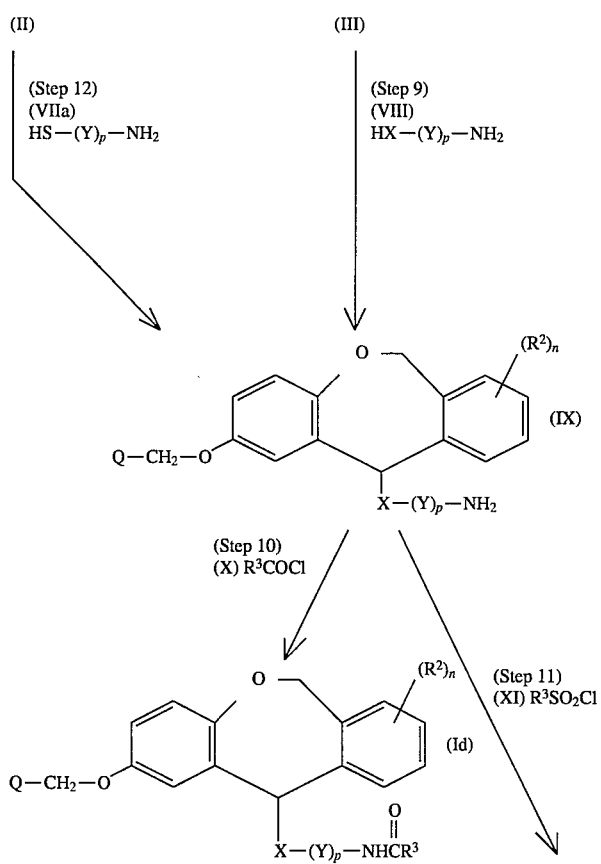

-continued
[Reaction route C]
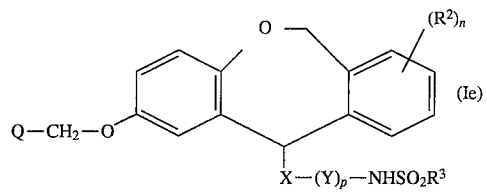
[Reaction route D]
(Step 13)   R³SO₂NH₂   (XII)
(Dehydrating agent)   or
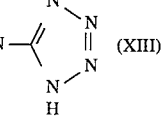
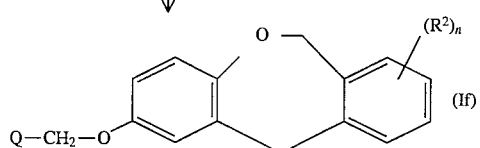
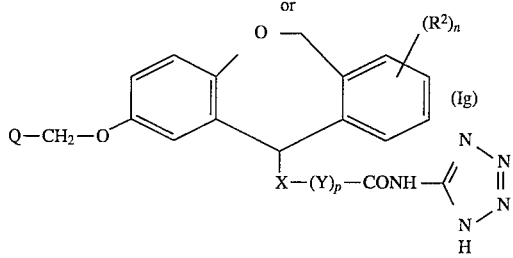
[Reaction route E]
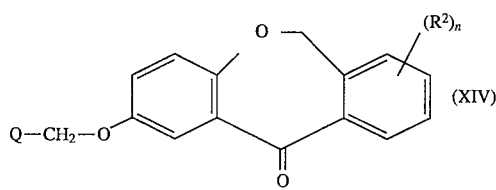
(Step 14)  NH₂OH
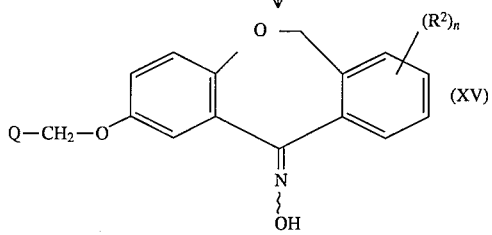
(Step 15)  Hal—(Y)$_p$—Z' (XVI)
-continued
[Reaction route E]
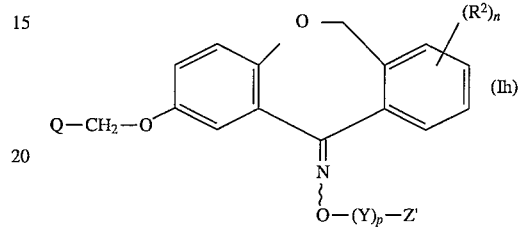
[Reaction route F]
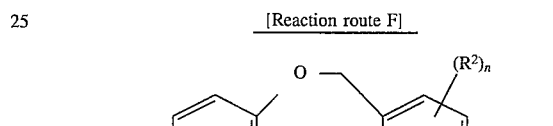
(Step 16)  $(R^5O)_2\overset{O}{\underset{\|}{P}}$—CH₂—(Y)$_p$—Z'
(XVII)
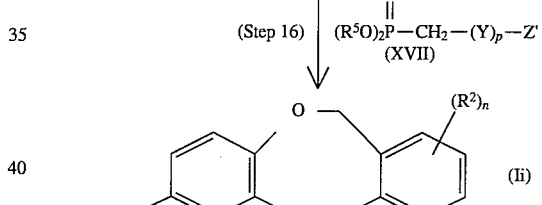
(Step 17)  Reduction
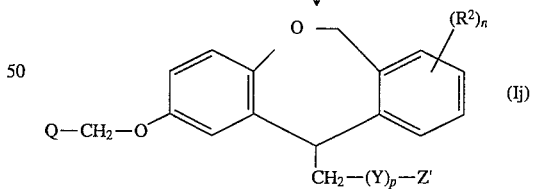
[Reaction route G]
(II)
(Step 18)  CH₃$\overset{O}{\underset{\|}{C}}$SH (Thioacetic acid)
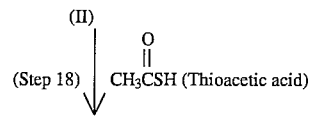

33
-continued
[Reaction route G]

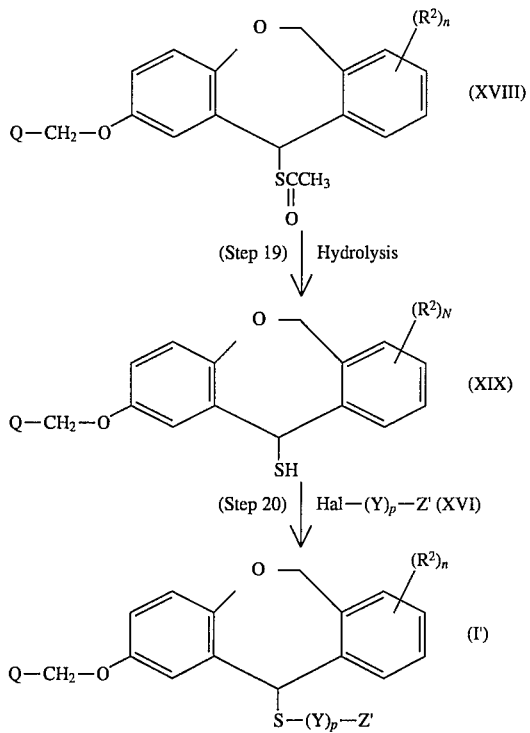

In the chemical formulae described in the above reaction routes, $R^2$, $R^3$, X, Y, n and p have the same meanings as described above, Q represents a group represented by the formula:

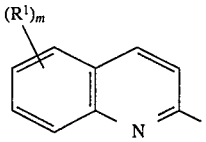

($R^1$ and m have the same meanings as described above), $R^4$ represents a hydrogen atom or a $C_1$ to $C_4$ alkyl group, $R^5$ represents a $C_1$ to $C_4$ alkyl group, Hal is an abbreviation of a halogen atom such as chlorine, bromine, iodine, etc. and Z' represents the same carboxy group, tetrazol-5-yl group, (tetrazol-5-yl)aminocarbonyl group, (tetrazol-5-yl)carbonylamino group, formula of —NH—CO—$R^3$, formula of —NH—SO$_2$—$R^3$ or formula of —CO—NH—SO$_2$—$R^3$ ($R^3$ has the same meaning as described above) as described above as to Z, or a formula of —CO—OR$^6$ ($R^6$ represents a $C_1$ to $C_4$ alkyl group).

In Step 1 of Reaction route A, the compound (III) is synthesized by reacting the compound (II) and a 1- to 10-fold molar amount, preferably a 1- to 2-fold molar amount of thionyl chloride in a solvent or in the absence of a solvent.

The solvent to be used is not particularly limited so long as it is inert to this reaction and there may be mentioned, for example, halogenated hydrocarbons such as methylene chloride, chloroform, carbon tetrachloride, dichloroethane, etc.; aromatic hydrocarbons such as benzene, toluene, etc.; and aliphatic hydrocarbons such as hexane, cyclohexane, heptane, etc.

34

The reaction temperature is 0° to 100° C., preferably in the range of 0° to 30° C. The reaction time varies depending on the above other conditions, but it is generally 5 minutes to 10 hours, preferably 30 minutes to 5 hours.

In Step 2, the compound (Ia) or the compound (Ib) is synthesized by reacting the compound (III) and a 1- to 10-fold molar amount, preferably a 1- to 5-fold molar amount of the compound (IV) in a solvent in the presence of a base.

The solvent to be used in the above reaction is not particularly limited so long as it is inert to this reaction and there may be preferred, for example, an aprotonic polar solvent such as dimethylformamide, dimethylsulfoxide, dimethylacetamide, hexamethylphosphoric acid triamide, etc.; halogenated hydrocarbons such as methylene chloride, chloroform, dichloroethane, etc.; ketones such as acetone, methyl ethyl ketone, methyl isobutyl ketone, etc.; nitriles such as acetonitrile, etc.; esters such as ethyl acetate, etc.; and ethers such as diethyl ether, diisopropyl ether, tetrahydrofuran, dioxane, etc. As the above solvent, halogenated hydrocarbons, ketones or ethers are preferred.

As the base to be used in the above Step 2, there may be mentioned, for example, an alkali metal hydride such as sodium hydride, lithium hydride, etc.; alkali metal amides such as sodium amide, etc,; amines such as triethylamine, tributylamine, diisopropylethylamine, pyridine, picoline, lutidine, 4-dimethylaminopyridine, etc.; and an alkali metal carbonate such as sodium carbonate, potassium carbonate, sodium hydrogen carbonate, etc. As the above base, the above amines are preferred. The amount of the base to be used is generally a 1- to 20-fold molar amount, preferably a 1- to 10-fold molar amount based on the compound (III).

The reaction temperature is 0° to 150° C., preferably in the range of 0° to 100° C. The reaction time varies depending on the above other conditions, but it is generally 5 minutes to 10 hours, preferably 30 minutes to 5 hours.

The compound (Ia) is also synthesized by hydrolyzing the compound (Ib) under acidic or alkaline conditions according to a conventional manner.

In Step 3, the compound (Ia) or the compound (Ib) is synthesized by reacting the compound (II) and a 1- to 5-fold molar amount, preferably a 1- to 2-fold molar amount of the compound (IVa) in a solvent in the presence of a catalyst (a dehydrating agent).

The solvent to be used in Step 3 is not particularly limited so long as it is inert to this reaction and there may be mentioned, for example, halogenated hydrocarbons such as methylene chloride, chloroform, dichloroethane, etc.; alcohols such as methanol, ethanol, propanol, isopropanol, butanol, etc.; an aprotonic polar solvent such as dimethylformamide, dimethylsulfoxide, dimethylacetamide, hexamethylphosphoric acid triamide, etc.; and ethers such as diethyl ether, diisopropyl ether, tetrahydrofuran, dioxane, etc. As the above solvent, the above halogenated hydrocarbons are preferred.

As the catalyst to be used in Step 3, there may be mentioned, for example, mineral acids such as hydrochloric acid, sulfuric acid, phosphoric acid, etc.; organic acids such as methanesulfonic acid, trifluoroacetic acid, etc.; and Lewis acids such as a boron trifluoride-diethyl ether complex, aluminum chloride, etc. The amount of the catalyst to be used is generally a 1- to 100-fold molar amount, preferably a 1- to 50-fold molar amount based on the compound (II).

The reaction temperature is 0° to 100° C., preferably in the range of 0° to 30° C. The reaction time varies depending on the above other conditions, but it is generally 5 minutes to 10 hours, preferably 30 minutes to 5 hours.

In Step 4 of Reaction route B, the reaction in which the compound (VI) is obtained from the compound (III) and the compound (V) is carried out under the same reaction conditions as described in Step 2 of Reaction route A.

In Step 5, the compound (Ic) is synthesized by reacting the compound (VI) and a 1- to 10-fold molar amount, preferably a 1- to 5-fold molar amount of the azide compound in a solvent.

As the azide compound to be used in Step 5, there may be mentioned, for example, alkali metal azides such as sodium azide, potassium azide, lithium azide, etc.; alkaline earth metal azides such as calcium azide, magnesium azide, etc.; and organic tin azides such as tri(butyl)tin azide, triphenyltin azide, etc. In said reaction, the azide compound may be used alone or may be used in combination with, for example, Lewis acids such as aluminum chloride, stannic chloride, zinc chloride, titanium chloride, a boron trifluoride-diethyl ether complex, etc.; ammonium salts such as ammonium chloride, tetramethylammonium chloride, etc.; sulfonic acids such as methanesulfonic acid, ethanesulfonic acid, etc.; alkali metal chlorides such as lithium chloride, etc.; or amine salts such as triethylamine hydrochloride, etc.

The solvent to be used in Step 5 is not particularly limited so long as it is inert to this reaction and there may be mentioned, for example, an aprotonic polar solvent such as dimethylformamide, dimethylsulfoxide, N-methylpyrrolidone, dimethylacetamide, etc.; ethers such as tetrahydrofuran, dimethoxyethane, diethoxyethane, dioxane, etc.; aromatic hydrocarbons such as benzene, toluene, xylene, etc.; and aliphatic hydrocarbons such as hexane, petroleum ether, etc.

The reaction temperature is 0° to 200° C., preferably in the range of 0° to 150° C. The reaction time varies depending on the above other conditions, but it is generally 1 to 72 hours, preferably 3 to 48 hours.

In Step 6, the reaction in which the compound (VI) is obtained from the compound (II) and the compound (Va) is carried out under the same reaction conditions as described in Step 3 of Reaction route A.

In Step 7, the compound (VII) is synthesized by subjecting a reactive derivative of the compound (Ia) in which Z in the formula (I) is a carboxy group and ammonia to amidation reaction in a solvent.

As the reactive derivative of the compound (Ia), there may be mentioned, for example, an acid halide of the compound (Ia) such as an acid bromide or acid chloride of the compound (Ia); an activated amide of the compound (Ia) obtained from the compound (Ia) and imidazole, dimethylpyrazole, triazole, etc.; and an active ester of the compound (Ia) obtained from the compound (Ia) and N-hydroxysuccinic acid imide, N-hydroxyphthalimide, 2,4,5-trichlorophenol, 2-hydroxyquinoline, etc.

The acid halide of the compound (Ia) which is a reactive derivative of the compound (Ia) can be prepared according to a conventional manner, for example, it can be synthesized by reacting the above compound (Ia) and a halide such as thionyl chloride, thionyl bromide, phosphorus pentachloride in an inert solvent.

The activated amide of the compound (Ia) which is a reactive derivative of the compound (Ia) can be also prepared according to a conventional manner. For example, in the case of a triazole amide of the compound (Ia), it can be synthesized by reacting the above compound (Ia) and 1,1'-carbonyldiimidazole in an inert solvent.

Further, the active ester of the compound (Ia) which is a reactive derivative of the compound (Ia) can be also prepared according to a conventional manner, for example, it can be synthesized by condensing a carboxylic acid derivative represented by the above compound (Ia) and hydroxy compounds such as N-hydroxysuccinic acid imide, N-hydroxyphthalimide, 2,4,5-trichlorophenol, 2-hydroxyquinoline, etc. in the presence of a condensing agent such as dicyclohexylcarbodiimide, etc. in an inert solvent.

The solvent to be used in the amidation reaction of the reactive derivative of the compound (Ia) and ammonia in Step 7 is not particularly limited so long as it is inert to this reaction and there may be mentioned, for example, aromatic hydrocarbons such as benzene, toluene, xylene, etc.; ethers such as diethyl ether, dioxane, tetrahydrofuran, etc.; halogenated hydrocarbons such as methylene chloride, chloroform, dichloroethane, etc.; alcohols such as methanol, ethanol, etc.; an aprotonic polar solvent such as dimethylformamide, dimethylsulfoxide, etc.; and water.

The reaction temperature is −80° to 150° C., preferably in the range of −50° to 100° C. The reaction time varies depending on the above other conditions, but it is generally 5 minutes to 20 hours, preferably 30 minutes to 10 hours.

In Step 8, the compound (VI) is synthesized by dehydrating the compound (VII) by using a dehydrating agent in a solvent or in the absence of a solvent.

As the dehydrating agent to be used, there may be mentioned phosphorus pentaoxide, phosphorus pentachloride, phosphorus oxychloride, phosphorus oxybromide, thionyl chloride, acetic anhydride, phosgene, chloroformic acid ethyl ester, triphenylphosphine, dicyclohexylcarbodiimide, etc.

The solvent to be used in Step 8 is not particularly limited so long as it is inert to this reaction and there may be mentioned, for example, halogenated hydrocarbons such as methylene chloride, chloroform, dichloroethane, carbon tetrachloride, etc.; an aprotonic polar solvent such as dimethylformamide, etc.; ethers such as tetrahydrofuran, dioxane, etc.; and amines such as pyridine, collidine, lutidine, etc.

The reaction temperature is 0° to 250° C., preferably in the range of 0° to 100° C. The reaction time varies depending on the above other conditions, but it is generally 5 minutes to 10 hours, preferably 30 minutes to 5 hours.

In Step 9 of Reaction route C, the reaction in which the compound (IX) is obtained from the compound (III) and the compound (VIII) is carried out under the same reaction conditions as described in Step 2 of Reaction route A.

In Step 10, the compound (Id) is synthesized by reacting the compound (IX) and a 1- to 10-fold molar amount, preferably a 1- to 5-fold molar amount of the compound (X) in a solvent in the presence of a base.

As the solvent to be used in Step 10, there may be mentioned the same solvents as described in Step 2 of Reaction route A, preferably halogenated hydrocarbons and an aprotonic polar solvent.

As the base to be used in Step 10, there may be mentioned the same bases as described in Step 2 of Reaction route A. The amount of the base to be used is generally a 1- to 10-fold molar amount, preferably a 1- to 5-fold molar amount based on the compound (IX). Further, in the reaction of this Step 10, when amines are used as a base, the reaction can be also carried out in the absence of a solvent.

The reaction temperature is 0° to 100° C., preferably in the range of 0° to 50° C. The reaction time varies depending on the above other conditions, but it is generally 5 minutes to 10 hours, preferably 30 minutes to 5 hours.

In Step 11, the reaction in which the compound (Ie) is obtained from the compound (IX) and the compound (XI) is carried out under the same reaction conditions as described in Step 10 of Reaction route C except for carrying out the reaction at a reaction temperature of −50° to 100° C., preferably in the range of −20° to 50° C.

In Step 12, the reaction in which the compound (IX) is obtained from the compound (II) and the compound (VIIIa) is carried out under the same reaction conditions as described in Step 3 of Reaction route A.

In Step 13 of Reaction route D, the compound (If) or the compound (Ig) is synthesized by reacting the compound (Ia) and a 1- to 10-fold molar amount, preferably a 1- to 5-fold molar amount of the compound (XII) or the compound (XIII) in a solvent in the presence of a condensing agent.

The solvent to be used in Step 13 is not particularly limited so long as it is inert to this reaction and may be mentioned, for example, aromatic hydrocarbons such as benzene, toluene, xylene, etc.; ethers such as diethyl ether, diisopropyl ether, tetrahydrofuran, dioxane, etc.; halogenated hydrocarbons such as methylene chloride, chloroform, dichloroethane, etc.; an aprotonic polar solvent such as dimethylformamide, dimethylsulfoxide, etc.; nitriles such as acetonitrile, etc.; and esters such as ethyl acetate, etc. As the above solvent, the above halogenated hydrocarbons and aprotonic polar solvent are preferred.

As the condensing agent to be used in Step 13, there may be mentioned dicyclohexylcarbodiimide, 1-ethyl-3-(3-dimethylaminopropyl)carbodiimide hydrochloride, 1,1'-carbonyldiimidazole, trialkyl phosphite, ethyl polyphosphate, phosphorus oxychloride, phosphorus trichloride, phosphoryl diphenylazide, diphenylphosphinic acid chloride, etc.

The reaction in Step 13 is carried out in the presence of a base, if necessary, and as an example of the base, there may be mentioned an alkali metal carbonate such as sodium carbonate, potassium carbonate, sodium hydrogen carbonate, potassium hydrogen carbonate, etc.; and amines such as triethylamine, tributylamine, diisopropylethylamine, pyridine, picoline, lutidine, 4-dimethylaminopyridine, N-methylmorpholine, etc.

The reaction temperature is 0° to 150° C., preferably in the range of 0° to 100° C. The reaction time varies depending on the above other conditions, but it is generally 10 minutes to 72 hours, preferably 30 minutes to 48 hours.

In Step 14 of Reaction route E, the compound (XV) is synthesized by reacting the compound (XIV) and a 1- to 20-fold molar amount, preferably a 1- to 15-fold molar amount of hydroxylamine hydrochloride in a solvent in the presence of a base.

The solvent to be used in Step 14 is not particularly limited so long as it is inert to this reaction and there may be mentioned, for example, an aprotonic polar solvent such as dimethylformamide, dimethylacetamide, dimethylsulfoxide, hexamethylphosphoric acid triamide, etc.; and alcohols such as methanol, ethanol, propanol, isopropanol, butanol, etc.

As the base to be used in Step 14, there may be mentioned, for example, an alkali metal hydroxide such as sodium hydroxide, potassium hydroxide, etc.; an alkali metal carbonate such as sodium carbonate, potassium carbonate, sodium hydrogen carbonate, potassium hydrogen carbonate, etc.; and amines such as pyridine, collidine, lutidine, etc. As the above base, the above amines are preferred.

The reaction temperature is 20° to 300° C., preferably in the range of 50° to 200° C. The reaction time varies depending on the above other conditions, but it is generally 15 minutes to 72 hours, preferably 1 to 48 hours.

In Step 15, the compound (Ih) is synthesized by subjecting the compound (XV) and a 1- to 10-fold molar amount, preferably a 1- to 5-fold molar amount of the compound (XVI) to condensation reaction in a solvent in the presence of a base.

As the solvent to be used, there may be mentioned the same solvents as described in Step 2 of Reaction route A, particularly preferably ketones and an aprotonic polar solvent.

As the base to be used in Step 15, there may be mentioned the same bases as described in Step 2 of Reaction route A, particularly preferably an alkali metal hydride and an alkali metal carbonate.

The amount of the above base to be used and the reaction conditions such as reaction temperature, reaction time, etc. are the same as described in Step 2 of Reaction route A.

In Step 16 of Reaction route F, the compound (Ii) is synthesized by reacting the compound (XIV) and a 1- to 10-fold molar amount, preferably a 1- to 5-fold molar amount of an anion of the compound (XVII) in a solvent.

The anion of the compound (XVII) is produced by treating the compound (XVII) with a base. As the base to be used in the above anion-producing reaction, there may be mentioned, for example, an alkali metal hydride such as sodium hydride, lithium hydride, etc., alkali metal alkoxides such as sodium methoxide, sodium ethoxide, potassium t-butoxide, etc., alkyl lithiums such as methyl lithium, butyl lithium, etc. and metal amides such as sodium amide, lithium diisopropylamide, etc., particularly preferably an alkali metal hydride.

The solvent to be used in Step 16 is not particularly limited so long as it is inert to this reaction and there may be mentioned, for example, aromatic hydrocarbons such as benzene, toluene, etc.; ethers such as tetrahydrofuran, dioxane, dimethoxyethane, diethoxyethane, etc.; and an aprotonic polar solvent such as dimethylformamide, dimethylacetamide, dimethylsulfoxide, etc. As the above solvent, ethers are preferred.

The reaction in which the anion of the compound (XVII) is produced is preferably carried out at −50° to 100° C., particularly in the range of −10° to 50° C. Further, the reaction of the anion of the compound (XVII) produced in the above reaction and the compound (XIV) is preferably carried out at 0° to 300° C., particularly in the range of 50° to 200° C. It is preferred that the reaction time of the reaction in which the anion of the compound (xVII) is produced is 30 minutes to 3 hours, and that of the reaction of the compound (XIV) and the anion of the compound (XVII) is 30 minutes to 48 hours.

In Step 17, the compound (Ij) is synthesized by subjecting the compound (Ii) to catalytic reduction with hydrogen in the presence of a catalyst.

The solvent to be used in Step 17 is not particularly limited so long as it is inert to this reaction and there may be mentioned, for example, alcohols such as methanol, ethanol, etc. and ethers such as dioxane, tetrahydrofuran, etc. As the above solvent, the above alcohols are preferred.

As the catalyst to be used in Step 17, there may be mentioned, for example, palladium-carbon, platinum black and rhodium-carbon. The hydrogen partial pressure in the reaction of Step 17 is preferably 1 to 10 atmospheric pressure, particularly 1 to 3 atmospheric pressure.

The reaction temperature is preferably 0° to 100° C., particularly in the range of 20° to 80° C. The reaction time varies depending on the above other conditions, but it is generally preferably 15 minutes to 10 hours, particularly 30 minutes to 5 hours.

In Step 18 of Reaction route G, the reaction in which the compound (XVIII) is obtained from the compound (II) and thioacetic acid is carried out under the same reaction conditions as described in Step 3 of Reaction route A.

In Step 19, the compound (XIX) is obtained by hydrolyzing the compound (XVIII) under alkaline conditions according to a conventional manner.

In Step 20, the reaction in which the compound (I') is obtained from the compound (XIX) and the compound (XVI) is carried out under the same reaction conditions as described in Step 15 of Reaction route E.

Among the compounds represented by the formula (I), a compound in which $R^2$ or Z is a group containing a tetrazol-5-yl group is synthesized from a corresponding cyano compound under the same reaction conditions as described in Step 5 of Reaction route B.

A cyano group, a carbamoyl group, a carboxy group and a protected carboxy group contained in a molecule of the compound (I) are mutually converted according to a conventional manner as shown in the following formula:

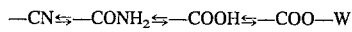

(W represents the protective group described above).

In this mutual conversion reaction, conversion from a carboxylic acid (—COOH) to an amide (—CONH$_2$) and conversion from the amide to a cyano (—CN) are carried out in the same manner as described in Step 7 and Step 8 of Reaction route B, respectively.

The compounds (IV), (V), (VIII), (X), (XI), (XII), (XIII), (XVI), (XVII) and other subsidiary starting materials used in the above Reaction routes A, B, C, D, E, F and G are all known compounds. Further, the compounds (II) and (XIV) are easily prepared according to Reaction route H shown below.

[Reaction route H]

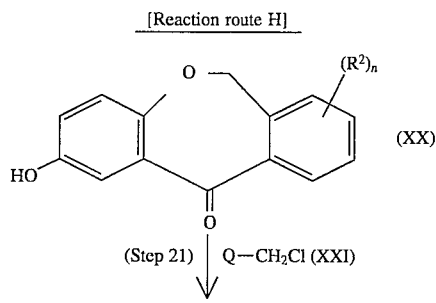

-continued
[Reaction route H]

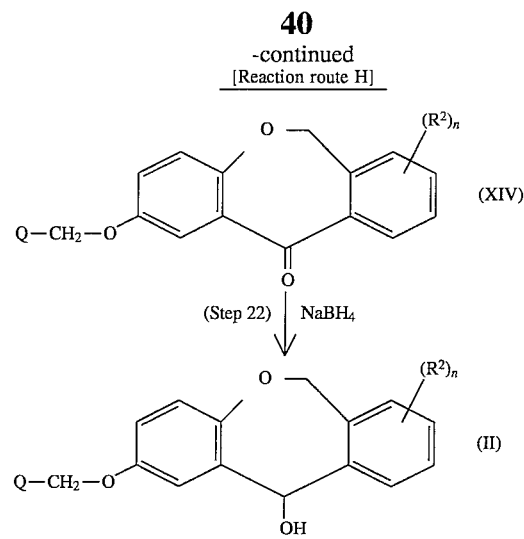

(in the chemical formulae in the above reaction route, $R^2$, n and Q have the same meanings as described above)

In Step 21 of Reaction route H, the reaction in which the compound (XIV) is obtained from the compound (XX) and the compound (XXI) is carried out under the same reaction conditions as described in Step 15 of Reaction route E.

In Step 22, the reduction reaction from the compound (XIV) to the compound (II) is carried out by a known method, for example, a method of reducing with sodium boron hydride in ethanol or methanol, etc.

The compound (XX) and the compound (XXI) to be used as starting materials in Reaction route H are prepared by a combination of a conventional manner and a known published method, for example, according to Reaction routes I and J shown below, respectively.

[Reaction route I]

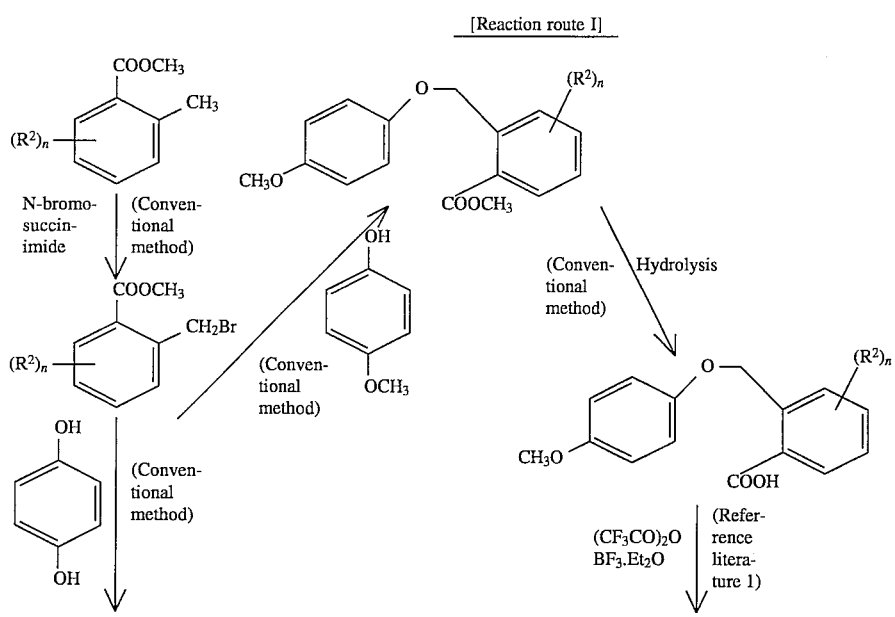

-continued
[Reaction route I]

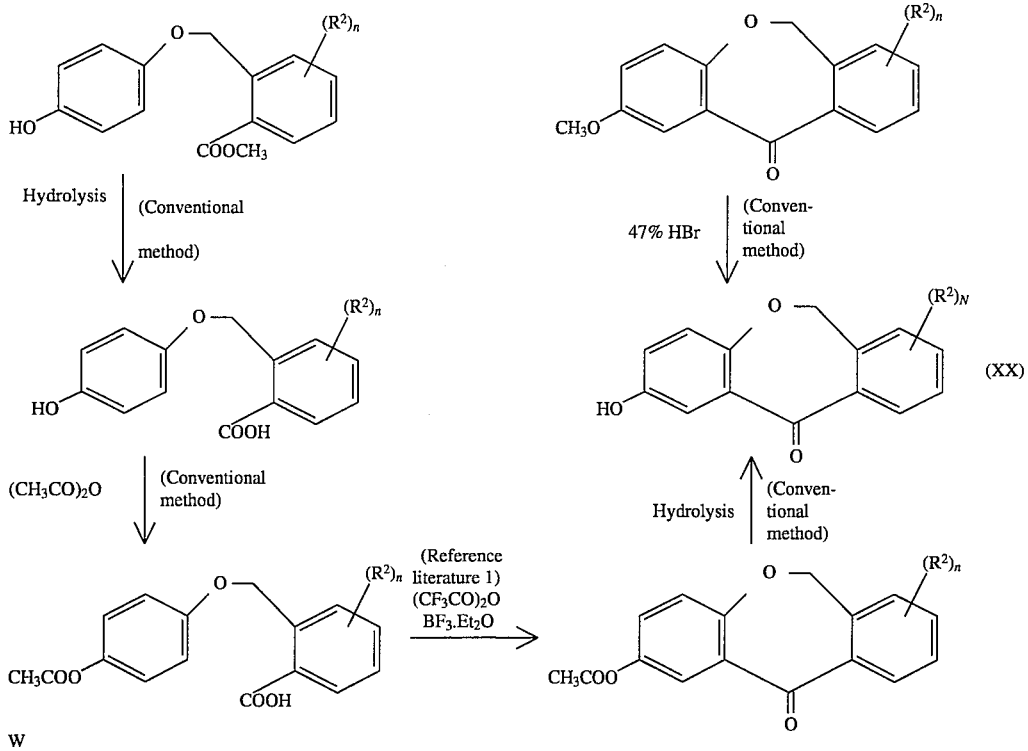

(in the chemical formulae in the above reaction route, $R^2$ and n have the same meanings as described above, and "Et" is an abbreviation of an ethyl group.)

(Reference literature 1) Chem. Pharm. Bull., 39, 2564 (1991)

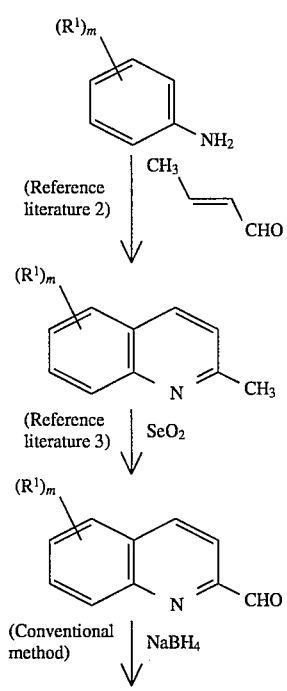

-continued
[Reaction route J]

(in the chemical formulae in the above reaction route, $R^1$ and m have the same meanings as described above.)

(Reference literature 2) J. Org. Chem., 42, 911 (1977)
(Reference literature 3) Chem. Pharm. Bull., 32, 4914 (1984)

After completion of the reactions, the desired compounds of the respective reactions can be obtained by treating the reaction mixtures according to a conventional manner and further purified by a common purification means such as recrystallization, column chromatography, etc., if necessary. Further, the compound of the formula (I) of the present invention is converted into a desired salt according to a conventional manner, if necessary.

In the compound of the formula (I) thus prepared, an optical isomer or a geometric (cis, trans or E, Z) isomer may exist. In such a case, if desired, an optical isomer or a geometric isomer of a corresponding desired compound can be obtained by carrying out the above reaction by using an optically resolved or separated starting compound. Also, a mixture of an optical isomer or a geometric isomer is treated according to a common optical resolution method or separation method to obtain the respective isomers.

In the formula (I), all of an optical isomer, a geometric isomer and a mixture thereof are represented by a single formula, but the present invention includes the respective isomers and a mixture thereof as a matter of course.

BEST MODE FOR CARRYING OUT THE INVENTION

In the following, the present invention is described in detail by referring to Examples, but the scope of the present invention is not limited thereby.

EXAMPLE 1

11-(2-Carboxyethylthio)-2-(7-chloro-6-fluoroquinolin-2-yl)methoxy-6,11-dihydrodibenz[b,e]oxepine: (Exemplary compound 262)

While stirring under ice cooling, 1 g of 2-(7-chloro-6-fluoroquinolin-2-yl)methoxy-11-hydroxy-6,11-dihydrodibenz[b,e]oxepine was added to a mixed solution of 8 ml of trifluoroacetic acid and 6 ml of methylene chloride, then 0.25 g of 3-mercaptopropionic acid was added to the solution and the mixture was stirred under ice cooling for 2 hours. After completion of the reaction, 180 ml of ice water was added the mixture, the mixture was adjusted to about pH 3 with a 1N-sodium hydroxide aqueous solution and then the aqueous layer was extracted with 200 ml of methylene chloride. The organic layer was washed with water and dried over anhydrous sodium sulfate and the residue obtained by removing the solvent under reduced pressure was recrystallized from ethyl acetate to obtain 0.63 g of the title compound as white powder.

m.p. 180° to 183° C.

$^1$H NMR ($\delta$, CDCl$_3$-DMSO-d$_6$); 2.42 (2H, t), 2.55 to 2.75 (2H, m), 4.83 (1H, d), 5.00 (1H, s), 5.28 (2H, s), 6.06 (1H, d), 6.77 (1H, d), 6.83 (1H, dd), 6.95 (1H, d), 7.25 to 7.35 (4H, m), 7.67 (1H, d), 7.70 (1H, d), 8.14 (1H, d), 8.23 (1H, d), 11.80 to 12.20 (1H, br. s)

EXAMPLE 2

11-(2-Carboxyethylthio)-2-(7-chloroquinolin-2-yl)methoxy-6,11-dihydrodibenz[b,e]oxepine: (Exemplary compound 182)

2-(7-Chloroquinolin-2-yl)methoxy-11-hydroxy-6,11-dihydrodibenz[b,e]oxepine and 3-mercaptopropionic acid were used and reacted in the same manner as in Example 1 to obtain the title compound.

Yellowish white powder m.p. 169° to 172° C. (decomposed)

$^1$H NMR ($\delta$, CDCl$_3$-DMSO-d$_6$); 2.43 (2H, t), 2.55 to 2.70 (2H, m), 4.84 (1H, d), 4.99 (1H, s), 5.31 (2H, s), 6.07 (1H, d), 6.78 (1H, d), 6.84 (1H, dd), 6.95 (1H, d), 7.25 to 7.35 (4H, m), 7.52 (1H, dd), 7.69 (1H, d), 7.85 (1H, d), 8.05 (1H, s), 8.25 (1H, d)

EXAMPLE 3

11-(2-Carboxyethylthio)-2-(6-fluoroquinolin-2-yl)methoxy-6,11-dihydrodibenz[b,e]oxepine: (Exemplary compound 230)

2-(6-Fluoroquinolin-2-yl)methoxy-11-hydroxy-6,11-dihydrodibenz[b,e]oxepine and 3-mercaptopropionic acid were used and reacted in the same manner as in Example 1 to obtain the title compound.

White powder m.p. 167° to 171° C.

$^1$H NMR ($\delta$, CDCl$_3$-DMSO-d$_6$); 2.42 (2H, t), 2.59 to 2.71 (2H, m), 4.84 (1H, d), 5.02 (1H, s), 5.30 (2H, s), 6.06 (1H, d), 6.77 (1H, d), 6.85 (1H, dd), 6.97 (1H, d), 7.27 to 7.35 (4H, m), 7.32 to 7.51 (4H, m), 7.51 to 7.55 (2H, m), 7.70 (1H, d), 8.05 (1H, dd), 8.24 (1H, d)

EXAMPLE 4

11-(2-Carboxyethylthio)-2-(7-fluoroquinolin-2-yl)methoxy-6,11-dihydrodibenz[b,e]oxepine: (Exemplary compound 233)

2-(7-Fluoroquinolin-2-yl)methoxy-11-hydroxy-6,11-dihydrodibenz[b,e]oxepine and 3-mercaptopropionic acid were used and reacted in the same manner as in Example 1 to obtain the title compound.

White powder m.p. 161° to 163° C.

$^1$H NMR ($\delta$, CDCl$_3$-DMSO-d$_6$); 2.46 (2H, t), 2.62 to 2.74 (2H, m), 4.88 (1H, d), 5.06 (1H, s), 5.34 (2H, s), 6.10 (1H, d), 6.82(1H, d), 6.89 (1H, dd), 7.01 (1H, d), 7.30 to 7.34 (3H, m), 7.39 to 7.44 (1H, m), 7.70 (1H, m), 7.96 (1H, dd), 8.32 (1H, d)

EXAMPLE 5

11-(2-Carboxyethylthio)-2-(6-chloroquinolin-2-yl)methoxy-6,11-dihydrodibenz[b,e]oxepine: (Exemplary compound 232)

2-(6-Chloroquinolin-2-yl)methoxy-11-hydroxy-6,11-dihydrodibenz[b,e]oxepine and 3-mercaptopropionic acid were used and reacted in the same manner as in Example 1 to obtain the title compound.

Orange-tinged white powder m.p. 178° to 180° C.

$^1$H NMR ($\delta$, CDCl$_3$-DMSO-d$_6$); 2.43 (2H, t), 2.61 to 2.72 (2H, m), 4.84 (1H, d), 5.01 (1H, s), 5.30 (2H, s), 6.06 (1H, d), 6.78 (1H, d), 6.84 (1H, dd), 6.96 (1H, d), 7.15 to 7.34 (4H, m), 7.67 (1H, dd), 7.71 (1H, d), 7.89 (1H, d), 8.01 (1H, d), 8.21 (1H, d)

EXAMPLE 6

11-(2-Carboxyethylthio)-2-(7-difluoromethoxyquinolin-2-yl)methoxy-6,11-dihydrodibenz[b,e]oxepine: (Exemplary compound 236)

2-(7-Difluoromethoxyquinolin-2-yl)methoxy-11-hydroxy-6,11-dihydrodibenz[b,e]oxepine and 3-mercaptopropionic acid were used and reacted in the same manner as in Example 1 to obtain the title compound.

White powder m.p. 180° to 184° C.

$^1$H NMR (δ, CDCl$_3$-DMSO-d$_6$); 2.41 (2H, t), 2.55 to 2.75 (2H, m), 4.83 (1H, d), 5.02 (1H, s), 5.30 (2H, s), 6.06 (1H, d), 6.77 (1H, d), 6.85 (1H, dd), 7.03 (1H, s), 7.09 (1H, d), 7.25 to 7.35 (4H, m), 7.39 (1H, dd), 7.66 (1H, d), 7.72 (1H, d), 7.92 (1H, d), 8.27 (1H, d), 11.80 to 12.20 (1H, br. s)

EXAMPLE 7

11-(2-Carboxyethylthio)-2-(8-fluoroquinolin-2-yl)methoxy-6,11-dihydrodibenz[b,e]oxepine: (Exemplary compound 234)

2-(8-Fluoroquinolin-2-yl)methoxy-11-hydroxy-6,11-dihydrodibenz[b,e]oxepine and 3-mercaptopropionic acid were used and reacted in the same manner as in Example 1 to obtain the title compound.

(as ¾ H$_2$O adduct)

Yellowish white powder m.p. 185° to 188° C.

$^1$H NMR (δ, CDCl$_3$-DMSO-d$_6$); 2.43 (2H, t), 2.55 to 2.75 (2H, m), 4.84 (1H, d), 5.02 (1H, s), 5.35 (2H, s), 6.07 (1H, d), 6.78 (1H, d), 6.85 (1H, dd), 6.98 (1H, d), 7.25 to 7.35 (H, m), 7.40 to 7.55 (2H, m), 7.69 (1H, d), 7.77 (1H, d), 8.30 (1H, dd), 11.80 to 12.20 (1H, br. s)

EXAMPLE 8

11-(2-Carboxyethylthio)-2-(5,7-dichloroquinolin-2-yl)-methoxy-6,11-dihydrodibenz[b,e]oxepine: (Exemplary compound 235)

2-(5,7-Dichloroquinolin-2-yl)methoxy-11-hydroxy-6,11-dihydrodibenz[b,e]oxepine and 3-mercaptopropionic acid were used and reacted in the same manner as in Example 1 to obtain the title compound.

Orange-tinged white powder m.p. 183° to 185° C. (decomposed)

$^1$H NMR (δ, CDCl$_3$-DMSO-d$_6$); 2.43 (2H, t), 2.60 to 2.73 (2H, m), 4.84 (1H, d), 5.02 (1H, s), 5.32 (2H, s), 6.07 (1H, d), 6.78 (1H, d), 6.84 (1H, dd), 6.97 (1H, d), 7.27 to 7.32 (4H, m), 7.66 (1H, d), 7.81 (1H, d), 8.00 (1H, d), 8.57 (1H, d)

EXAMPLE 9

11-(2-Carboxyethylthio)-2-(6-ethylquinolin-2-yl)methoxy-6,11-dihydrodibenz[b,e]oxepine: (Exemplary compound 231)

2-(6-Ethylquinolin-2-yl)methoxy-11-hydroxy-6,11-dihydrodibenz[b,e]oxepine and 3-mercaptopropionic acid were used and reacted in the same manner as in Example 1 to obtain the title compound.

(as H$_2$O adduct)

White powder $^1$H NMR (δ, CDCl$_3$-DMSO-d$_6$); 1.34 (3H, t), 2.42 (2H, t), 2.55 to 2.75 (2H, m), 4.85 (2H, q), 4.83 (1H, d), 5.01 (1H, s), 5.29 (2H, s), 6.06 (1H, d), 6.77 (1H, d), 6.84 (1H, dd), 6.97 (1H, d), 7.25 to 7.35 (4H, m), 7.55 to 7.65 (3H, m), 7.96 (1H, d), 8.18 (1H, d)

EXAMPLE 10

11-(2-Carboxyethylthio)-2-(6-methoxyquinolin-2-yl)methoxy-6,11-dihydrodibenz[b,e]oxepine: (Exemplary compound 229)

11-Hydroxy-2-(6-methoxyquinolin-2-yl)methoxy-6,11-dihydrodibenz[b,e]oxepine and 3-mercaptopropionic acid were used and reacted in the same manner as in Example 1 to obtain the title compound.

White powder m.p. 174° to 175° C.

$^1$H NMR (δ, CDCl$_3$-DMSO-d$_6$); 2.43 (2H, t), 2.59 to 2.72 (2H, m), 4.83 (1H, d), 4.99 (1H, s), 5.28 (2H, s), 6.06 (1H, d), 6.78 (1H, d), 6.84 (1H, dd), 6.95 (1H, d), 7.15 (1H, d), 7.24 to 7.33 (4H, m), 7.38 (1H, dd), 7.62 (1H, d), 7.95 (1H, d), 8.15 (1H, d)

EXAMPLE 11

11-(2-Carboxyethylthio)-2-(quinolin-2-yl)methoxy-6,11-dihydrodibenz[b,e]oxepine: (Exemplary compound 122) (as ¼ H$_2$O adduct)

11-Hydroxy-2-(quinolin-2-yl)methoxy-6,11-dihydrodibenz[b,e]oxepine and 3-mercaptopropionic acid were used and reacted in the same manner as in Example 1 to obtain the title compound.

Orange-tinged white powder m.p. 186° to 190° C.

$^1$H NMR (δ, CDCl$_3$-DMSO-d$_6$); 2.41 (2H, t), 2.57 to 2.66 (2H, m), 4.84 (1H, d), 5.09 (1H, s), 5.30 (2H, s), 6.04 (1H, d), 6.76 (1H, d), 6.86 (1H, dd), 7.02 (1H, d), 7.32 (4H, m), 7.58 (1H, d), 7.65 to 7.74 (2H, m), 7.90 (1H, d), 8.03 (1H, d), 8.29 (1H, d)

EXAMPLE 12

11-(2-Carboxyethylthio)-2-(7-chloroquinolin-2-yl)methoxy-10-methyl-6,11-dihydrodibenz[b,e]oxepine: (Exemplary compound 239)

2-(7-Chloroquinolin-2-yl)methoxy-11-hydroxy-10-methyl-6,11-dihydrodibenz[b,e]oxepine and 3-mercaptopropionic acid were used and reacted in the same manner as in Example 1 to obtain the title compound.

(as ¼ H$_2$O adduct)

White powder m.p. 184° to 185° C. (decomposed) $^1$H NMR (δ, CDCl$_3$-DMSO-d$_6$); 2.44 (2H, t), 2.47 (3H, s), 2.69 (2H, t), 4.77 (1H, d), 5.31 (1H, d), 5.32 (2H, s), 6.17 (1H, d), 6.78 (1H, d), 6.84 (1H, dd), 6.97 (1H, d), 7.12 (1H, dd), 7.12 (2H, m), 7.53 (1H, dd), 7.69 (1H, d), 7.85 (1H, d), 8.03 (1H, d), 8.28 (1H, d)

EXAMPLE 13

11-(2-Carboxyethylthio)-2-(7-chloroquinolin-2-yl)methoxy-8-methoxy-6,11-dihydrodibenz[b,e]oxepine: (Exemplary compound 237)

2-(7-Chloroquinolin-2-yl)methoxy-11-hydroxy-8-methoxy-6,11-dihydrodibenz[b,e]oxepine and 3-mercaptopropionic acid were used and reacted in the same manner as in Example 1 to obtain the title compound.

Slightly yellow needle crystals m.p. 177° to 179° C. $^1$H NMR ($\delta$, CDCl$_3$-DMSO-d$_6$); 2.44 (2H, t), 2.55 to 2.75 (2H, m), 3.81 (3H, s), 4.78 (1H, d), 4.96 (1H, s), 5.31 (2H, s), 6.03 (1H, d), 6.75 to 6.85 (4H, m), 6.92 (1H, d), 7.17 (1H, d), 7.50 to 7.55 (1H, m), 7.69 (1H, d), 7.82 (1H, d), 8.05 (1H, s), 8.23 (1H, d), 11.80 to 12.10 (1H, br. s)

EXAMPLE 14

8-Bromo-11-(2-carboxyethylthio)-2-(7-chloroquinolin-2-yl)-methoxy-6,11-dihydrodibenz[b,e]oxepine: (Exemplary compound 238)

8-Bromo-2-(7-chloroquinolin-2-yl)methoxy-11-hydroxy-6,11-dihydrodibenz[b,e]oxepine and 3-mercaptopropionic acid were used and reacted in the same manner as in Example 1 to obtain the title compound.

White needle crystals m.p. 181° to 182.5° C.

$^1$H NMR ($\delta$, CDCl$_3$-DMSO-d$_6$); 2.47 (2H, t), 2.55 to 2.75 (2H, m), 4.80 (1H, d), 4.98 (1H, s), 5.31 (2H, s), 5.98 (1H, d), 6.75 to 6.90 (2H, m), 6.94 (1H, d), 7.17 (1H, d), 7.35 to 7.45 (2H, m), 7.50 to 7.55 (1H, m), 7.68 (1H, d), 7.83 (1H, d), 7.05 (1H, d), 8.24 (1H, d), 11.90 to 12.20 (1H, br. s)

EXAMPLE 15

11-(2-Carboxyethylthio)-2-(7-Chloroquinolin-2-yl)methoxy-7-cyano-6,11-dihydrodibenz[b,e]oxepine: (Exemplary compound 240)

2-(7-Chloroquinolin-2-yl)methoxy-7-cyano-11-hydroxy-6,11-dihydrodibenz[b,e]oxepine and 3-mercaptopropionic acid were used and reacted in the same manner as in Example 1 to obtain the title compound.

Slightly yellow powder m.p. 193° to 195° C.

$^1$H NMR ($\delta$, CDCl$_3$-DMSO-d$_6$); 2.50 (2H, t), 2.55 to 2.80 (2H, m), 5.06 (1H, s), 5.25 (1H, d), 5.38 (2H, s), 6.05 (1H, d), 6.89 (2H, s), 6.96 (1H, s), 7.41 (1H, t), 7.55 (1H, dd), 7.63 (1H, d), 7.73 (1H, d), 7.85 (1H, d), 8.14 (1H, s), 8.30 (1H, d)

EXAMPLE 16

11-(2-Carboxyethylthio)-8-carboxymethylthio-2-(7-chloroquinolin-2-yl)methoxy-6,11-dihydrodibenz[b,e]oxepine: (Exemplary compound 260)

8-carboxymethylthio-2-(7-chloroquinolin-2-yl)methoxy-11-hydroxy-6,11-dihydrodibenz[b,e]oxepine and 3-mercaptopropionic acid were used and reacted in the same manner as in Example 1 to obtain the title compound.

Brown powder m.p. 165° to 167° C.

$^1$H NMR ($\delta$, CDCl$_3$-DMSO-d$_6$); 2.47 (2H, t), 2.55 to 2.75 (2H, m), 3.66 (2H, s), 4.80 (1H, d), 4.94 (1H, s), 5.32 (2H, s), 5.99 (1H, d), 6.75 to 6.90 (2H, m), 6.92 (1H, d), 7.18 (1H, d), 7.25 to 7.35 (2H, m), 7.52 (1H, dd), 7.69 (1H, d), 7.82 (1H, d), 8.07 (1H, s), 8.23 (1H, d)

EXAMPLE 17

11-(2-Carboxyethylthio)-2-(quinolin-2-yl)methoxy-8-(tetrazol-5-yl)-6,11-dihydrodibenz[b,e]oxepine: (Exemplary compound 180)

11-Hydroxy-2-(quinolin-2-yl)methoxy-8-(tetrazol-5-yl)-6,11-dihydrodibenz[b,e]oxepine and 3-mercaptopropionic acid were used and reacted in the same manner as in Example 1 to obtain the title compound.

(as ½ H$_2$O adduct)

Light brown powder m.p. 151° to 153° C.

$^1$H NMR ($\delta$, CDCl$_3$-DMSO-d$_6$); 2.48 (2H, t), 2.55 to 2.80 (2H, m), 4.94 (1H, d), 5.07 (1H, s), 5.35 (2H, s), 6.07 (1H, d), 6.83 (1H, d), 6.88 (1H, dd), 6.99 (1H, d), 7.43 (1H, d), 7.58 (1H, t), 7.69 (1H, d), 7.76 (1H, td), 7.87 (1H, d), 8.02 (1H, d), 8.03 (1H, s), 8.08 (1H, d), 8.26 (1H, d)

EXAMPLE 18

11-(2-Carboxyethylthio)-2-(7-chloroquinolin-2-yl)methoxy-8-(tetrazol-5-yl)-6,11-dihydrodibenz[b,e]oxepine: (Exemplary compound 243)

2-(7-Chloroquinolin-2-yl)methoxy-11-hydroxy-8-(tetrazol-5-yl)-6,11-dihydrodibenz[b,e]oxepine and 3-mercaptopropionic acid were used and reacted in the same manner as in Example 1 to obtain the title compound.

Brown powder m.p. 170° to 172° C.

$^1$H NMR ($\delta$, CDCl$_3$-DMSO-d$_6$); 2.49 (2H, t), 2.55 to 2.95 (2H, m), 4.94 (1H, d), 5.06 (1H, s), 5.32 (2H, s), 6.08 (1H, s), 6.80 to 6.90 (2H, m), 6.97 (1H, d), 7.42 (1H, d), 7.52 (1H, dd), 7.69 (1H, d), 7.83 (1H, d), 8.00 to 8.10 (3H, m), 8.23 (1H, d)

EXAMPLE 19

11-(2-Carboxyethylthio)-2-(7-chloroquinolin-2-yl)methoxy-7-(tetrazol-5-yl)-6,11-dihydrodibenz[b,e]oxepine: (Exemplary compound 242)

2-(7-Chloroquinolin-2-yl)methoxy-11-hydroxy-7-(tetrazol-5-yl)-6,11-dihydrodibenz[b,e]oxepine and 3-mercaptopropionic acid were used and reacted in the same manner as in Example 1 to obtain the title compound.

Slightly yellow powder m.p. 122° to 125° C.

$^1$H NMR ($\delta$, CDCl$_3$-DMSO-d$_6$); 2.53 (2H, t), 2.60 to 2.80 (2H, m), 5.11 (1H, s), 5.43 (2H, s), 5.67 (1H, d), 6.07 (1H, d), 6.75 to 6.90 (2H, m), 6.99 (1H, d), 7.40 to 7.45 (2H, m), 7.58 (1H, dd), 7.66 (1H, t), 7.78 (1H, d), 7.88 (1H, d), 8.23 (1H, s), 8.36 (1H, d)

EXAMPLE 20

7-Carbamoyl-11-(2-carboxyethylthio)-2-(7-chloroquinolin-2-yl)methoxy-6,11-dihydrodibenz[b,e]oxepine: (Exemplary compound 241)

40 ml of a 1N-sodium hydroxide aqueous solution was added to 0.85 g of the compound 11-(2-carboxyethylthio)-2-(7-chloroquinolin-2-yl)methoxy-7-cyano-6,11-dihydrodibenz[b,e]oxepine obtained in Example 15 dissolved in 10 ml of ethanol and the mixture was refluxed under heating for 2 hours. After completion of the reaction, water was added to the residue obtained by removing the solvent, the mixture was adjusted to about pH 3 with 1N-hydrochloric acid and crystals precipitated were dissolved in ethyl acetate. The organic layer was washed with water, dried over anhydrous sodium sulfate and condensed. The resulting residue was applied to silica gel column chromatography to obtain 0.25 g of the title compound as slightly yellow powder.

(as ¼ $H_2O$ adduct)

m.p. 187° to 189° C.

$^1$H NMR ($\delta$, $CDCl_3$-DMSO-$d_6$); 2.47 (2H, t), 2.55 to 2.75 (2H, m), 5.07 (1H, s), 5.37 (2H, s), 5.39 (1H, d), 6.02 (1H, d), 6.75 to 6.90 (3H, m), 6.97 (1H, d), 7.33 (1H, d), 7.40 to 7.50 (2H, m), 7.57 (1H, dd), 7.75 (1H, d), 7.90 (1H, d), 8.14 (1H, s), 7.35 (1H, d)

EXAMPLE 21

11-Carboxymethylthio-2-(7-chloroquinolin-2-yl) methoxy-6,11-dihydrodibenz[b,e]oxepine: (Exemplary compound 181)

While stirring under ice cooling, 0.34 ml of thionyl chloride was added to 1.88 g of 2-(7-chloroquinolin-2-yl)methoxy-11-hydroxy-6,11-dihydrodibenz[b,e]oxepine dissolved in 21 ml of methylene chloride and the mixture was stirred at the same temperature for 30 minutes to produce 11-chloro-2-(7-chloroquinolin-2-yl)methoxy-6,11-dihydrodibenz[b,e]oxepine. After the solvent was removed from the reaction mixture, the residue was dissolved in 20 ml of methylene chloride, 1.25 ml of triethylamine and 1.69 ml of methyl thioglycolate were added to the solution while stirring under ice cooling and the mixture was stirred at room temperature for 7 hours. After the solvent was removed from the reaction mixture, 60 ml of ethanol and 45 ml of a 1N-sodium hydroxide aqueous solution were added to the residue and the mixture was stirred at room temperature for 1 hour. After the solvent was removed, 150 ml of ice water was added to the residue, the mixture was adjusted to about pH 2 with 1N-hydrochloric acid and then the aqueous layer was extracted with 150 ml of methylene chloride. After the organic layer was washed with water, the residue obtained by removing the solvent was applied to silica gel column chromatography to obtain 0.54 g of the title compound as white powder.

m.p. 179° to 181° C.

$^1$H NMR ($\delta$, $CDCl_3$-DMSO-$d_6$); 3.03 (2H, s), 4.85 (1H, d), 5.26 (1H, d), 5.30 (2H, s), 6.02 (1H, s), 6.80 (1H, d), 6.86 (1H, dd), 7.01 (1H, d), 7.27 to 7.34 (4H, m), 7.52 (1H, dd), 7.86 (1H, d), 8.03 (1H, d), 8.26 (1H, d)

EXAMPLE 22

11-Carboxymethylthio-2-(quinolin-2-yl)methoxy-6,11-dihydrodibenz[b,e]oxepine: (Exemplary compound 121)

11-Hydroxy-2-(quinolin-2-yl)methoxy-6,11-dihydrodibenz[b,e]oxepine and thioglycolic acid were used and reacted in the same manner as in Example 1 to obtain the title compound.

(as ½ $H_2O$ adduct)

White powder m.p. 174° to 179° C.

$^1$H NMR ($\delta$, $CDCl_3$); 3.15 (1H, d), 3.24 (1H, d), 4.85 (1H, d), 5.18 (1H, s), 5.35 to 5.50 (2H, m), 5.94 (1H, d), 6.80 to 6.85 (2H, m), 6.96 (1H, d), 7.20 to 7.30 (4H, m), 7.59 (1H, t), 7.70 to 7.80 (2H, m), 7.86 (1H, d), 8.15 to 8.20 (1H, d), 8.28 (1H, d)

EXAMPLE 23

11-(1-Carboxyethylthio)-2-(quinolin-2-yl)methoxy-6,11-dihydrodibenz[b,e]oxepine: (Exemplary compound 128)

11-Hydroxy-2-(quinolin-2-yl)methoxy-6,11-dihydrodibenz[b,e]oxepine and 2-mercaptopropionic acid were used and reacted in the same manner as in Example 1 to obtain the title compound.

Yellow powder m.p. 179.5° to 181° C.

$^1$H NMR ($\delta$, $CDCl_3$-DMSO-$d_6$); 1.22 to 1.31 (3H, m), 3.15 to 3.30 (1H, m), 4.84 to 4.88 (1H, m), 5.24 to 5.34 (3H, m), 5.93 to 6.06 (1H, m), 6.76 to 8.24 (13H, m)

EXAMPLE 24

11-(3-Carboxypropylthio)-2-(7-chloroquinolin-2-yl)methoxy-6,11-dihydrodibenz[b,e]oxepine: (Exemplary compound 183)

(1) 0.43 g of potassium carbonate was added to 1 g of 2-(7-chloroquinolin-2-yl)methoxy-11-mercapto-6,11-dihydrodibenz[b,e]oxepine and 0.56 g of ethyl 4-bromobutanoate dissolved in 25 ml of acetone and the mixture was stirred under heating for 3 hours. After completion of the reaction, the reaction mixture was filtered and the filtrate was condensed under reduced pressure. The resulting residue was applied to silica gel column chromatography to obtain 0.86 g of 2-(7-chloroquinolin-2-yl)methoxy-11-(3-ethoxycarbonylpropylthio)-6,11-dihydrodibenz[b,e]oxepine as a brown oily product.

$^1$H NMR ($\delta$, $CDCl_3$); 1.24 (3H, t), 1.77 to 1.86 (2H, m), 2.27 to 2.50 (4H, m), 4.12 (2H, q), 4.84 (1H, d), 4.86 (1H, s), 5.32 (2H, s), 6.11 (1H, d), 6.58 (2H, m), 6.89 (1H, d), 7.18 (1H, m), 7.23 to 7.29 (3H, m), 7.50 (1H, dd), 7.67 (1H, d), 7.76 (1H, d), 8.08 (1H, d), 8.16 (1H, d)

(2) 1.9 ml of a 1N-sodium hydroxide aqueous solution was added to 0.84 g of 2-(7-chloroquinolin-2-yl)methoxy-11-(3-ethoxycarbonylpropylthio)-6,11-dihydrodibenz[b,e]oxepine obtained in the above (1) dissolved in 20 ml of ethanol and the mixture was refluxed under heating for 1.5 hours to effect hydrolysis reaction. After the solvent was removed from the reaction mixture, 300 ml of ice water was added to the residue and the mixture was adjusted to about pH 4 with 1N-hydrochloric acid. Crystals precipitated were dissolved in methylene chloride and the organic layer was washed with water, dried over anhydrous sodium sulfate and condensed. The resulting solid was washed with a mixed solution of acetone-hexane to obtain 0.68 g of the title compound as white powder.

m.p. 148° to 153° C.

1H NMR ($\delta$, $CDCl_3$-DMSO-$d_6$); 1.78 to 1.86 (2H, m), 2.32 to 2.41 (2H, m), 2.45 to 2.59 (2H, m), 4.83 (1H, d), 4.89 (1H, s), 5.31 (2H, s), 6.09 (1H, d), 6.78 to 6.85 (2H, m), 6.91 (1H, d), 7.20 to 7.29 (4H, m), 7.50 (1H, d), 7.68 (1H, d), 7.82 (1H, d), 8.06 (1H, s), 8.22 (1H, d)

EXAMPLE 25

11-(5-Carboxypentylthio)-2-(7-chloroquinolin-2-yl)
methoxy-6,11-dihydrodibenz[b,e]oxepine:
(Exemplary compound 185)

2-(7-Chloroquinolin-2-yl)methoxy-11-mercapto-6,11-dihydrodibenz[b,e]oxepine and ethyl 6-bromohexanoate were used and reacted in the same manner as in Example 24 to obtain the title compound.

White powder m.p. 160° to 166° C.

$^1$H NMR (δ, CDCl$_3$-DMSO-d$_6$); 1.26 to 1.59 (6H, m), 2.21 to 2.58 (4H, m), 4.83 (1H, d), 4.88 (1H, s), 5.32 (2H, s), 6.11 (1H, d), 6.78 (1H, d), 6.84 (1H, dd), 6.90 (1H, d), 7.19 (1H, d), 7.22 to 7.32 (3H, m), 7.52 (1H, dd), 7.70 (1H, d), 7.85 (1H, d), 8.05 (1H, d), 8.25 (1H, d)

EXAMPLE 26

11-Carboxymethoxy-2-(6-Chloroquinolin-2-yl)
methoxy-6,11-dihydrodibenz[b,e]oxepine:
(Exemplary compound 115)

(1) While stirring under ice cooling, 0.45 ml of thionyl chloride was added to 2.5 g of 2-(6-chloroquinolin-2-yl)-methoxy-11-hydroxy-6,11-dihydrodibenz[b,e]oxepine suspended in 60 ml of methylene chloride and the mixture was stirred at the same temperature for 30 minutes. After completion of the reaction, the reaction mixture was condensed under reduced pressure, the residue was dissolved in 40 ml of methylene chloride, 4.8 ml of methyl glycolate and 1.7 ml of triethylamine were added to the solution while stirring under ice cooling and the mixture was stirred at room temperature for 4.5 hours. After completion of the reaction, the reaction mixture was washed with water and dried over anhydrous sodium sulfate. The residue obtained by removing the solvent under reduced pressure was applied to silica gel column chromatography to obtain 0.91 g of 2-(6-chloroquinolin-2-yl)methoxy-11-methoxycarbonyl-methoxy-6,11-dihydrodibenz[b,e]oxepine as white powder.

m.p. 144° to 147° C.

$^1$H NMR (CDCl$_3$); 3.70 (3H, s), 4.05 (2H, s), 5.31 (1H, d), 5.33 (1H, s), 5.96 (1H, d), 6.82 (1H, d), 6.92 (1H, dd), 7.03 (1H, d), 7.28 to 7.38 (4H, m), 7.67 (1H, dd), 7.70 (1H, d), 7.82 (1H, d), 8.01 (1H, d), 8.10 (1H, d)

(2) 2.3 ml of a 1N-sodium hydroxide aqueous solution was added to 0.89 g of 2-(6-chloroquinolin-2-yl)methoxy-11-methoxycarbonylmethyl-6,11-dihydrodibenz[b,e]oxepine obtained in the above (1) dissolved in 50 ml of ethanol and the mixture was stirred at room temperature for 2 days to effect hydrolysis. After completion of the reaction, 200 ml of ice water was added to the residue obtained by removing the solvent and the mixture was adjusted to about pH 4 with 1N-hydrochloric acid. Crystals precipitated were collected by filtration and applied to silica gel column chromatography to obtain 0.19 g of the title compound as orange-tinged white powder.

m.p. 179° to 180° C.

$^1$H NMR (δ, CDCl$_3$-DMSO-d$_6$); 3.97 (3H, s), 4.86 (1H, d), 5.30 (2H, s), 5.35 (1H, s), 5.93 (1H, d), 6.77 (1H, d), 6.91 (1H, dd), 7.11 (1H, d), 7.34 (4H, m), 7.67 (1H, dd), 7.71 (1H, d), 7.90 (1H, d), 8.00 (1H, d), 8.22 (1H, d)

EXAMPLE 27

11-Carboxymethoxy-2-(7-chloroquinolin-2-yl)
methoxy-6,11-dihydrobenz[b,e]oxepine: (Exemplary
compound 61)

2-(7-Chloroquinolin-2-yl)methoxy-11-hydroxy-6,11-dihydrodibenz[b,e]oxepine and methyl glycolate were used and reacted in the same manner as in Example 26 to obtain the title compound.

(as ¾ H$_2$O adduct)

White powder m.p. 129° to 130° C.

$^1$H NMR (δ, CDCl$_3$-DMSO-d$_6$); 3.99 (2H, s), 4.85 (1H, d), 5.30 (2H, s), 5.35 (1H, s), 5.95 (1H, d), 6.78 (1H, d), 6.91 (1H, dd), 7.29 to 7.38 (4H, m), 7.51 (1H, dd), 7.68 (1H, dd), 7.84 (1H, d), 8.03 (1H, d), 8.24 (1H, d)

EXAMPLE 28

11-Carboxymethoxy-2-(6-ethylquinolin-2-yl)
methoxy-6,11-dihydrodibenz[b,e]oxepine:
(Exemplary compound 114) (as H$_2$O adduct)

2-(6-Ethylquinolin-2-yl)methoxy-11-hydroxy-6,11-dihydrodibenz[b,e]oxepine and methyl glycolate were used and reacted in the same manner as in Example 26 to obtain the title compound.

White powder m.p. 153° to 154° C.

$^1$H NMR (δ, CDCl$_3$-DMSO-d$_6$); 1.34 (3H, t), 2.85 (2H, q), 3.98 (2H, s), 4.86 (1H, d), 5.29 (1H, s), 5.36 (2H, s), 5.93 (1H, d), 6.76 (1H, d), 6.92 (1H, dd), 7.11 (1H, d), 7.25 to 7.65 (3H, m), 7.95 (1H, d), 8.19 (1H, d)

EXAMPLE 29

11-Carboxymethoxy-2-(quinolin-2-yl)methoxy-6,11-
dihydrodibenz[b,e]oxepine: (Exemplary compound
1)

11-Hydroxy-2-(quinolin-2-yl)methoxy-6,11-dihydrodibenz[b,e]oxepine and methyl glycolate were used and reacted in the same manner as in Example 26 to obtain the title compound.

(as ¼ H$_2$O adduct)

Pale yellow powder m.p. 80° to 83°° C.

$^1$H NMR (δ, CDCl$_3$-DMSO-d$_6$); 4.01 (3H, s), 4.86 (1H, d), 5.33 (2H, s), 5.36 (1H, s), 5.97 (1H, d), 6.79 (1H, d), 6.83 (1H, d), 6.88 (1H, dd), 7.11 (1H, d), 7.27 to 7.36 (4H, m), 7.57 (1H, d), 7.70 (1H, dd), 7.75 (1H, d), 8.06 (1H, d), 8.22 (1H, d)

EXAMPLE 30

2-(7-Chloroquinolin-2-yl)methoxy-11-
[2-(tetrazol-5-yl)ethylthio]-6,11-
dihydrodibenz[b,e]oxepine: (Exemplary compound
192)

1.25 g of trimethyltin azide was added to 1.4 g of 2-(7-chloroquinolin-2-yl)methoxy-11-(2-cyanoethylthio)-6,11-dihydrodibenz[b,e]oxepine dissolved in 40 ml of xylene and the mixture was refluxed under heating for 8.5 hours. After cooling, 1.5 ml of conc. hydrochloric acid was added to the mixture and the mixture was stirred at room temperature for 15 minutes and then adjusted to about pH 4 with a 1N-sodium hydroxide aqueous solution. Crystals precipitated were applied to silica gel column chromatography to obtain 70 mg of the title compound as light orange powder.

m.p. 142° to 147° C.

$^1$H NMR ($\delta$, CDCl$_3$-DMSO-d$_6$); 2.77 to 2.90 (2H, m), 3.08 (2H, t), 4.84 (1H, d), 4.93 (1H, s), 5.31 (2H, s), 6.03 (1H, d), 6.79 (1H, d), 6.84 (1H, dd), 6.91 (1H, d), 7.23 to 7.33 (4H, m), 7.52 (1H, dd), 7.69 (1H, d), 7.84 (1H, d), 8.04 (1H, d), 8.23 (1H, d)

EXAMPLE 31

2-(7-Chloroquinolin-2-yl)methoxy-11-[2-(tetrazol-5-yl)ethoxy]-6,11-dihydrodibenz[b,e]oxepine: (Exemplary compound 72)

2-(7-Chloroquinolin-2-yl)methoxy-11-(2-cyanoethoxy)-6,11-dihydrodibenz[b,e]oxepine and trimethyltin azide were used and reacted in the same manner as in Example 30 to obtain the title compound.

(as ¼ H$_2$O adduct)

Yellowish white powder m.p. 90° to 93° C.

$^1$H NMR ($\delta$, CDCl$_3$-DMSO-d$_6$); 3.14 (2H, m), 3.71 to 3.73 (2H, m), 4.79 (1H, d), 5.18 (1H, s), 5.29 (2H, s), 5.63 (1H, d), 6.70 (1H, d), 6.89 (1H, dd), 6.94 (1H, d), 7.25 to 7.34 (4H, m), 7.52 (1H, dd), 7.68 (1H, d), 7.84 (1H, d), 8.04 (1H, d), 8.24 (1H, d)

EXAMPLE 32

2-(Quinolin-2-yl)methoxy-11-[2-(tetrazol-5-yl)ethylthio]-6,11-dihydrodibenz[b,e]oxepine: (Exemplary compound 132)

0.6 g of ammonium chloride and 0.6 g of sodium azide were added to 1.32 g of 11-(2-cyanoethylthio)-2-(quinolin-2-yl)methoxy-6,11-dihydrodibenz[b,e]oxepine dissolved in 10 ml of dimethylformamide and the mixture was stirred at 120° C. for 10 hours. After completion of the reaction, the solvent was removed and the residue was washed with water and then applied to silica gel column chromatography to obtain 0.3 g of the title compound as slightly brown powder.

m.p. 144° to 145.5° C.

$^1$H NMR ($\delta$, CDCl$_3$-DMSO-d$_6$); 2.75 to 2.90 (2H, m), 3.00 to 3.10 (2H, m), 4.84 (1H, d), 4.89 (1H, s), 5.34 (2H, s), 6.02 (1H, d), 6.80 (1H, d), 6.85 (1H, dd), 6.90 (1H, d), 7.20 to 7.35 (4H, m), 7.55 (1H, t), 7.68 (1H, d), 7.40 (1H, td), 7.86 (1H, d), 8.06 (1H, d), 8.23 (1H, d)

EXAMPLE 33

2-(Quinolin-2-yl)methoxy-11-(tetrazol-5-yl) methylthio-6,11-dihydrodibenz[b,e]oxepine: (Exemplary compound 131)

11-Cyanomethylthio-2-(quinolin-2-yl)methoxy-6,11-dihydrodibenz[b,e]oxepine, ammonium chloride and sodium azide were used and reacted in the same manner as in Example 32 to obtain the title compound.

(as ¼ H$_2$O adduct)

White powder m.p. 193° to 194° C.

$^1$H NMR ($\delta$, CDCl$_3$-DMSO-d6); 3.79 (1H, d), 3.80 (1H, d), 4.88 (1H, d), 5.12 (1H, s), 5.29 (2H, s), 5.97 (1H, d), 6.80 to 6.90 (2H, m), 6.92 (1H, d), 7.20 to 8.35 (4H, m), 7.57 (1H, d), 7.66 (1H, d), 7.73 (1H, td), 7.84 (1H, d), 8.03 (1H, d), 8.22 (1H, d)

EXAMPLE 34

11-[2-(4-Cyanophenylsulfonylamino)ethylthio]-2-(quinlin-2-yl)methoxy-6,11-dihydrodibenz[b,e]oxepine: (Exemplary compound 161)

4.65 g of 11-(2-aminoethylthio)-2-(quinolin-2-yl) methoxy-6,11-dihydrodibenz[b,e]oxepine, 2.0 g of 4-cyanophenylsulfonyl chloride and 2.1 ml of triethylamine dissolved in 30 ml of acetone were refluxed under heating for 1.5 hours. After the reaction mixture was cooled, the reaction mixture was added to ice water and extracted with ethyl acetate and the organic layer was dried over anhydrous sodium sulfate and then condensed. The resulting residue was applied to silica gel column chromatography and the resulting solid was recrystallized from methylene chloride-hexane to obtain 2 g of the title compound as pale yellow crystals.

m.p. 158° to 160° C.

$^1$H NMR ($\delta$, CDCl$_3$-DMSO-d$_6$); 2.45 to 2.60 (2H, m), 2.90 to 3.00 (2H, m), 4.82 (1H, d), 4.89 (1H, s), 5.33 (2H, s), 6.00 (1H, d), 6.80 (1H, d), 6.86 (1H, dd), 6.92 (1H, d), 7.15 to 7.30 (4H, m), 7.56 (1H, t), 7.63 (1H, t), 7.68 (1H, d), 7.74 (1H, td), 7.79 (2H, dd), 7.85 (1H, d), 7.96 (2H, dd), 8.05 (1H, d), 8.23 (1H, d)

EXAMPLE 35

11-(2-Phenylsulfonylaminoethylthio)-2-(7-chloroquinolin-2-yl)methoxy-6,11-dihydrodibenz[b,e]oxepine: (Exemplary compound 208)

11-(2-Aminoethylthio)-2-(7-chloroquinolin-2-yl) methoxy-6,11-dihydrodibenz[b,e]oxepine and phenylsulfonyl chloride were used and reacted in the same manner as in Example 34 to obtain the title compound.

(as ¼ H$_2$O adduct)

Light brown powder m.p. 67° to 70° C.

$^1$H NMR ($\delta$, CDCl$_3$-DMSO-d$_6$); 2.45 to 2.55 (2H, m), 2.88 to 2.94 (2H, m), 4.81 (1H, d), 4.93 (1H, d), 5.31 (2H, s), 6.02 (1H, d), 6.77 (1H, d), 6.84 (1H, dd), 6.96 (1H, t), 7.20 to 7.30 (4H, m), 7.44 to 7.46 (1H, dd), 7.50 to 7.60 (4H, m), 7.69 (1H, d), 7.82 to 7.85 (3H, m), 7.03 (1H, d), 8.24 (1H, d)

EXAMPLE 36

11-[2-(4-Carboxyphenylsulfonylamino)ethylthio]-2-(quinolin-2-yl)methoxy-6,11-dihydrodibenz[b,e]oxepine: (Exemplary compound 154)

20 ml of a 1N-sodium hydroxide aqueous solution was added to 0.4 g of 11-[2-(4-cyanophenylsulfonylamino)ethylthio]-2-(quinolin-2-yl)methoxy-6,11-dihydrodibenz[b,e] oxepine obtained in Example 34 suspended in 5 ml of ethanol and the mixture was refluxed under heating for 6 hours. After completion of the reaction, the solvent was removed, water was added to the residue, insolubles were removed by filtration and then the residue was adjusted to about pH 3 with 1N-hydrochloric acid. Crystals precipitated were collected by filtration and dissolved in ethyl acetate and the organic layer was washed with a saturated saline solution, dried over anhydrous sodium sulfate and condensed. The resulting solid was recrystallized from hexane to obtain 0.33 g of the title compound as yellowish white powder.

m.p. 113° to 115° C.

$^1$H NMR ($\delta$, CDCl$_3$-DMSO-d$_6$); 2.40 to 2.60 (2H, m), 2.80 to 3.00 (2H, m), 4.80 (1H, d), 4.91 (1H, s), 5.33 (2H, s), 6.01 (1H, d), 6.78 (1H, d), 6.84 (1H, dd), 6.94 (1H, d), 7.15 to 7.30 (4H, m), 7.50 (1H, t), 7.57 (1H, d), 7.68 (1H, d), 7.73 (1H, t), 7.86 (1H, d), 7.88 (2H, d), 8.05 (1H, d), 8.15 (2H, d), 8.23 (1H, d)

EXAMPLE 37

2-(Quinolin-2-yl)methoxy-11-[2-[4-(tetrazol-5-yl) phenylsulfonylamino]ethylthio]-6,11-dihydrodibenz[b,e]oxepine: (Exemplary compound 155)

0.89 g of 11-[2-(4-cyanophenylsulfonylamino)ethylthio]-2-(quinolin-2-yl)methoxy-6,11-dihydrodibenz[b,e]oxepine obtained in Example 34, 0.29 g of sodium azide and 0.24 g of ammonium chloride suspended in 5 ml of dimethylformamide were stirred at 120° C. for 1 hour. The reaction mixture was added to ice water and adjusted to about pH 3 with 1N-hydrochloric acid. Crystals precipitated were collected by filtration, dried and then washed with methylene chloride to obtain 0.69 g of the title compound as slightly yellow powder.

(as ½ H$_2$O adduct)

m.p. 199° to 200.5° C.

$^1$H NMR ($\delta$, CDCl$_3$-DMSO-d$_6$); 2.40 to 2.60 (2H, m), 2.85 to 3.00 (2H, m), 4.80 (1H, d), 4.89 (1H, s), 5.33 (1H, d), 6.00 (1H, d), 6.78 (1H, d), 6.83 (1H, dd), 6.92 (1H, d), 7.15 to 7.30 (5H, m), 7.56 (1H, t), 7.67 (1H, d), 7.73 (1H, td), 7.85 (1H, d), 7.97 (2H, dd), 8.05 (1H, d), 8.23 (1H, d), 8.27 (2H, dd)

EXAMPLE 38

2-(Quinolin-2-yl)methoxy-11-[2-(tetrazol-5-yl) carbonylaminoethylthio]-6,11-dihydrodibenz[b,e]oxepine: (Exemplary compound 156)

0.31 ml of oxalyl chloride dissolved in 0.4 ml of acetonitrile was added dropwise at −20° C. to a mixed solution of 1 ml of dimethylformamide and 2 ml of acetonitrile, the mixture was stirred at the same temperature for 15 minutes, 0.57 g of dipotassium tetrazole-5-carboxylate was added to the mixture, the mixture was stirred for 20 minutes to produce (tetrazol-5-yl)carbonyl chloride, 1.29 g of 11-(2-aminoethylthio)-2-(quinolin-2-yl)methoxy-6,11-dihydrodibenz[b,e]oxepine and 1.2 ml of pyridine dissolved in 1.5 m of acetonitrile were added dropwise to the reaction mixture and the mixture was refluxed under heating for 30 minutes. After the reaction mixture was cooled, the reaction mixture was added to ice water and adjusted to about pH 1 with conc. hydrochloric acid and crystals precipitated were collected by filtration and recrystallized from a mixed solution of water-dimethylformamide to obtain 0.57 g of the title compound as white powder.

m.p. 213.5° to 215° C.

$^1$H NMR ($\delta$, CDCl$_3$-DMSO-d$_6$); 2.63 (2H, br. s), 3.55 (2H, br. s), 4.84 (1H, d), 5.11 (1H, s), 5.32 (2H, s), 6.04 (1H, d), 6.76 (1H, d), 6.86 (1H, d), 7.08 (1H, s), 7.20 to 7.45 (4H, m), 7.57 (1H, t), 7.69 (1H, d), 7.74 (1H, t), 7.91 (1H, d), 8.04 (1H, d), 8.30 (1H, d), 9.27 (1H, s)

EXAMPLE 39

11-[(Phenylsulfonyl)aminocarbonyl]methylthio-2-(7-chloroquinolin-2-yl)methoxy-6,11-dihydrodibenz[b,e]oxepine: (Exemplary compound 220)

0.27 g of 11-carboxymethylthio-2-(7-chloroquinolin-2-yl)methoxy-6,11-dihydrodibenz[b,e]oxepine obtained in Example 21, 0.9 g of benzenesulfonamide and 0.14 g of 4-dimethylaminopyridine and 0.11 g of 1-ethyl-3-(3-dimethylaminopropyl)carbodiimide hydrochloride dissolved in 10 ml of methylene chloride were stirred at room temperature for 7 days. After 10 ml of water and 1.13 ml of 1N-hydrochloric acid were added to the reaction mixture, the organic layer was separated, washed with water and dried over anhydrous sodium sulfate. The residue obtained by removing the solvent was applied to silica gel column chromatography to obtain 0.1 g of the title compound as light brown powder.

m.p. 130° to 135° C.

$^1$H NMR ($\delta$, CDCl$_3$-DMSO-d$_6$); 2.91 (2H, d), 3.04 (1H, d), 4.82 (ill, d), 5.04 (1H, s), 5.27 (2H, s), 5.92 (1H, d), 6.78 to 6.86 (4H, m), 6.95 (1H, d), 7.20 to 7.30 (2H, m), 7.47 to 7.71 (4H, m), 7.83 (1H, d), 7.91 to 7.93 (2H, m), 8.01 to 8.10 (2H, m), 8.24 (1H, d)

EXAMPLE 40

2-(7-Chloroquinolin-2-yl)methoxy-11-[2-[(2-methylphenylsulfonyl)aminocarbonyl] ethylthio]-6,11-dihydrodibenz[b,e]oxepine: (Exemplary compound 223)

11-(2-Carboxyethylthio)-2-(7-chloroquinolin-2-yl)methoxy-6,11-dihydrodibenz[b,e]oxepine and 2-methylbenzenesulfonamide were used and reacted in the same manner as in Example 39 to obtain the title compound.

(as ½ H$_2$O adduct)

Pale yellow powder m.p. 87° to 90° C.

$^1$H NMR ($\delta$, CDCl$_3$-DMSO-d$_6$); 2.53 to 2.60 (4H, m), 2.66 (3H, s), 4.80 (1H, d), 4.95 (1H, s), 5.30 (1H, s), 6.01 (1H, d), 6.78 to 6.85 (2H, m), 6.95 (1H, d), 7.18 to 7.35 (6H, m), 7.44 to 7.52 (2H, m), 7.68 (1H, d), 7.80 (1H, d), 8.05 (1H, d), 8.16 (1H, dd)

EXAMPLE 41

11-[(Phenylsulfonyl)aminocarbonyl]methylthio-2-(quinolin-2-yl)methoxy-6,11-dihydrodibenz [b,e]oxepine: (Exemplary compound 160)

11-Carboxymethylthio-2-(quinolin-2-yl)methoxy-6,11-dihydrodibenz[b,e]oxepine and benzensulfonamide were used and reacted in the same manner as in Example 39 to obtain the title compound.

White powder m.p. 148° to 152° C.

¹H NMR (δ, CDCl₃); 3.03 (1H, d), 3.10 (1H, d), 4.78 (1H, s), 4.87 (1H, d), 5.36 (1H, d), 5.42 (lH, d), 5.81 (1H, d), 6.80 (1H, s), 6.86 (2H, s), 7.10 (1H, d), 7.16 (1H, d), 7.20 to 7.35 (2H, m), 7.36 (3H, t), 7.60 to 7.55 (3H, m), 7.85 (1H, d), 8.07 (1H, d), 8.12 (2H, d), 8.23 (1H, d)

EXAMPLE 42

2-(Quinolin-2-yl)methoxy-11-[2-[(tetrazol-5-yl)aminocarbon-yl]ethylthio]-6,11-dihydrodibenz[b,e]oxepine: (Exemplary compound 169)

0.92 g of 11-(2-carboxyethylthio)-2-(quinolin-2-yl) methoxy-6,11-dihydrodibenz[b,e]oxepine obtained in Example 11, 0.21 g of 5-aminotetrazole and 0.5 g of 1-ethyl-3-(3-dimethylaminopropyl)carbodiimide hydrochloride and 0.25 g of 4-dimethylaminopyridine dissolved in 20 ml of methylene chloride were stirred at room temperature for 2 days. After this reaction mixture was washed with 1N-hydrochloric acid and a saturated saline solution, the organic layer was dried over anhydrous sodium sulfate. The residue obtained by condensation was applied to silica gel column chromatography and the resulting solid was recrystallized from methanol to obtain 0.5 g of the title compound as slightly brown powder.

(as ¼ H₂O adduct)

m.p. 206° to 207.5° C.

¹H NMR (δ, CDCl₃-DMSO-d₆); 2.74 (4H, br. s), 4.84 (1H, dd), 5.08 (1H, s), 5.30 (2H, s), 6.04 (1H, dd), 6.80 (1H, d), 6.85 (1H, s), 7.00 (1H, s), 7.29 (4H, s), 7.58 (1H, d), 7.67 (1H, d), 7.75 (1H, s), 7.89 (1H, d), 8.04 (1H, d), 8.27 (1H, d), 12.10 (1H, s)

EXAMPLE 43

2-(Quinolin-2-yl)methoxy-11-[(tetrazol-5-yl)aminocarbonyl]methylthio]-6,11-dihydrodibenz[b,e]oxepine: (Exemplary compound 168)

11-Carboxymethylthio-2-(quinolin-2-yl)methoxy-6,11-dihydrodibenz[b,e]oxepine and 5-aminotetrazole were used and reacted in the same manner as in Example 42 to obtain the title compound.

White powder m.p. 220° to 221.5° C.

¹H NMR (δ, CDCl₃-DMSO-d6); 3.20 to 3.40 (2H, m), 4.87 (1H, d), 5.28 (2H, s), 5.33 (1H, s), 5.98 (1H, d), 6.80 (1H, d), 6.88 (1H, dd), 7.30 (1H, d), 7.25 to 7.35 (4H, m), 7.55 (1H, t), 7.64 (1H, d), 7.71 (1H, t), 7.88 (1H, d), 8.00 (1H, d), 8.27 (1H, d), 12.08 (1H, s), 15.77 (1H, br. s)

EXAMPLE 44

11-Carboxymethoxyimino-2-(quinolin-2-yl)methoxy-6,11-dihydrodibenz[b,e]oxepine: (Exemplary compound 53)

(1) 0.28 g of potassium carbonate was added to 0.6 g of 11-hydroxyimino-2-(quinolin-2-yl)methoxy-6,11-dihydrodibenz[b,e]oxepine and 0.37 g of t-butyl bromoacetic acid ester dissolved in 12 ml of acetone and the mixture was refluxed under heating for 4 hours. After completion of the reaction, the reaction mixture was filtered and the residue obtained by condensing the filtrate under reduced pressure was applied to silica gel column chromatography to obtain 0.62 g of 11-(t-butoxycarbonylmethoxy)imino-2-(quinolin-2-yl)methoxy-6,11-dihydrodibenz[b,e]oxepine as yellowish white powder. Mass (CI); m/z=497 (M⁺+1)

(2) 3 ml of trifluoroacetic acid was added to 0.62 g of 11-(t-butoxycarbonylmethoxy)imino-2-quinolin-2-yl) methoxy-6,11-dihydrodibenz[b,e]oxepine obtained in the above (1) dissolved in 15 ml of methylene chloride and the mixture was stirred at room temperature for 30 minutes to effect hydrolysis. After the solvent was removed from the reaction mixture, ice water was added to the residue, the mixture was adjusted to about pH 4 with a 1N-sodium hydroxide aqueous solution and crystals precipitated were collected by filtration and applied to silica gel column chromatography to obtain 0.2 g of the title compound as white powder.

m.p. 207° to 209° C. (decomposed)

¹H NMR (δ, CDCl₃-DMSO-d₆); 4.62, 4.69 (1H in total, each s), 5.09, 5.16 (1H in total, each s), 5.32 (1H, s), 6.77 to 8.27 (13H, m)

EXAMPLE 45

11-Carboxymethylene-2-(quinolin-2-yl)methoxy-6,11-dihydrodibenz[b,e]oxepine: (Exemplary compound 47)

(1) 1.1 ml of methyl diethylphosphonoacetate dissolved in 10 ml of dimethoxyethane was added to 1.84 g of 11-oxo-2-(quinolin-2-yl)methoxy-6,11-dihydrodibenz[b,e]oxepine and 0.3 g of 64% by weight sodium hydride suspended in 20 ml of dimethoxyethane and the mixture was refluxed under heating for 5 hours. The solvent was removed from the reaction mixture, the residue was dissolved in ethyl acetate and the organic layer was washed with water and a saturated saline solution and then dried over anhydrous sodium sulfate. After the solvent was removed from the solution, the residue was applied to silica gel column chromatography to obtain 2.3 g of 11-methoxycarbonylmethylene-2-(quinolin-2-yl)methoxy-6,11-dihydrodibenz[b,e]oxepine as a brown oily product.

Mass (CI); m/z=424 (M⁺+1)

(2) 6.6 ml of a 1N-sodium hydroxide aqueous solution was added to 2.4 g of 11-methoxycarbonylmethylene-2-(quinolin-2-yl)methoxy-6,11-dihydrodibenz[b,e]oxepine obtained in the above (1) dissolved in 50 ml of ethanol and the mixture was stirred at room temperature for 2 hours to effect hydrolysis. After the solvent was removed from the reaction mixture, ice water was added to the residue and the mixture was adjusted to about pH 3 with 1N-hydrochloric acid. Crystals precipitated were washed with water to obtain 1.68 g of the title compound as Slightly green powder.

m.p. 195° to 197° C.

¹H NMR (δ, CDCl₃-DMSO-d₆); 5.19 (2H, br. s), 5.26 to 5.33 (2H, m), 6.07 to 6.34 (1H, m), 6.70 to 8.25 (13H, m)

EXAMPLE 46

11-(2-Carboxyethylthio)-2-(5-chloro-6-fluoroquinolin-2-yl)methoxy-6,11-dihydrodibenz[b,e]oxepine: (Exemplary compound 329)

2-(5-Chloro-6-fluoroquinolin-2-yl)methoxy-11-hydroxy-6,11-dihydrodibenz[b,e]oxepine and 3-mercaptopropionic acid were used and reacted in the same manner as in Example 1 to obtain the title compound.

White crystals m.p. 135° to 139° C.

$^1$H NMR (δ, CDCl$_3$); 2.60 to 2.75 (3H, m), 2.80 to 2.95 (1H, m), 4.84 (1H, d), 5.00 (1H, s), 5.42 (2H, s), 5.90 (1H, d), 6.78 (1H, d), 6.85 (1H, dd), 6.91 (1H, d), 7.15 to 7.35 (4H, m), 7.64 (1H, t), 7.86 (1H, d), 8.15 to 8.25 (1H, m), 8.66 (1H, d)

EXAMPLE 47

11-(2-Carboxyethylthio)-2-(7-chloro-6-fluoroquinolin-2-yl)methoxy-7-cyano-6,11-dihydrodibenz[b,e]oxepine: (Exemplary compound 330)

2-(7-Chloro-6-fluoroquinolin-2-yl)methoxy-7-cyano-11-hydroxy-6,11-dihydrodibenz[b,e]oxepine and 3-mercaptopropionic acid were used and reacted in the same manner as in Example 1 to obtain the title compound.

Yellowish white powder m.p. 125° to 128° C.

$^1$H NMR (δ, CDCl$_3$); 2.60 to 2.70 (1H, m), 2.70 to 2.85 (2H, m), 2.85 to 2.95 (1H, m), 5.08 (1H, s), 5.31 (1H, d), 5.36 (2H, s), 5.79 (1H, d), 6.80 to 6.90 (3H, m), 7.33 (1H, t), 7.45 (1H, d), 7.57 (2H, t), 7.73 (1H, d), 8.18 (1H, d), 8.29 (1H, d)

EXAMPLE 48

11-(2-Carboxyethylthio)-2-(7-chloro-6-fluoroquinolin-2-yl)methoxy-8-(2-acetylethyl)-6,11-dihydrodibenz[b,e]oxepine: (Exemplary compound 331)

2-(7-Chloro-6-fluoroquinolin-2-yl)methoxy-11-hydroxy-8-(2-acetylethyl)-6,11-dihydrodibenz[b,e]oxepine and 3-mercaptopropionic acid were used and reacted in the same manner as in Example 1 to obtain the title compound.

White powder m.p. 115° to 118° C.

$^1$H NMR (δ, CDCl$_3$); 2.13 (3H, s), 2.60 to 2.70 (3H, m), 2.70 to 2.75 (2H, m), 2.80 to 2.90 (3H, m), 4.79 (2H, d), 4.97 (1H, s), 5.34 (2H, s), 5.86 (1H, d), 6.77 (1H, d), 6.82 (1H, dd), 6.89 (1H, d), 7.05 (2H, d), 7.12 (1H, d), 7.54 (1H, d), 7.71 (1H, d), 8.15 (1H, d), 8.27 (1H, d)

EXAMPLE 49

11-(2-Carboxyethylthio)-2-(7-chloro-6-ethylthioquinolin-2-yl)methoxy-6,11-dihydrodibenz[b,e]oxepine: (Exemplary compound 337)

2-(7-Chloro-6-ethylthioquinolin-2-yl)methoxy-11-hydroxy-6,11-dihydrodibenz[b,e]oxepine and 3-mercaptopropionic acid were used and reacted in the same manner as in Example 1 to obtain the title compound.

White powder m.p. 177° to 179° C. (decomposed)

$^1$H NMR (δ, CDCl$_3$-DMSO-d$_6$); 1.36 (3H, t), 2.35 to 2.45 (2H, m), 2.50 to 2.65 (2H, m), 3.15 (2H, q), 4.88 (1H, d), 5.21 (1H, s), 5.27 (2H, s), 5.92 (1H, d), 6.76 (1H, d), 6.89 (1H, dd), 7.04 (1H, d), 7.30 to 7.35 (4H, m), 7.67 (1H, d), 7.92 (1H, s), 8.11 (1H, s), 8.38 (1H, d), 11.80 to 12.20 (1H, br. s)

EXAMPLE 50

(+)-11-(2-Carboxyethylthio)-2-(7-chloro-6-fluoroquinolin-2-yl)methoxy-6,11-dihydrodibenz[b,e]oxepine: (Optical isomer of Exemplary compound 262)

1.50 g of (1S)-(+)-10-camphor-sulfonic acid monohydrate was added to 6.12 g of 11-(2-carboxyethylthio)-2-(7-chloro-6-fluoroquinolin-2-yl)methoxy-6,11-dihydrodibenz[b,e]oxepine obtained in Example 1 dissolved in a mixed solution of 110 ml of dimethylformamide and 440 ml of acetonitrile and the mixture was stirred at room temperature for 3.5 hours. After the reaction mixture was left to stand overnight, crystals precipitated were removed by filtration, 1.5 g of (1R)-(−)-10-camphor-sulfonic acid monohydrate was added to the mother liquor and the mixture was stirred at room temperature for 4 hours. After the reaction mixture was left to stand overnight, crystals precipitated were collected by filtration and washed with a mixed solution of dimethylformamide and acetonitrile and then with diethyl ether to obtain 3.51 g of yellow crystals.

These crystals were suspended in a mixed solution of 31.6 ml of dimethylsulfoxide and 61.8 ml of water, 397.4 mg of sodium hydrogen carbonate was added to the suspension at room temperature under stirring and the mixture was stirred for 5 minutes.

White crystals formed were collected by filtration, washed with purified water and dried. 2.4 g of these crystals were recrystallized from a mixed solution of dimethylformamide and methanol to obtain 3.02 g of the title compound as while needle crystals.

m.p. 180° to 181° C.

$^1$H NMR (δ, CDCl$_3$-DMSO-d$_6$); 2.42 (2H, t), 2.55 to 2.75 (2H, m), 4.83 (1H, d), 5.00 (1H, s), 5.28 (2H, s), 6.06 (1H, d), 6.77 (1H, d), 6.83 (1H, dd), 6.95 (1H, d), 7.25 to 7.35 (4H, m), 7.67 (1H, d), 7.70 (1H, d), 8.14 (1H, d), 8.23 (1H, d), 11.80 to 12.20 (1H, br. s)

$[\alpha]_D^{20}$ +89.82° (c=0.10, dioxane)

HPLC analysis; retention time 11.5 minutes, optical purity 100% ee

Analysis conditions

Column: ULTRON ES-OVM, 4.6×150 mm

Eluting solution: 20 mM sodium dihydrogen phosphonate solution (adjusted to pH 5.5 with a 0.1N sodium hydroxide aqueous solution)/acetonitrile/methanol=40/13/8

Flow rate: 0.8 ml/min

Detection: UV 254 nm

EXAMPLE 51

(−)-11-(2-Carboxyethylthio)-2-(7-chloro-6-fluoroquinolin-2-yl)methoxy-6,11-dihydrodibenz[b,e]oxepine: (Optical isomer of Exemplary compound 262)

1.50 g of (1S)-(+)-10-camphor-sulfonic acid monohydrate was added to 6.12 g of 11-(2-carboxyethylthio)-2-(7-chloro-6-fluoroquinolin-2-yl)methoxy-6,11-dihydrodibenz[b,e]oxepine obtained in Example 1 dissolved in a mixed solution of 110 ml of dimethylformamide and 440 ml of acetonitrile and the mixture was stirred at room temperature for 3.5 hours. After the reaction mixture was left to stand overnight, crystals precipitated were collected by filtration and washed with a mixed solution of dimethylformamide and acetonitrile and then with diethyl ether to obtain 3.50 g of yellow crystals.

These crystals were suspended in a mixed solution of 31.6 ml of dimethylsulfoxide and 61.8 ml of water, 396.5 mg of sodium hydrogen carbonate was added to the suspension at room temperature under stirring and the mixture was stirred for 5 minutes. White crystals formed were collected by filtration, washed with purified water and dried. 2.34 g of these crystals were recrystallized from a mixed solution of dimethylformamide and methanol to obtain 1.89 g of the title compound as while needle crystals.

m.p. 182° to 184° C.

$^1$H NMR; same as in Example 50

$[\alpha]_D^{20}$ 89.82° (c=0.10, dioxane)

HPLC analysis; retention time 8.2 minutes, optical purity 100% ee

Analysis conditions: same as in Example 50

EXAMPLE 52

(+)-11-(2-Carboxyethylthio)-2-(7-chloroquinolin-2-yl)methoxy-6,11-dihydrodibenz[b,e]oxepine: (Optical isomer of Exemplary compound 182)

The title compound was obtained from 11-(2-carboxyethylthio)-2-(7-chloroquinolin-2-yl)methoxy-6,11-dihydrodibenz[b,e]oxepine obtained in Example 2 by the same operation as in Example 50.

White needle crystals m.p. 182° to 184° C.

$^1$H NMR ($\delta$, CDCl$_3$-DMSO-d$_6$); 2.43 (2H, t), 2.55 to 2.70 (2H, m), 4.84 (1H, d), 4.99 (1H, s), 5.31 (2H, s), 6.07 (1H, d), 6.78 (1H, d), 6.84 (1H, dd), 6.95 (1H, d), 7.25 to 7.35 (4H, m), 7.52 (1H, dd), 7.69 (1H, d), 7.85 (1H, d), 8.05 (1H, s), 8.25 (1H, d)

$[\alpha]_D^{20}$ +92.81° (c=0.10, dioxane)

HPLC analysis; retention time 14.9 minutes, optical purity 100% ee

Analysis conditions: same as in Example 50

EXAMPLE 53

(−)-11-(2-Carboxyethylthio)-2-(7-chloroquinolin-2-yl)-methoxy-6,11-dihydrodibenz[b,e]oxepine: (Optical isomer of Exemplary compound 182)

The title compound was obtained from 11-(2-carboxyethylthio)-2-(7-chloroquinolin-2-yl)methoxy-6,11-dihydrodibenz[b,e]oxepine obtained in Example 2 by the same operation as in Example 51.

White needle crystals m.p. 181° to 182° C.

$^1$H NMR; same as in Example 52

$[\alpha]_D^{20}$ −90.15° (c=0.10, dioxane)

HPLC analysis; retention time 7.8 minutes, optical purity 100% ee

Analysis conditions: same as in Example 50

Reference Example 1

7-chloro-6-fluoroquinarldine

Under reflux under heating, a mixed solution of 17.2 ml of crotonaldehyde and 2.6 ml of water was added over 35 minutes to 29.1 g of 3-chloro-4-fluoroaniline dissolved in a mixed solution of 40 ml of water and 62 ml of conc. hydrochloric acid and the mixture was refluxed under heating for 2 hours. After cooling, the reaction mixture was washed with diethyl ether and crystals precipitated by adding 27.2 g of zinc chloride to the aqueous layer were collected by filtration and washed with 3N-hydrochloric acid, isopropyl alcohol and then diethyl ether. The crystals were added to ice water and the mixture was adjusted to about pH 9 with conc. aqueous ammonia and then extracted with chloroform. After the organic layer was washed with water and then dried over anhydrous sodium sulfate, the solvent was removed to obtain 10.7 g of the title compound.

Mass (CI); m/z=196 (M$^+$+1)

Reference Example 2

7-Chloro-6-fluoro-2-formylquinoline 10.73 g of 7-chloro-6-fluoroquinaldine obtained in Reference example 1 and 12.17 g of selenium dioxide were suspended in a mixed solution of 210 ml of dioxane and 5.7 ml of water and the mixture was stirred at 130° C. for 1 hour. After the solvent was removed, the residue was dissolved in methylene chloride and the organic layer was washed with water and dried over anhydrous sodium sulfate. The solvent was removed to obtain 1.19 g of the title compound.

Mass (CI); m/z=210 (M$^+$+1)

Reference Example 3

7-Chloro-6-fluoro-2-hydroxymethylquinoline 3 g of sodium boron hydride was added to 11.19 g of 7-chloro-6-fluoro-2-formylquinoline obtained in Reference example 2 suspended in 250 ml of methanol and the mixture was stirred at room temperature for 1 hour. After the solvent was removed, the residue was extracted with ice water-methylene chloride and the organic layer was washed with water and dried over anhydrous sodium sulfate. After the solvent was removed, the residue was applied to silica gel column chromatography to obtain 7.84 g of the title compound.

Mass (CI); m/z=212 (M$^+$+1)

By the same operation procedures as described in Reference example 1, Reference example 2 and Reference example 3, the respective title compounds of Reference examples 4 to 12 were obtained.

Reference Example 4

7-Chloro-2-hydroxymethylquinoline

Mass (CI); m/z=194 (M$^+$+1)

Reference Example 5

6-Fluoro-2-hydroxymethylquinoline

Mass (CI); m/z=178 (M$^+$+1)

Reference Example 6

7-Fluoro-2-hydroxymethylquinoline

Mass (CI); m/z=178 (M$^+$+1)

Reference Example 7

6-Chloro-2-hydroxymethylquinoline

Mass (CI); m/z=194 (M$^+$+1)

Reference Example 8

8-Fluoro-2-hydroxymethylquinoline

Mass (CI); m/z=178 (M$^+$+1)

Reference Example 9

5,7-Dichloro-2-hydroxymethylquinoline

Mass (CI); m/z=228 (M$^+$+1)

Reference Example 10

6-Ethyl-2-hydroxymethylquinoline

Mass (CI); m/z=188 (M$^+$+1)

Reference Example 11

5-Chloro-6-fluoro-2-hydroxymethylquinoline

Mass (CI); m/z=212 (M$^+$+1)

Reference Example 12

6-Methoxy-2-hydroxymethylquinoline

Mass (CI); m/z=190 (M$^+$+1)

Reference Example 13

7-Hydroxyquinaldine 7.46 g of 7-methoxyquinaldine obtained by the same method as in Reference example 1 dissolved in a 47% hydrobromic acid solution was stirred at 150° C. for 14 hours. Ice water was added to the reaction mixture and the mixture was adjusted to about pH 8 with conc. aqueous ammonia, crystals precipitated were dissolved in ethyl acetate and the organic layer was washed with water and then dried over anhydrous sodium sulfate. The solvent was removed to obtain 4.8 g of the title compound.

Mass (CI); m/z=160 (M$^+$+1)

Reference Example 14

7-Difluoromethoxyquinaldine

Under ice cooling and stirring, 4.83 g of 7-hydroxyquinaldine obtained in Reference example 13 dissolved in 40 ml of methylene chloride was added to 8.4 g of potassium hydroxide dissolved in 25 ml of water. After 0.97 g of tetrabutylammonium bromide was added to the reaction mixture, chlorodifluoromethane was blown into the mixture and the mixture was stirred at the same temperature for 1 hour. The reaction mixture was washed with a 1N-sodium hydroxide aqueous solution and water, the organic layer was dried over anhydrous sodium sulfate and the solvent was removed. The residue was applied to silica gel column chromatography to obtain 5.28 g of the title compound.

Mass (CI); m/z=210 (M$^+$+1)

Reference Example 15

7-Difluoromethoxy-2-hydroxymethylquinoline

The title compound was obtained from 7-difluoromethoxyquinaldine obtained in Reference example 14 in the same manner as in Reference example 2 and Reference example 3.

Mass (CI); m/z=226 (M$^+$+1)

Reference Example 16

3-Cyano-o-toluic acid

Under ice cooling and stirring, 1.5 g of sodium nitrite dissolved in 2 ml of water was added dropwise over 1.5 hours to 3 g of 3-amino-o-toluic acid dissolved in a mixed solution of 8 ml of acetic acid, 8.3 g of sulfuric acid and 6.5 ml of water. After 3.2 ml of acetic acid, 0.4 g of sulfuric acid and 5.6 ml of water were added to the reaction mixture, the mixture was filtered and the reaction filtrate was adjusted. On the other hand, 6.5 g of potassium cyanide dissolved in 12.7 ml of water was added dropwise to 5.9 g of copper sulfate.pentahydrate dissolved in 12.7 ml of water at room temperature under stirring and 21.5 g of sodium hydrogen carbonate and 70 ml of toluene were added to the mixture. Under ice cooling and stirring, the above reaction filtrate was added dropwise to this 10 reaction mixture over 1 hour and then the mixture was stirred at 80° C. for 30 minutes. After completion of the reaction, the reaction mixture was adjusted to about pH 3 with 1N-hydrochloric acid, crystals precipitated were extracted with ethyl acetate and the organic layer was washed with a saturated saline solution and then dried over anhydrous sodium carbonate. The solvent was removed to obtain 3.8 g of the title compound.

Mass (CI); m/z=162 (M$^+$+1)

Reference Example 17

Methyl 3-cyano-o-toluate 3.2 g of 3-cyano-o-toluic acid obtained in Reference example 16 and 0.5 ml of conc. sulfuric acid dissolved in 25 ml of methanol were refluxed under heating for 2 days. During reflux, 5 ml of methanol and 0.5 ml of conc. sulfuric acid were added to the mixture twice. After the solvent was removed, the residue was dissolved in ethyl acetate and the organic layer was washed with a saturated saline solution, a saturated sodium hydrogen carbonate solution and then a saturated saline solution and dried over anhydrous sodium sulfate. After the solvent was removed, the residue was applied to silica gel column chromatography to obtain 2.62 g of the title compound.

Mass (CI); m/z=176 (M$^+$+1)

Reference Example 18

Methyl 4-bromo-o-toluate

The title compound was obtained from 4-bromotoluic acid in the same manner as in Reference example 17.

Mass (CI); m/z=229 (M$^+$+1)

Reference Example 19

Methyl 4-methoxy-o-toluate 12.6 g of a 28% sodium methylate methanol solution and 4.2 g of copper iodide were added to 5 g of methyl 4-bromo-toluate dissolved in 20 ml of dimethylformamide and the mixture was refluxed under heating for 2 hours. The reaction mixture was adjusted to about pH 2 by adding 1N-hydrochloric acid thereto and extracted with ethyl acetate. and the organic layer was washed with a saturated saline solution and then dried over anhydrous sodium sulfate. The residue obtained by removing the solvent was applied to silica gel column chromatography to obtain 2.47 g of the title compound.

Mass (CI); m/z=181 ($M^+$+1)

Reference Example 20

Methyl 4-cyano-o-toluate 0.5 g of cuprous cyanide was added to 1 g of methyl 4-bromo-o-toluate obtained in Reference example 18 dissolved in 0.7 ml of dimethylformamide and the mixture was refluxed under heating for 6 hours. Then, to the reaction mixture were added 2.6 ml of water, 0.5 ml of conc. hydrochloric acid and 1.75 g of ferric chloride and the mixture was stirred at 60° to 70° C. for 30 minutes. After the reaction mixture was extracted with ethyl acetate, the organic layer was washed with a saturated saline solution and dried over anhydrous sodium sulfate. The solvent was removed from the solution to obtain 0.76 g of the title compound.

Mass (CI); m/z=176 ($M^+$+1)

Reference Example 21

Methyl 2-bromomethyl-4-cyanobenzoate 1.0 g of benzoyl peroxide and 8.0 g of N-bromosuccinimide were added to 7.5 g of methyl 4-cyano-o-toluate obtained in Reference example 20 dissolved in 50 ml of carbon tetrachloride and the mixture was refluxed under heating for 8 hours. During reflux, 3 g of N-bromosuccinimide was added to the mixture. The resulting reaction mixture was filtered and the filtrate was washed with a saturated saline solution and then dried over anhydrous sodium sulfate. The solvent was removed from the solution to obtain 20 g of a crude product of the title compound.

Mass (CI); m/z=254 ($M^+$+1)

Reference Example 22

Methyl 4-cyano-2-(4-hydroxyphenoxy)methylbenzoate 5.9 g of potassium carbonate and a catalytic amount of potassium iodide were added to 20 g of methyl 2-bromomethyl-4-cyanobenzoate obtained in Reference example 21 and 14.2 g of hydroquinone dissolved in 60 ml of dimethylformamide and the mixture was stirred at 90° C. for 3 hours. After the solvent was removed from the reaction mixture under reduced pressure, water was added to the residue, the mixture was extracted with ethyl acetate and the organic layer was washed with a saturated saline solution and dried over anhydrous sodium sulfate. The solvent was removed from the solution to obtain 9.5 g of the title compound.

Mass (CI); m/z=284 ($M^+$+1)

Reference Example 23

4-Cyano-2-(4-hydroxyphenoxy)methylbenzoic acid 20 ml of a 3N-sodium hydroxide aqueous solution was added to 9.5 g of methyl 4-cyano-2-(4-hydroxyphenoxy)methylbenzoate obtained in Reference example 22 dissolved in 80 ml of methanol and the mixture was stirred at room temperature for 1.5 hours. After completion of the reaction, the solvent was removed under reduced pressure, water was added to the residue and the mixture was washed with diethyl ether and then adjusted to about pH 2 with conc. sulfuric acid. Crystals precipitated were collected by filtration and dissolved in ethyl acetate and the organic layer was washed with a saturated saline solution and then dried over anhydrous sodium sulfate. The solvent was removed from the solution to obtain 5.2 g of the title compound.

Mass (CI); m/z=270 ($M^+$+1)

Reference Example 24

2-(4-Acetoxyphenoxy)methyl-2-cyanobenzoic acid

Under ice cooling and stirring, 5.5 ml of acetic anhydride was added to 5.2 g of 4-cyano-2-(4-hydroxyphenoxy)methylbenzoic acid obtained in Reference example 23 dissolved in 15.6 ml of pyridine and the mixture was stirred at the same temperature for 1.5 hours. Water was added to the reaction mixture and the mixture was adjusted to about pH 2 with conc. hydrochloric acid and extracted with ethyl acetate. Then, the organic layer was washed with a saturated saline solution, 1N-hydrochloric acid and further a saturated saline solution and then dried over anhydrous sodium sulfate. The solvent was removed to obtain 5.36 g of a crude product of the title compound.

Mass (CI); m/z=312 ($M^+$+1)

Reference Example 25

2-Acetoxy-8-cyano-11-oxo-6,11-dihydrodibenz[b,e]oxepine 3 ml of trifluoroacetic anhydride and 0.48 g of a trifluoroboran-diethyl ether complex were added to 5.36 g of 2-(4-acetoxyphenoxy)methyl-4-cyanobenzoic acid obtained in Reference example 24 dissolved in 80 ml of methylene chloride and the mixture was stirred at room temperature for 8 hours. Water was added to the reaction mixture, the mixture was neutralized with a 1N-sodium hydroxide aqueous solution and crystals precipitated were extracted with chloroform. Then, the organic layer was dried over anhydrous sodium sulfate and the residue obtained by removing the solvent was applied to silica gel column chromatography to obtain 2.8 g of the title compound.

Mass (CI); m/z=294 ($M^+$+1)

Reference Example 26

8-Cyano-2-hydroxy-11-oxo-6,11-dihydrodibenz[b,e]oxepine 6 ml of a 3N-sodium hydroxide aqueous solution was added to 2.8 g of 2-acetoxy-8-cyano-11-oxo-6,11-dihydrodibenz[b,e]oxepine obtained in Reference example 25 dissolved in 30 ml of methanol and the mixture was stirred at room temperature for 3 hours. After completion of the reaction, the solvent was removed under reduced pressure, water was added to the residue and the mixture was adjusted to about pH 2 with conc. hydrochloric acid. Crystals precipitated were collected by filtration and dissolved in ethyl acetate and the organic layer was washed with a saturated saline solution and then dried over anhydrous sodium sulfate. The solvent was removed from the solution to obtain 2.35 g of the title compound.

Mass (CI); m/z=252 (M$^+$+1)

By the same operation procedures as described in Reference example 21 to Reference example 26, the respective title compounds of Reference examples 27 to 29 were obtained.

Reference Example 27

8-Bromo-2-hydroxy-11-oxo-6,11-dihydrodibenz[b,e]oxepine

Mass (CI); m/z=305 (M$^+$+1)

Reference Example 28

2-Hydroxy-8-methoxy-11-oxo-6,11-dihydrodibenz[b,e]oxepine

Mass (CI); m/z=257 (M$^+$+1)

Reference Example 29

7-Cyano-2-hydroxy-11-oxo-6,11-dihydrodibenz[b,e]oxepine

Mass (CI); m/z=252 (M$^+$+1)

Reference Example 30

2-Methoxy-10-methyl-11-oxo-6,11-dihydrodibenz[b,e]oxepine

The title compound was obtained by the same operation procedures as described in Reference example 21 to Reference example 23 and Reference example 25.

Mass (CI); m/z=255 (M$^+$+1)

Reference Example 31

2-Hydroxy-10-methyl-11-oxo-6,11-dihydrodibenz[b,e]oxepine 3.39 g of 2-methoxy-10-methyl-11-oxo-6,11-dihydrodibenz[b,e]oxepine obtained in Reference example 30 suspended in 17 ml of 47% hydrobromic acid was refluxed under heating for 4 hours. The reaction mixture was added to ice water and crystals precipitated were collected by filtration. The crystals were dissolved in 180 ml of a 3% sodium hydroxide aqueous solution and insolubles were removed by filtration. The pH of the filtrate was adjusted to about 6 with 1N-hydrochloric acid, crystals precipitated were collected by filtration, the crystals were dissolved in ethyl acetate and the organic layer was washed with water and dried over anhydrous sodium sulfate. The residue obtained by removing the solvent was applied to silica gel column chromatography to obtain 1.22 g of the title compound.

Mass (CI); m/z=241 (M$^+$+1)

Reference Example 32

2-Hydroxy-11-oxo-6,11-dihydrodibenz[b,e]oxepine

The title compound was obtained by the same operation procedures as described in Reference examples 25 and 31.

Mass (CI); m/z=227 (M$^+$+1)

Reference Example 33

2-Hydroxy-8-iodo-11-oxo-6,11-dihydrodibenz[b,e]oxepine 10.35 g of copper (I) iodide and 26.9 g of potassium iodide were added to 3.3 g of 8-bromo-2-hydroxy-11-oxo-6,11-dihydrodibenz[b,e]oxepine obtained in Reference example 27 dissolved in 33 ml of hexamethylphosphoric acid triamide and the mixture was stirred under nitrogen stream at 160° C. for 4 hours. After 300 ml of water and 400 ml of ethyl acetate were added to the reaction mixture, the organic layer was separated, washed with water and dried over anhydrous sodium sulfate. The residue obtained by removing the solvent was washed with chloroform to obtain 1.42 g of the title compound.

Mass (CI); m/z=353 (M$^+$+1)

Reference Example 34

2-(7-chloro-6-fluoroquinolin-2-yl)methoxy-11-oxo-6,11-dihydrodibenz[b,e]oxepine

Under ice cooling and stirring, 2 ml of thionyl chloride was added to 3 g of 7-chloro-6-fluoro-2-hydroxymethylquinoline obtained in Reference example 3 suspended in 70 ml of methylene chloride, the mixture was stirred at room temperature for 2.5 hours and then the reaction mixture was condensed under reduced pressure.

Then, to the resulting condensed residue were added 3.21 g of 2-hydroxy-11-oxo-6,11-dihydrodibenz[b,e]oxepine and 3.94 g of potassium carbonate suspended in 28 ml of dimethylformamide and the mixture was stirred at 90° C. for 1.5 hours. Ice water was added to the reaction mixture, the mixture was extracted with methylene chloride and the organic layer was washed with water, a 1N-sodium hydroxide aqueous solution and further water and dried over anhydrous sodium sulfate. The residue obtained by removing the solvent was applied to silica gel column chromatography to obtain 2.58 g of the title compound.

Mass (CI); m/z=420 (M$^+$+1)

Reference Example 35

2-(7-Chloro-6-fluoroquinolin-2-yl)methoxy-11-hydroxy-6,11-dihydrodibenz[b,e]oxepine 0.5 g of sodium boron hydride was added to 2.58 g of 2-(7-chloro-6-fluoroquinolin-2-yl)methoxy-11-oxo-6,11-dihydrodibenz[b,e]oxepine obtained in Reference example 34 suspended in 70 ml of methanol and the mixture was stirred at room temperature for 11 hours. During stirring, 0.35 g of sodium boron hydride was added to the mixture twice. After completion of the reaction, the solvent was removed under reduced pressure, ice water was added to the residue and the mixture was extracted with methylene chloride. Then, the organic layer was washed with water and then dried over anhydrous sodium sulfate and the solvent was removed. The resulting solid was washed with a methylene chloride-hexane mixed solution to obtain 1.87 g of the title compound. Mass (CI); m/z=422 (M$^+$+1)

By the same operation procedures as described in Reference example 34 and Reference example 35, the respective title compounds of Reference examples 36 to 53 were obtained.

Reference Example 36

2-(7-Chloroquinolin-2-yl)methoxy-11-hydroxy-6,11-dihydrodibenz[b,e]oxepine

Mass (CI); m/z=404 (M$^+$+1)

Reference Example 37

2-(6-Fluoroquinolin-2-yl)methoxy-11-hydroxy-6,11-dihydrodibenz[b,e]oxepine

Mass (CI); m/z=388 (M$^+$+1)

Reference Example 38

2-(7-Fluoroquinolin-2-yl)methoxy-11-hydroxy-6,11-dihydrodibenz[b,e]oxepine

Mass (CI); m/z=388 (M$^+$+1)

Reference Example 39

2-(6-Chloroquinolin-2-yl)methoxy-11-hydroxy-6,11-dihydrodibenz[b,e]oxepine

Mass (CI); m/z=404 (M$^+$+1)

Reference Example 40

2-(7-Difluoromethoxyquinolin-2-yl)methoxy-11-hydroxy-6,11-dihydrodibenz[b,e]oxepine Mass (CI); m/z=436 (M$^+$+1)

Reference Example 41

2-(8-Fluoroquinolin-2-yl)methoxy-11-hydroxy-6,11-dihydrodibenz[b,e]oxepine

Mass (CI); m/z=388 (M$^+$+1)

Reference Example 42

2-(5,7-Dichloroquinolin-2-yl)methoxy-11-hydroxy-6,11-dihydrodibenz[b,e]oxepine

Mass (CI); m/z=438 (M$^+$+1)

Reference Example 43

2-(6-Ethylquinolin-2-yl)methoxy-11-hydroxy-6,11-dihydrodibenz[b,e]oxepine

Mass (CI); m/z=398 (M$^+$+1)

Reference Example 44

11-Hydroxy-2-(6-methoxyquinolin-2-yl)methoxy-6,11-dihydrodibenz[b,e]oxepine

Mass (CI); m/z=400 (M$^+$+1)

Reference Example 45

11-Hydroxyl-2-(quinolin-2-yl)methoxy-6,11-dihydrodibenz[b,e]oxepine

Mass (CI); m/z=370 (M$^+$+1)

Reference Example 46

2-(7-Chloroquinolin-2-yl)methoxy-11-hydroxy-10-methyl-6,11-dihydrodibenz[b,e]oxepine Mass (CI); m/z=418 (M$^+$+1)

Reference Example 47

2-(7-Chloroquinolin-2-yl)methoxy-6,11-hydroxy-8-methoxy-6,11-dihydrodibenz[b,e]oxepine Mass (CI); m/z=434 (M$^+$+1)

Reference Example 48

8-Bromo-2-(7-chloroquinolin-2-yl)methoxy-11-hydroxy-6,11-dihydrodibenz[b,e]oxepine Mass (CI); m/z=482 (M$^+$+1)

Reference Example 49

2-(7-Chloroquinolin-2-yl)methoxy-7-cyano-11-hydroxy-6,11-dihydrodibenz[b,e]oxepine Mass (CI); m/z=429 (M$^+$+1)

Reference Example 50

2-(7-Chloroquinolin-2-yl)methoxy-8-cyano-11-hydroxy-6,11-dihydrodibenz[b,e]oxepine Mass (CI); m/z=429 (M$^+$+1)

Reference Example 51

2-(5-Chloro-6-fluoroquinolin-2-yl)methoxy-11-hydroxy-6,11-dihydrodibenz[b,e]oxepine Mass (CI); m/z=422 (M$^+$+1)

Reference Example 52

2-(7-Chloro-6-fluoroquinolin-2-yl)methoxy-7-cyano-11-hydroxy-6,11-dihydrodibenz[b,e]oxepine Mass (CI); m/z=447 (M$^+$+1)

Reference Example 53

2-(7-Chloro-6-fluoroquinolin-2-yl)methoxy-11-hydroxy-8-iodo-6,11-dihydrodibenz[b,e]oxepine Mass (CI); m/z=548 (M$^+$+1)

Reference Example 54

2-(7-Chloroquinolin-2-yl)methoxy-8-methoxycarbonylmethylthio-11-oxo-6,11-dihydrodibenz[b,e]oxepine 1.15 g of potassium carbonate was added to 2.27 g of 8-bromo-2-(7-chloroquinolin-2-yl)methoxy-11-oxo-6,11-dihydrodibenz[b,e]oxepine obtained in the same manner as in Reference example 34 and 0.74 ml of methyl thioglycolate dissolved in 100 ml of acetone and the mixture was refluxed under heating under nitrogen stream for 2 hours. During the reaction, 0.74 g of methyl thioglycolate and 1.15 g of potassium carbonate were added to the mixture. After completion of the reaction, the reaction mixture was condensed under reduced pressure, water was added to the residue and the mixture was adjusted to about pH 8 with 1N-hydrochloric acid. Crystals precipitated were extracted with chloroform and the organic layer was washed with a saturated saline solution and then dried over anhydrous sodium sulfate. The residue obtained by removing the solvent was applied to silica gel column chromatography to obtain 2.41 g of the title compound.

Mass (FAB); m/z=507 ($M^+$+1)

Reference Example 55

8-Carboxymethylthio-2-(7-chloroquinolin-2-yl)methoxy-11-oxo-6,11-dihydrodibenz[b,e]oxepine 5.7 ml of a 1N-sodium hydroxide aqueous solution was added to 2.31 g of 2-(7-chloroquinolin-2-yl)methoxy-11-oxo-6,11-dihydrodibenz[b,e]oxepine obtained in Reference example 54 dissolved in 60 ml of methanol and the mixture was refluxed under heating for 6 hours. After completion of the reaction, the solvent was removed under reduced pressure, water was added to the residue and the mixture was adjusted to about pH 4 with 1N-hydrochloric acid. Crystals precipitated were collected by filtration and recrystallized from methanol to obtain the title compound.

Mass (FAB); m/z=492 ($M^+$+1)

Reference Example 56

8-Carboxymethylthio-2-(7-chloroquinolin-2-yl)methoxy-11-hydroxy-6,11-dihydrodibenz[b,e]oxepine Title compound was obtained from the compound obtained in Reference example 55 by the same method as in Reference example 35.

Mass (FAB); m/z=494 ($M^+$+1)

Reference Example 57

2-(7-Chloroquinolin-2-yl)methoxy-11-oxo-8-(tetrazol-5-yl)-6,11-dihydrodibenz[b,e]oxepine 1.03 g of trimethyltin azide was added to 1.07 g of 2-(7-chloroquinolin-2-yl)methoxy-8-cyano-11-oxo-6,11-dihydrodibenz[b,e]oxepine obtained by the same method as in Reference example 34 suspended in 30 ml of xylene and the mixture was refluxed under heating for 13 hours. 1 ml of conc. hydrochloric acid was added to the reaction mixture, the mixture was adjusted to about pH 4 with a 1N-sodium hydroxide aqueous solution and crystals precipitated were collected by filtration. The crystals were dissolved in a chloroform-methanol mixed solution and the organic layer was washed with a saturated saline solution and then dried over anhydrous sodium sulfate. The residue obtained by removing the solvent was applied to silica gel column chromatography to obtain 1.25 g of the title compound.

Mass (EI); m/z=469 ($M^+$)

Reference Example 58

2-(7-Chloroquinolin-2-yl)methoxy-11-hydroxy-8-(tetrazol-5-yl)-6,11-dihydrodibenz[b,e]oxepine The title compound was obtained from the compound of Reference example 57 by the same method as in Reference example 35.

Mass (CI); m/z=472 ($M^+$+1)

By the same operation procedures as described in Reference example 57 and Reference example 35, the respective title compounds of Reference examples 59 and 60 were obtained.

Reference Example 59

2-(7-Chloroquinolin-2-yl)methoxy-11-hydroxy-7-(tetrazol-5-yl)-6,11-dihydrodibenz[b,e]oxepine Mass (FAB); m/z=472 ($M^+$+1)

Reference Example 60

11-Hydroxy-2-quinolin-2-yl)methoxy-8-(tetrazol-5-yl)-6,11-dihydrodibenz[b,e]oxepine Mass (CI); m/z=438 ($M^+$+1)

Reference Example 61

2-(7-Chloro-6-ethylthioquinolin-2-yl)methoxy-11-oxo-6,11-dihydrodibenz[b,e]oxepine 0.37 ml of ethyl mercaptan and 1.12 g of potassium carbonate were added to 2.0 g of 2-(7-chloro-6-fluoroquinolin-2-yl)methoxy-11-oxo-6,11-dihydrodibenz[b,e]oxepine dissolved in 80 ml of dimethylformamide and the mixture was stirred at 90° C. for 4 hours.

After cooling, crystals precipitated were collected by filtration, washed with water and then washed with a chloroform-hexane (1:4) mixed solution to obtain 1.33 g of the title compound.

Mass (CI); m/z=462 ($M^+$+1)

Reference Example 62

2-(7-Chloro-6-ethylthioquinolin-2-yl)methoxy-11-hydroxy-6,11-dihydrodibenz[b,e]oxepine The title compound was obtained from the compound obtained in Reference example 61 by the same method as in Reference example 35.

Mass (CI); m/z=464 ($M^+$+1)

Reference Example 63

11-(2-Carbamoylethylthio)-2-(7-chloroquinolin-2-yl)methoxy-6,11-dihydrodibenz[b,e]oxepine 0.98 g of 1,1'-carbonyldiimidazole was added to 1.99 g of 11-(2-carboxyethylthio)-2-(7-chloroquinolin-2-yl)methoxy-6,11-dihydrodibenz[b,e]oxepine obtained in Example 2 dissolved in 33 ml of tetrahydrofuran and the mixture was stirred at room temperature for 4 hours. Then, 4 ml of conc.

aqueous ammonia was added to the mixture and the mixture was stirred at room temperature for 10 minutes. The reaction mixture was condensed under reduced pressure, water was added to the residue, crystals were collected by filtration and the crystals were dissolved in chloroform. After this chloroform solution was washed with water and dried over anhydrous sodium sulfate, solid obtained by removing the solvent was washed with an acetone-hexane mixed solution to obtain 1.99 g of the title compound.

Mass (CI); m/z=491 ($M^+$+1)

Reference Example 64

2-(7-Chloroquinolin-2-yl)methoxy-11-(2-cyanoethylthio)-6,11-dihydrodibenz[b,e]oxepine Under ice cooling and stirring, 1.35 ml of phosphorus oxy-chloride was added dropwise over 40 minutes to 1.78 g of 11-(2-carbamoylethylthio)-2-(7-chloroquinolin-2-yl)methoxy-6,11-dihydrodibenz[b,e]oxepine obtained in Reference example 63 dissolved in 14 ml of dimethylformamide and the mixture was stirred at the same temperature for 30 minutes. The reaction mixture was added 250 ml of a 1% sodium hydroxide aqueous solution, crystals precipitated were collected by filtration and the crystals were dissolved in chloroform. After this chloroform solution was washed with water and dried over anhydrous sodium sulfate, the solvent was removed to obtain 1.62 g of the title compound.

Mass (CI); m/z=473 ($M^+$+1)

Reference Example 65

11-(2-Cyanoethylthio)-2-(quinolin-2-yl)methoxy-6,11-dihydrodibenz[b,e]oxepine

The title compound was obtained from the compound obtained in Example 11 by the same operation procedures as described in Reference example 63 and Reference example 64.

Mass (CI); m/z=439 ($M^+$+1)

Reference Example 66

2-(7-Chloroquinolin-2-yl)methoxy-11-(2-cyanoethoxy)-6,11-dihydrodibenz[b,e]oxepine Under ice cooling and stirring, 0.27 ml of thionyl chloride was added 1.5 g of 2-(7-chloroquinolin-2-yl)methoxy-11-hydroxy-6,11-dihydrodibenz[b,e]oxepine obtained in Reference example 36 suspended in 30 ml of methylene chloride and the mixture was stirred at the same temperature for 40 minutes. After completion of the reaction, the reaction mixture was condensed under reduced pressure, the residue was dissolved in 12 ml of methylene chloride, 0.81 ml of ethylenecyanhydrin and 0.94 ml of triethylamine were added to the solution under ice cooling and stirring and the mixture was stirred at room temperature for 2.5 hours. The reaction mixture was washed with water and the organic layer was dried over anhydrous sodium sulfate. Solid obtained by removing the solvent was washed with a diethyl ether-hexane mixed solution to obtain 1.31 g of the title compound.

Mass (CI); m/z=457 ($M^+$+1)

Reference Example 67

11-Cyanomethylthio-2-(quinolin-2-yl)methoxy-6,11-dihydrodibenz[b,e]oxepine

Under ice cooling and stirring, 0.44 g of mercaptoacetonitrile was added to 2.22 g of 11-hydroxy-2-(quinolin-2-yl)methoxy-6,11-dihydrodibenz[b,e]oxepine obtained in Reference example 45 dissolved in a mixed solution of 20 ml of trifluoroacetic acid and 10 ml of methylene chloride and the mixture was stirred at the same temperature for 1.5 hours. The residue obtained by condensing the reaction mixture under reduced pressure was dissolved in ethyl acetate and the organic layer was washed with a saturated sodium hydrogen carbonate aqueous solution and a saturated saline solution and dried over anhydrous sodium sulfate. The viscous residue obtained by removing the solvent was crystallized from diethyl ether to obtain 1.23 g of the title compound.

Mass (CI); m/z=425 ($M^+$+1)

Reference Example 68

2-(2-Aminoethylthio)-2-(7-chloroquinolin-2-yl)methoxy-6,11-dihydrodibenz[b,e]oxepine Under ice cooling and stirring, 0.19 g of 2-aminoethanethiol was added to 1 g of 2-(7-chloroquinolin-2-yl)methoxy-11-hydroxy-6,11-dihydrodibenz[b,e]oxepine obtained in Reference example 36 dissolved in a mixed solution of 7 ml of trifluoroacetic acid and 5.6 ml of methylene chloride and the mixture was stirred at the same temperature for 2 hours. Ice water was added to the reaction mixture, crystals obtained by neutralization with a 1N-sodium hydroxide aqueous solution were collected by filtration, these crystals were dissolved in methylene chloride and the organic layer was washed with water and then dried over anhydrous sodium sulfate. The residue obtained by removing the solvent was applied to silica gel column chromatography to obtain 0.58 g of the title compound. Mass (CI); m/z=463 ($M^+$+1)

Reference example 69

11-(2-Aminoethylthio)-2-(quinolin-2-yl)methoxy-6,11-dihydrodibenz[b,e]oxepine

The title compound was obtained from 11-hydroxy-2-(quinolin-2-yl)methoxy-6,11-dihydrodibenz[b,e]oxepine obtained in Reference example 45 by the same method as in Reference example 68.

Mass (CI); m/z=429 ($M^+$+1)

Reference Example 70

11-Hydroxyimino-2-(quinolin-2-yl)methoxy-6,11-dihydrodibenz[b,e]oxepine 5 g of 2-(quinolin-2-yl)methoxy-11-oxo-6,11-dihydrodibenz[b,e]oxepine obtained by the same method as in Reference example 34 and 9.46 g of hydroxylamine hydrochloride dissolved in 150 ml of pyridine were refluxed under heating for 20 hours. The reaction mixture was added to 1.2 liter of ice water and crystals precipitated were collected by filtration and then applied to silica gel column chromatography to obtain 1.96 g of the title compound.

Mass (CI); m/z=383 ($M^+$+1)

Reference Example 71

11-Acetylthio-2-(7-chloroquinolin-2-yl)methoxy-6,11-dihydrodibenz[b,e]oxepine

Under ice cooling and stirring, 1.25 ml of thioacetic acid was added to 7.03 g of 2-(7-chloroquinolin-2-yl)methoxy-11-hydroxy-6,11-dihydrodibenz[b,e]oxepine obtained in Reference example 36 dissolved in a mixed solution of 58 ml of trifluoroacetic acid and 30 ml of methylene chloride and the mixture was stirred at the same temperature for 3 hours. 300 ml of ice water was added to the reaction mixture, crystals precipitated by neutralization with a 1N-sodium hydroxide aqueous solution were collected by filtration and these crystals were dissolved in methylene chloride. Then, this organic layer was washed with water and dried over anhydrous sodium sulfate and then the solvent was removed. The resulting residue was applied to silica gel column chromatography to obtain 4.6 g of the title compound as white powder.

Mass (CI); m/z=462 ($M^+$+1)

Reference Example 72

2-(7-Chloroquinolin-2-yl)methoxy-11-mercapto-6,11-dihydrodibenz[b,e]oxepine

19 ml of a 1N-sodium hydroxide aqueous solution was added to 3.49 g of 11-acetylthio-2-(7-chloroquinolin-2-yl)methoxy-6,11-dihydrodibenz[b,e]oxepine obtained in Reference example 71 dissolved in 66 ml of ethanol and the mixture was stirred at room temperature for 1 hour. 250 ml of water was added to the reaction mixture and the mixture was adjusted to about pH 4 with 1N-hydrochloric acid. Crystals precipitated were dissolved in 300 ml of methylene chloride and the organic layer was washed with water and dried over anhydrous sodium sulfate. The solvent was removed to obtain 3.03 g of the title compound as a crude product.

Mass (CI); m/z=420 ($M^+$+1)

Reference Example 73

2-(7-Chloro-6-fluoroquinolin-2-yl)methoxy-8-iodo-11-(2-tetrahydropyranyloxy)-6,11-dihydrodibenz[b,e]oxepine

2.4 g of 3,4-dihydro-2H-pyrane and 0.14 g of pyridinium p-toluenesulfonate were added to 1.56 g of 2-(7-chloro-6-fluoroquinolin-2-yl)methoxy-11-hydroxy-8-iodo-6,11-dihydrodibenz[b,e]oxepine dissolved in 50 ml of methylene chloride obtained in Reference example 53 and the mixture was stirred at room temperature for 13.5 hours.

During the reaction, 8 ml of 3,4-dihydro-2-pyrane, 0.8 g of pyridinium p-toluenesulfonate and 100 ml of tetrahydrofuran were added to the mixture. After completion of the reaction, the reaction mixture was condensed under reduced pressure and the residue was dissolved in 100 ml of methylene chloride. Then, this methylene chloride solution was washed with a saturated sodium hydrogen carbonate solution and water and dried over anhydrous sodium sulfate. After the solvent was removed, the residue was applied to silica gel column chromatography to obtain 1.37 g of the title compound.

Mass (CI); m/z=632 ($M^+$+1)

Reference Example 74

2-(7-Chloro-6-fluoroquinolin-2-yl)methoxy-8-(2-acetylethyl)-11-(2-tetrahydropyranyloxy)-6,11-dihydrodibenz[b,e]oxepine

0.2 g of (±)-3-buten-2-ol, 1.4 mg of palladium (II) acetate and 0.27 g of triethylamine were added to 1.36 g of 2-(7-chloro-6-fluoroquinolin-2-yl)methoxy-8-iodo-11-(2-tetrahydropyranyloxy)-6,11-dihydrodibenz[b,e]oxepine obtain in Reference example 73 dissolved in 2.5 ml of acetonitrile and the mixture was refluxed under heating for 5.5 hours. After 60 ml of methylene chloride and 60 ml of ice water were added to this reaction mixture, the organic layer was separated, washed with water and dried over anhydrous sodium sulfate. After the solvent was removed, the residue was applied to silica gel column chromatography to obtain 0.76 g of the title compound.

Mass (CI); m/z=576 ($M^+$+1)

Reference Example 75

2-(7-Chloro-6-fluoroquinolin-2-yl)methoxy-11-hydroxy-8-(2-acetylethyl)-6,11-dihydrodibenz[b,e]oxepine

0.02 ml of trifluoroacetic acid was added to 0.73 g of 2-(7-chloro-6-fluoroquinolin-2-yl)methoxy-8-(2-acetylethyl)-11-(2-tetrahydropyranyloxy)-6,11-dihydrodibenz[b,e]oxepine obtained in Reference example 74 dissolved in a mixed solution of 5 ml of dioxane and 2 ml of water, the mixture was stirred at room temperature for 15 minutes, 4 ml of acetic acid was added to the mixture and the mixture was stirred for 10 hours. 80 ml of water was added to the reaction mixture and insolubles were removed by filtration. The residue was dissolved in chloroform and the organic layer was washed with water and dried over anhydrous sodium sulfate. After the solvent was removed, the residue was washed with a mixed solution of acetone and ether to obtain 0.41 g of the title compound.

Mass (CI); m/z=492 ($M^+$+1)

Test Example 1

Leukotriene $D_4$ receptor binding test

<Preparation of receptor samples>

As receptor samples, lung cell membrane fractions of guinea pigs were used. The membrane fractions were prepared according to the method of Ahn et al. (Ahn, H. S. & Barnett, A. (1986) Eur. J. Pharmacol., 127, 153.). After Hartley strain male guinea pigs (body weight: 400 to 500 g, supplied by Nihon SLC Co.) were killed by exsanguination, lungs were extracted and perfused with a physiological saline solution (Otsuka Seiyaku) from lung arteries. The extracted lungs were cut into pieces immediately or after the lungs were stored by freezing them at −80° C. A 10-fold amount of a buffer solution (pH 7.4) of 10 mM PIPES, 10 mM $MgCl_2$, 10 mM $CaCl_2$ and 50 mM NaCl was added thereto and the mixtures were made suspensions by a homogenizer (manufactured by Yamato Co., LP-41C Model). After the suspensions were filtered with gauze, the filtrates were centrifuged by an ultracentrifuge (manufactured by Hitachi Co., 70P-72 Model) with 50,000 g for 10 minutes, whereby membrane fractions were deposited. The membrane fractions were washed twice and then suspended in the same buffer solution to obtain receptor samples. Measurement of a protein concentration was conducted by the Lowry method (Lowry, O, H. et al. (1951) J. Biol.

Chem., 193,265.) by using bovine serum albumin as a standard protein. The samples prepared (protein amount: 10 to 25 mg/ml) were stored by freezing them at −80° C. and used for experiments.

<Leukotriene $D_4$ receptor binding test>

The leukotriene $D_4$ ($LTD_4$) receptor binding test was conducted according to the method of O'Sullivan et al. (O'Sullivan, B. P. & Mong, S. (1989) Mol. Pharmacol., 35, 795.). The receptor samples were diluted with a buffer solution (pH 7.4) of 10 mM PIPES, 10 mM $MgCl_2$, 10 mM $CaCl_2$ and 50 mM NaCl and 0.42 mg/ml in terms of a protein amount was used. As a labeling compound, [$^3$H]ICI-198615 (produced by Du Pont Co., 60 Ci/mmol) which specifically binds to the $LTD_4$ receptor was used. [$^3$H]ICI-198615 and a compound to be tested were dissolved in dimethylsulfoxide and a 1/50 amount (2% by volume) of the solution was added to the receptor-diluted solutions, respectively. 500 μl of each reaction mixture was incubated at 25° C. for 40 minutes and then filtered with a glass fiber filter (Whatman, GF/B type) by using a cell harvester (manufactured by Brandel Co., M-30R Model). The filters were washed with 10 ml of an ice-cooled 100 mM NaCl-50 mM phosphate buffer solution (pH 7.5) and subjected to ultrasonic treatment in 9 ml of a liquid scintillator (manufactured by Nacalai Tesque, Co., Clear sol I) for 2 minutes. Thereafter, radioactivity was measured by a liquid scintillation counter (manufactured by Packard Co., 2000 CA Model). In a test of determining a dissociation constant of ICI-198615, 0.1 to 2 nM [$^3$H]ICI-198615 and 10 μM non-radioactive ICI-198615 were used. In a test of determining inhibition constants of the respective compounds to be tested, [$^3$H]ICI-198615 having a concentration of about 0.2 nM and the compounds each having a concentration of 0.1 pM to 0.1 mM were used.

<Data analysis of receptor binding test>

The dissociation constant (Kd) of ICI-198615 and the binding inhibition constants (Ki) of the respective compounds to be tested were determined by the following numerical formulae (A), (B) and (C).

$$B/F=(Bmax-B)/Kd \quad (A)$$

$$Ki=IC_{50}/(1+[L]/Kd) \quad (B)$$

$$pKi=-\log Ki \quad (C)$$

wherein B: a concentration of a label [3H] which is bound to a receptor, Bmax: a maximum receptor-binding concentration of a label [$^3$H], F: a concentration of a label [$^3$H] which is not bound to a receptor, [L]: a concentration of a label [$^3$H], $IC_{50}$: a concentration of a compound which inhibits 50% of binding of a label [$^3$H] to a receptor and pKi: a logarithm, of a reciprocal of Ki.

Test example 2

Leukotriene $D_4$-induced respiratory contraction test

<Test animals>

Hartley strain male guinea pigs (body weight: 400 to 600 g, supplied by Nihon SLC Co.) were used and all of them were bred under conditions of constant temperature (23°±2° C.) and constant humidity (55°±10° C.). The animals which had been fasted for 24 hours before experiments were used.

<Medicines used>

$LTD_4$ (Funakoshi) dissolved in a physiological saline solution (Otsuka Seiyaku) was used. The compounds to be tested suspended in a 0.5% carboxymethyl cellulose aqueous solution were used.

<Operation method>

The operation was conducted according to the method of Konzett and Rossler (Konzett, H. and Rossler, R. Naunyn Schmiedebergs (1940) Arch. Exp. Pathol. Pharmacol., 195, 71.). Each guinea pig was anesthetized with urethane (1.5 g/kg, i.p.) and then fixed in the supine position. A trachea was incised and a ϕ type cannula was inserted into the trachea and connected to a respirator (Shinano Seisakusho, SN-480-7) for small animals. Artificial respiration with positive pressure was conducted with a pressure loaded to a lung of 10 cm $H_2O$, an air supplying rate of 5 ml/stroke and 60 strokes/min. The air supplying rate to the trachea was measured by differential pressure transducers (Nihon Koden, TU-241T and TP-602T) connected to the cannula in the trachea and recorded on a rectigraph (Nihon Koden, WT-645G Model).

$LTD_4$ (0.5 μg/kg/0.5 ml) was administered intravenously (i.v.) from a cannula inserted into a common jugular vein to cause shrinkage of a trachea. Subsequently, a compound to be tested was administered orally (p.o.) after 10 minutes and $LTD_4$ was administered intravenously (i.v.) again after 1 hour to cause shrinkage of the trachea. The results are shown by using a ratio of inhibiting a trachea-shrinking reaction before administering the compound to be tested.

The results of Test example 1 are shown in Table 19 and the results of Test example 2 in Table 20.

TABLE 19

Results of leukotriene $D_4$ receptor binding test

| Compound to be tested | pKi value | Compound to be tested | pKi value |
|---|---|---|---|
| Compound of Example 1 | 9.5 | Compound of Example 23 | 8.3 |
| Compound of Example 2 | 9.1 | Compound of Example 24 | 8.6 |
| Compound of Example 3 | 8.5 | Compound of Example 26 | 8.8 |
| Compound of Example 4 | 8.8 | Compound of Example 27 | 8.3 |
| Compound of Example 5 | 8.5 | Compound of Example 30 | 8.7 |
| Compound of Example 12 | 8.3 | Compound of Example 31 | 8.7 |
| Compound of Example 13 | 9.1 | Compound of Example 39 | 8.7 |
| Compound of Example 14 | 8.5 | Compound of Example 40 | 8.6 |
| Compound of Example 15 | 9.2 | Compound of Example 41 | 8.9 |
| Compound of Example 16 | 9.2 | Compound of Example 48 | 9.7 |
| Compound of Example 17 | 8.8 | Compound of Example 50 | 10.1 |
| Compound of Example 18 | 9.7 | Compound of Example 51 | 8.9 |
| Compound of Example 19 | 9.3 | Compound of Example 52 | 9.5 |
| Compound of Example 20 | 9.2 | Compound of Example 53 | 8.4 |
| Compound of Example 21 | 9.1 | Compound A | 8.2 |

Compound A: 5-[[2-[[4-(2-quinolinylmethoxy)phenoxy]methyl]phenyl]methyl]-1H-tetrazole (RG12525; J. Med. Chem., 1990, 33, 1194)

TABLE 20

| Results of leukotriene $D_4$-induced respiratory contraction test | |
|---|---|
| Compound to be tested | Inhibition ratio (%) (dose: 1 mg/kg) |
| Compound of Example 1 | 100 |
| Compound of Example 2 | 100 |
| Compound of Example 3 | 100 |
| Compound of Example 4 | 93 |
| Compound of Example 13 | 67 |
| Compound of Example 21 | 71 |
| Compound of Example 26 | 87 |
| Compound of Example 50 | 100 |
| Compound A | 51 |

Compound A: 5-[[2-[[4-(2-quinolinylmethoxy)phenoxy]methyl]phenyl]methyl]-1H-tetrazole (RG12525; J. Med. Chem., 1990, 33, 1194)

Utilizability in industry

The compound represented by the formula (I) of the present invention has a strong leukotriene antagonistic action and is extremely useful as an antiallergic medicine and an anti-inflammatory medicine.

As an administration form for that purpose, there may be mentioned, for example, oral administration by a tablet, a capsule, a granule, a powder, a syrup, etc. or parenteral administration by an intravenous injection, a intramuscular injection, a suppository, (an inhalant and an aerosol), etc. The dose varies depending on an age, a body weight, a symptom, an administration form, an administration time, etc., but it is generally about 1 to 1,000 mg to an adult per day in one dosage or divided into several dosages.

We claim:

1. A quinoline derivative represented by the formula

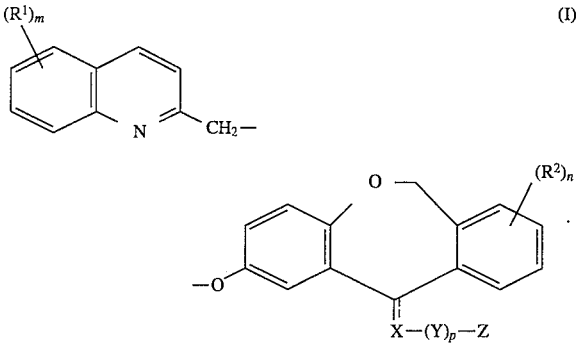

and a pharmaceutically acceptable salt thereof.

2. The quinoline derivative according to claim 1, wherein $R^1$ is a group selected from fluorine, chlorine, methyl, ethyl, difluoromethyl, trifluoromethyl, methoxy, ethoxy, difluoromethoxy, trifluoromethoxy and 2,2,2-trifluoroethoxy and m is 0, 1 or 2, and $R^2$ is a group selected from cyano, carbamoyl, fluorine, chlorine, bromine, methyl, ethyl, methoxy, ethoxy, methylthio, ethylthio, carboxy, tetrazol-5-yl, carboxymethyl, 2-carboxyethyl, carboxymethoxy, 2-carboxyethoxy, carboxymethylthio, 2-carboxyethylthio, 2-(tetrazol-5-yl)ethyl, (tetrazol-5-yl)methoxy, 2-(tetrazol-5-yl)ethoxy, (tetrazol-5-yl)methylthio, 2-(tetrazol-5-yl)ethylthio, 2-acetylethyl and 2-propanoylethyl and n is 0 or 1, and a pharmaceutically acceptable salt thereof.

3. The quinoline derivative according to claim 1, wherein $R^1$ is chlorine or fluorine, m is 1 or 2 and n is 0 or 1, and a pharmaceutically acceptable salt thereof.

4. The quinoline derivative according to any one of claims 1 to 3, wherein X is an oxygen atom, a sulfur atom, a methylene group or a formula of =CH—, Y is a $C_1$ to $C_4$ alkylene group and p is 1, and Z is carboxy, tetrazol-5-yl, trifluoroacetylamino, trifluoromethanesulfonylamino, phenylsulfonylamino, 2-methylphenylsulfonylamino, 4-carboxyphenylsulfonylamino, 4-(tetrazol-5-yl)phenylsulfonylamino, trifluoromethanesulfonylaminocarbonyl, phenylsulfonylaminocarbonyl, 2-methylphenylsulfonylaminocarbonyl, 4-carboxyphenylsulfonylaminocarbonyl or 4-(tetrazol-5-yl)phenylsulfonylaminocarbonyl, and a pharmaceutically acceptable salt thereof.

5. The quinoline derivative according to any one of claims 1 to 3, wherein X is an oxygen atom or a sulfur atom, Y is a $C_1$ to $C_3$ alkylene group, p is 1 and Z is carboxy or tetrazol-5-yl, and a pharmaceutically acceptable salt thereof.

6. The quinoline derivative according to claim 1, which is
11-(2-carboxyethylthio)-2-(7-chloro-6-fluoroquinolin-2-yl)methoxy-6,11-dihydrodibenz[b,e]oxepine,
11-(2-carboxyethylthio)-2-(7-chloroquinolin-2-yl)methoxy-6,11-dihydrodibenz[b,e]oxepine,
11-(2-carboxyethylthio)-2-(6-fluoroquinolin-2-yl)methoxy-6,11-dihydrodibenz[b,e]oxepine,
11-(2-carboxyethylthio)-2-(7-fluoroquinolin-2-yl)methoxy-6,11-dihydrodibenz[b,e]oxepine,
11-(2-carboxyethylthio)-2-(6-chloroquinolin-2-yl)methoxy-6,11-dihydrodibenz[b,e]oxepine,
11-(2-carboxyethylthio)-2-(7-chloroquinolin-2-yl)methoxy-10-methyl-6,11-dihydrodibenz[b,e]oxepine,
11-(2-carboxyethylthio)-2-(7-chloroquinolin-2-yl)methoxy-8-methoxy-6,11-dihydrodibenz[b,e]oxepine,
8-bromo-11-(2-carboxyethylthio)-2-(7-chloroquinolin-2-yl)methoxy-6,11-dihydrodibenz[b,e]oxepine,
11-(2-carboxyethylthio)-2-(7-chloroquinolin-2-yl)methoxy-7-cyano-6,11-dihydrodibenz[b,e]oxepine,
11-(2-carboxyethylthio)-8-carboxymethylthio-2-(7-chloroquinolin-2-yl)methoxy-6,11-dihydrodibenz[b,e]oxepine,
11-(2-carboxyethylthio)-2-(quinolin-2-yl)methoxy-8-(tetrazol-5-yl)-6,11-dihydrodibenz[b,e]oxepine,
11-(2-carboxyethylthio)-2-(7-chloroquinolin-2-yl)methoxy-8-(tetrazol-5-yl)-6,11-dihydrodibenz[b,e]oxepine,
11-(2-carboxyethylthio)-2-(7-chloroquinolin-2-yl)methoxy-7-(tetrazol-5-yl)-6,11-dihydrodibenz[b,e]oxepine,
7-carbamoyl-11-(2-carboxyethylthio)-2-(7-chloroquinolin-2-yl)methoxy-6,11-dihydrodibenz[b,e]oxepine,
11-carboxymethylthio-2-(7-chloroquinolin-2-yl)methoxy-6,11-dihydrodibenz[b,e]oxepine,
11-(1-carboxyethylthio)-2-(quinolin-2-yl)methoxy-6,11-dihydrodibenz[b,e]oxepine,
11-(3-carboxypropylthio)-2-(7-chloroquinolin-2-yl) methoxy-6,11-dihydrodibenz[b,e]oxepine,
11-carboxymethoxy-2-(6-chloroquinolin-2-yl)methoxy-6,11-dihydrodibenz[b,e]oxepine,
11-carboxymethoxy-2-(7-chloroquinolin-2-yl)methoxy-6,11-dihydrodibenz[b,e]oxepine,
2-(7-chloroquinolin-2-yl)methoxy-11-[2-(tetrazol-5-yl)ethylthio]6,11-dihydrodibenz[b,e]oxepine,
2-(7-chloroquinolin-2-yl)methoxy-11-[2-(tetrazol-5-yl)ethoxy]6,11-dihydrodibenz[b,e]oxepine or
11-(2-carboxyethylthio)-2-(7-chloro-6-fluoroquinolin-2-yl)methoxy-8-(2-acetylethyl)-6,11-dihydrodibenz[b,e]oxepine,
and a pharmaceutically acceptable salt thereof.

7. The quinoline derivative according to claim 1, which is 11-[(phenylsulfonyl)aminocarbonyl]methylthio-2-(7-chloroquinolin-2-yl)methoxy-6,11-dihydrodibenz[b,e]oxepine, 2-(7-chloroquinolin-2-yl)methoxy-11-[2-[(2-methylphenyl-sulfonyl)aminocarbonyl]ethylthio]-6,11-dihydrodibenz[b,e]oxepine or
11-[(phenylsulfonyl)aminocarbonyl]methylthio-2-(quinolin-2-yl)methoxy-6,11-dihydrodibenz[b,e]oxepine,
and a pharmaceutically acceptable salt thereof.

8. The quinoline derivative according to claim 1, wherein the compound is
(+)-11-(2-carboxyethylthio)-2-(7-chloro-6-fluoroquinolin-2-yl)methoxy-6,11-dihydrodibenz[b,e]oxepine or
(+)-11-(2-carboxyethylthio)-2-(7-chloroquinolin-2-yl)methoxy-6,11-dihydrodibenz[b,e]oxepine.

9. The quinoline derivative according to claim 1, wherein the compound is protected by an ester when Z is a carboxy group.

10. The quinoline derivative according to claim 9, wherein the compound is 2-(7-chloroquinolin-2-yl)methoxy-11-(3-ethoxycarbonylpropylthio)-6,11-dihydrodibenz[b,e]oxepine or
2-(6-chloroquinolin-2-yl)methoxy-11-methoxycarbonylmethoxy-6,11-dihydrodibenz[b,e]oxepine.

* * * * *

UNITED STATES PATENT AND TRADEMARK OFFICE
CERTIFICATE OF CORRECTION

PATENT NO. : 5,591,752
DATED : January 7, 1997
INVENTOR(S) : Tomio KIMURA et al.

It is certified that error appears in the above-indentified patent and that said Letters Patent is hereby corrected as shown below:

Claim 1, before line 49 (after the formulas), insert
--[wherein $R^1$ represents a group selected from a halogen atom, a lower alkyl roup, a halogeno-lower alkyl group, a lower alkoxy group, a halogeno-lower lkoxy group, a lower alkylthio group and a halogeno-lower alkylthio group, represents 0 or an integer of 1 to 4 and when m is 2 to 4, $R^1$s may be ifferent from each other,
$R^2$ represents a group selected from a halogen atom, a hydroxyl group, a itro group, a cyano group, a carbamoyl group, a carboxy group, a tetrazol-5-yl roup, a lower alkyl group or a lower alkoxy group or a lower alkylthio group hich may be substituted by carboxy or tetrazol-5-yl, and an alkanoyl-lower lkyl group, n represents 0 or an integer of 1 to 4 and when n is 2 to 4, $R^2$s ay be different from each other.
X represents an oxygen atom, a sulfur atom, a methylene group, a formula f =CH- or a formula of =N-O-.

UNITED STATES PATENT AND TRADEMARK OFFICE
CERTIFICATE OF CORRECTION

PATENT NO. : 5,591,752
DATED : January 7, 1997
INVENTOR(S) : Tomio KIMURA et al.

It is certified that error appears in the above-identified patent and that said Letters Patent is hereby corrected as shown below:

Y represents a straight or branched alkylene group,

Z represents a carboxy group, a tetrazol-5-yl group, a (tetrazol-5-yl)aminocarbonyl group, a (tetrazol-5-yl)carbonylamino group, a formula of -NH-CO-$R^3$, a formula of -NH-$SO_2$-$R^3$ or a formula of -CO-NH-$SO_2$-$R^3$ (wherein $R^3$ represents a lower alkyl group which may be substituted by a halogen, or a phenyl group which may be substituted by a halogen, a lower alkyl, a halogeno-lower alkyl, a lower alkoxy, a halogeno-lower alkoxy, nitro, cyano, carboxy or tetrazol-5-yl).

p represents 0 or 1.

······ represents a single bond or a double bond].

Signed and Sealed this

Twelfth Day of January, 1999

Attest:

*Attesting Officer*            *Acting Commissioner of Patents and Trademarks*